United States Patent
Atwood et al.

(10) Patent No.: US 9,695,156 B2
(45) Date of Patent: Jul. 4, 2017

(54) COMPOUNDS FOR THE TREATMENT AND PREVENTION OF INFECTIONS

(71) Applicant: Brown University, Providence, RI (US)

(72) Inventors: Walter Atwood, Rumford, RI (US);
Christian Nelson, Branford, CT (US);
Jason K. Sello, Providence, RI (US);
Daniel William Carney, San Diego, CA (US)

(73) Assignee: Brown University, Providence, RI (US)

( * ) Notice: Subject to any disclaimer, the term of this patent is extended or adjusted under 35 U.S.C. 154(b) by 0 days.

(21) Appl. No.: 14/415,177

(22) PCT Filed: Jul. 15, 2013

(86) PCT No.: PCT/US2013/050479
§ 371 (c)(1),
(2) Date: Jan. 16, 2015

(87) PCT Pub. No.: WO2014/014814
PCT Pub. Date: Jan. 23, 2014

(65) Prior Publication Data
US 2015/0166517 A1 Jun. 18, 2015

Related U.S. Application Data

(60) Provisional application No. 61/671,998, filed on Jul. 16, 2012, provisional application No. 61/799,043, filed on Mar. 15, 2013.

(51) Int. Cl.
*A61K 31/517* (2006.01)
*C07D 409/04* (2006.01)
*C07D 403/04* (2006.01)
*C07D 405/04* (2006.01)

(52) U.S. Cl.
CPC .......... *C07D 409/04* (2013.01); *A61K 31/517* (2013.01); *C07D 403/04* (2013.01); *C07D 405/04* (2013.01)

(58) Field of Classification Search
CPC ... C07D 409/04; C07D 405/04; C07D 403/04
See application file for complete search history.

(56) References Cited

U.S. PATENT DOCUMENTS

| | | | |
|---|---|---|---|
| 8,609,732 B2 | 12/2013 | Gillet et al. | |
| 2007/0244098 A1 * | 10/2007 | Brown | A61K 31/47 514/221 |
| 2011/0201601 A1 | 8/2011 | Gillet et al. | |
| 2012/0283249 A1 | 11/2012 | Lopez et al. | |
| 2014/0073633 A1 | 3/2014 | Gillet et al. | |

FOREIGN PATENT DOCUMENTS

| | | | | |
|---|---|---|---|---|
| WO | WO 00/26197 A1 | 5/2000 | | |
| WO | WO 01/81340 A2 | 11/2001 | | |
| WO | WO 2004/018462 A1 | 3/2004 | | |
| WO | WO2004018462 | * | 3/2004 | .......... C07D 413/04 |
| WO | WO 2009/153457 A2 | 12/2009 | | |
| WO | WO 2009/153665 A2 | 12/2009 | | |

OTHER PUBLICATIONS

Vippagunt et al. (2001).*
Wolff et al. (1997).*
International Preliminary Report on Patentability for PCT/US2013/050479, mailed Jan. 29, 2015.
International Search Report and Written Opinion for PCT/US2013/050479, mailed Nov. 8, 2013.
El-Khamry et al., Synthesis of 2-(2'-thienyl)-3,1-(4H)-benzoxazin-4-one and its reactions with different nucleophiles. Revue Roumaine de Chimie (1988), 33(8), 833-8. Ain Shams University EG.
El-Khamry et al., Synthesis of 2-(2'-thienyl)-3,1-(4H)-benzoxazin-4-one and its reactions with different nucleophiles. Egyptian Journal of Chemistry (1990), 1988, 31(2), 241-9. Ain Shams University EG.
Longhi et al., Lactoferrin inhibits early steps of human BK polyomavirus infection. Antiviral Res. Nov. 2006;72(2):145-52. Epub Jun. 2, 2006.

(Continued)

Primary Examiner — Paul V Ward
(74) Attorney, Agent, or Firm — Wolf, Greenfield & Sacks, P.C.

(57) ABSTRACT

Provided herein are compounds of Formula (I) or (II): (I) (II) pharmaceutically acceptable salts, tautomers, prodrugs, and stereoisomers thereof, and pharmaceutical compositions thereof, wherein X, $R^N$, $R^1$, $R^3$, $R^4$, p, and m are as defined herein. Such compounds and compositions have been found useful in the treatment or prevention of viral infections, e.g., polyomaviral infections, and are further envisioned useful in treatment or prevention of other pathogenic conditions associated with endosomal trafficking. Methods of treating or preventing an infection by a pathogen secreting an $AB_5$ toxin is also contemplated.

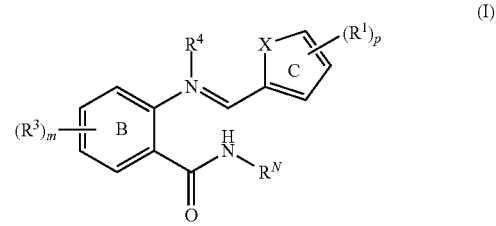

(I)

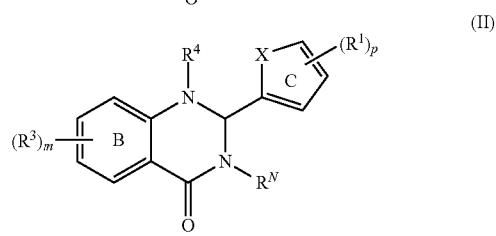

(II)

37 Claims, 19 Drawing Sheets

(56) References Cited

OTHER PUBLICATIONS

Low et al., Inhibition by brefeldin A of protein secretion from the apical cell surface of Madin-Darby canine kidney cells. J Biol Chem. Sep. 25, 1991;266(27):17729-32.

Narasimhulu et al., Ethylenediamine diacetate-catalyzed three-component reaction for the synthesis of 2,3-dihydroquinazolin-4(1H)-ones and their spirooxindole derivatives. Tetrahedron 2011 67: 9627-9634.

Nelson et al., A retrograde trafficking inhibitor of ricin and shiga-like toxins inhibits infection of cells by human and monkey polyomaviruses. MBio. Nov. 12, 2013;4(6):e00729-13. doi: 10.1128/mBio.00729-13.

Nelson, Inhibition of Polyomavirus replication by a small molecular weight inhibitor. American Society for Virology 31st Annual Meeting, Presented in Workshop #40-12, Jul. 23, 2012. 18 pages.

Niknam et al., Silica-bonded N-propylsulfamic acid as a recyclable catalyst for the synthesis of 2,3-dihydroquinazolin-4(1H)-ones. Chinese Chemical Letters, 2011, 22(1), 69-72. Islamic Azad University [IR].

Niknam et al., Silica-bonded S-sulfonic acid as a recyclable catalyst. Chinese Journal of Chemistry, 2011, 29(7), 1417-1422. Persian Gulf University [IR].

Noto et al., NMR analysis of restricted internal rotation in 2-substituted 2,3-dihydro-3-*o*-tolyl(*o*-chlorophenyl)-4(1*H*)-quinazolinones. Journal of Heterocyclic Chemistry (1996), 33(4), 1067-1071. dell'Università Via Archirafi, IT.

Park et al., Chemical structure of Retro-2, a compound that protects cells against ribosome-inactivating proteins. Sci Rep. 2012;2:631. doi: 10.1038/srep00631. Epub Sep. 5, 2012.

Prakash et al., Highly Enantioselective Synthesis of 2,3-Dihydroquinazolinones through Intramolecular Amidation of Imines. Org Lett 2012 14: 1896-1899.

Sharma et al., Cyanuric chloride catalyzed mild protocol for synthesis of biologically active dihydro/spiro quinazolinones and quinazolinone-glycoconjugates. J Org Chem. Jan. 20, 2012;77(2):929-37. doi: 10.1021/jo2020856. Epub Jan. 9, 2012.

Shaterian et al., Synthesis of 2,3-Dihydroquinazoline-4(1h)-Ones. Synthetic Communications 2010 40: 1231-1242.

Stechmann et al., Inhibition of retrograde transport protects mice from lethal ricin challenge. Cell. Apr. 16, 2010;141(2):231-42. doi: 10.1016/j.cell.2010.01.043.

Wang et al., Strontium chloride-catalyzed one-pot synthesis of 2,3-dihydroquinazolin-4(1*H*)-ones in protic media. Chinese Chemical Letters 2011 22: 1423-1426.

\* cited by examiner

JCPyV + Retro-2cycl, 15 DPI

JCPyV + DMSO, 15 DPI

Retro-2$^{cycl}$

COMPOUNDS FOR THE TREATMENT AND PREVENTION OF INFECTIONS

RELATED APPLICATIONS

The present application is a national stage filing under 35 U.S.C. §371 of international PCT application, PCT/US2013/050479, filed Jul. 15, 2013, which claims priority under 35 U.S.C. §119(e) to U.S. provisional patent applications, U.S. Ser. No. 61/671,998, filed Jul. 16, 2012, and U.S. Ser. No. 61/799,043, filed Mar. 15, 2013, each of which is incorporated herein by reference.

GOVERNMENT SUPPORT

This invention was made with Government support under grant numbers F32 NS070687 and P01 NS065719 awarded by the National Institutes of Health. The Government has certain rights in the invention.

BACKGROUND OF THE INVENTION

Members of the polyomavirus family, Polyomaviridae, infect mammals (rodents, bovines, primates/humans) and birds (fowl, psittacines) and can severely affect various organs in these subjects. So far, ten human polyomaviruses have been described. Two of these, JC-polyomavirus (JCPyV or JCV) and BK-polyomavirus (BKPyV or BKV) are established pathogens which are known to cause severe disease in humans. For example, in immunosuppressed subjects, lytic infection of oligodendrocytes by JCV results in the fatal demyelinating disease, progressive multifocal leukoencephalopathy (PML). BKV infection in immunosuppressed subjects results in kidney necrosis and polyomavirus-induced neuropathy (PVN). Two other closely-related polyomaviruses, KI-polyomavirus (KIPyV or KIV; Karolinska Institute) and WU-polyomavirus (WUPyV or WUV; Washington University), discovered almost simultaneously in 2007, have been isolated from respiratory secretions and may be associated with respiratory tract infection. See, e.g., Allander et al., *J. of Virol.* (2007) 81: 4130-6; Gaynor et al., *PLoS Pathogens* (2007) 3: e64. Merkel cell polyomavirus (MCPyV or MCV), discovered in 2008, has been found to be integrated in a large proportion of Merkel cell carcinomas of the skin. See, e.g., Feng et al., *Science* (2008) 319: 1096-100. In 2010, three new skin infecting polyomaviruses, HPyV6, HPyV7, and trichodysplasia spinulosa-associated polyomavirus (TSPyV or TSV), were discovered. See, e.g., Schowalter et al., *Cell Host Microbe* (2010) 7:509-515; Meijden et al., *PLoS Pathogens* (2010) 6:e1001024. For example, TSV was discovered in proliferative skin lesions (trichodysplasia spinulosa) seen in immunosuppressed patients. Meijden in supra. In March 2011, a ninth polyoma virus HPyV9, related to a monkey lymphotropic virus (LPV), was cultured from the blood of immunosuppressed patients. See, e.g., Trusch et al., *J. Gen. Virol.* (2012) 93:698-705. Most recently, in 2012, a new polyoma virus was reported isolated from the stool of a healthy child from Malawi. See, e.g., Siebrasse et al., *J. Virol.* "Identification of MW polyomavirus, a novel polyomavirus in human stool" 86:10321-10326.

Polyomaviruses, such as JCV and BKV, are a highly common source of childhood and young adult infection. A large majority of these infections appear to cause little or no symptoms and are probably lifelong persistent among almost all adults. Diseases caused by polyomavirus infections are most common among subjects who become immunosuppressed due to AIDS or old age, or after organ transplantation. Unfortunately, effective vaccines or antiviral therapies targeting these viruses do not currently exist. Thus, there remains a need for therapies to treat and prevent viral infections such as polyomavirus infections.

SUMMARY OF THE INVENTION

The present invention is based on the discovery that the imine 2-(((5-methylthiophen-2-yl)methylene)amino)-N-phenylbenzamide (RETRO-2) and/or the corresponding cyclized product, 2-(5-methylthiophen-2-yl)-3-phenyl-2,3-dihydroquinazolin-4(1H)-one (Retro-2$^{cycl}$) are inhibitors of polyomavirus (JCV, BKV, and SV40) infectivity. RETRO-2 was initially described in Stechmann et al., *Cell* (2010) 141:231-242 as an AB$_5$ toxin inhibitor against ricin and Shiga-like toxin infectivity, but its use as an inhibitor of against viral infectivity, such as polyomavirus infectivity, was not at that time appreciated.

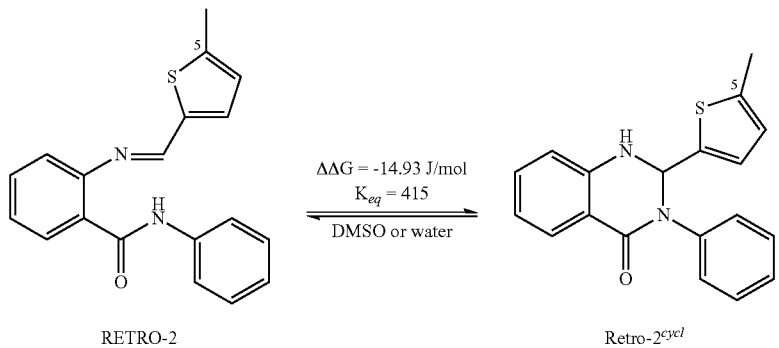 [SMILES: Cc1ccc(/C=N/c2ccccc2C(=O)Nc2ccccc2)s1 ; Cc1ccc(C2Nc3ccccc3C(=O)N2c2ccccc2)s1]

RETRO-2 rapidly converts to Retro-2$^{cycl}$ in solution, and it is likely that the active compound against polyomaviral infectivity is Retro-2$^{cycl}$. A preliminary structure activity relationship (SAR) study of Retro-2$^{cycl}$ indicates replacing the methyl group at position 5 of the thiophenyl ring with an ethyl group to provide BU62382A4 does not negatively impact potency against polyomavirus infectivity. It is envisioned that varying substitution at the 5-position of the thiophenyl ring and/or substitution on one or both of the phenyl rings may lead to other potent inhibitors of polyomaviral infection. It is further envisioned that such compounds may also exhibit good activity against other conditions, e.g., other pathogenic conditions associated with endosomal trafficking or sorting.

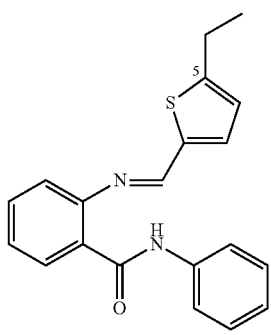

RETRO-2A4

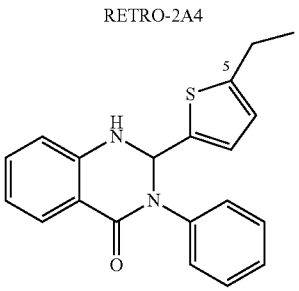

BU6238A4

Thus, in one aspect, provided is a method of treating a viral infection, the method comprising administering to a subject suffering from or likely to suffer from a viral infection an effective amount of a compound of Formula (I) or (II):

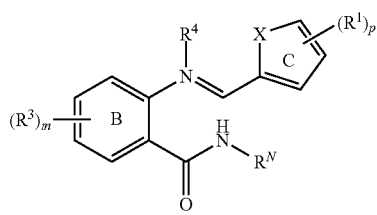
(I)

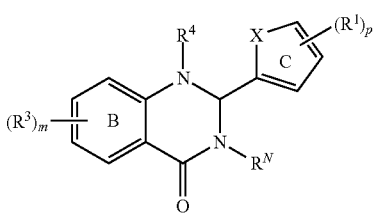
(II)

or a mixture thereof, or pharmaceutically acceptable salt, tautomer, prodrug, or stereoisomer thereof; wherein ====, X, $R^1$, $R^2$, $R^3$, $R^4$, p and m are as defined herein.

In certain embodiments, X is S.

In certain embodiments, $R^1$ is halo or substituted or unsubstituted $C_{1-6}$ alkyl. In certain embodiments, $R^1$ is methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), or n-hexyl ($C_6$).

In certain embodiments, $R^N$ is hydrogen, substituted or unsubstituted alkyl, substituted or unsubstituted alkenyl, substituted or unsubstituted alkynyl.

In certain embodiments, $R^N$ is a group of formula:

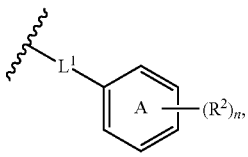

wherein:
$L^1$ is a bond, substituted or unsubstituted alkylene, substituted or unsubstituted alkenylene, or substituted or unsubstituted alkynylene;

each instance of $R^2$ is independently halo, $-NO_2$, $-CN$, $-SCN$, $-OR^{A2}$, $-SR^{A2}$, $-N(R^{A2})_2$, $-C(=O)R^{A2}$, $-OC(=O)R^{A2}$, $-SC(=O)R^{A2}$, $-NR^{A2}C(=O)R^{A2}$, $-S(=O)_2R^{A2}$, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, and substituted or unsubstituted heteroaryl, each instance of $R^{A2}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, substituted or unsubstituted hydroxyl, substituted or unsubstituted amino, substituted or unsubstituted thiol, an oxygen protecting group when attached to an oxygen atom, a sulfur protecting group when attached to a sulfur atom, or a nitrogen protecting group when attached to a nitrogen atom, or two $R^{A2}$ groups are joined to form a substituted or unsubstituted heterocyclic or heteroaryl ring;

or two $R^2$ groups are joined to form a substituted or unsubstituted aryl, substituted or unsubstituted heteroaryl, substituted or unsubstituted carbocyclic, or substituted or unsubstituted heterocyclic ring; and n is 0, 1, 2, 3, 4 or 5.

In certain embodiments, each instance of $R^2$ is independently halo, $-NO_2$, $-OR^{A2}$. In certain embodiments, $L^1$ is a bond. In certain embodiments, $L^1$ is substituted or unsubstituted $C_1$alkylene, substituted or unsubstituted $C_2$alkylene, substituted or unsubstituted $C_3$alkylene.

In certain embodiments, m is 0 or 1. In certain embodiments, each instance of $R^3$ is independently halo or substituted or unsubstituted alkyl.

In certain embodiments, $R^4$ is hydrogen. In certain embodiments, ==== corresponds to a double bond.

In yet another aspect, provided is a method of treating a pathogenic condition associated with endosomal trafficking, the method comprising administering to a subject suffering from or likely to suffer from the condition an effective amount of a compound of Formula (I) or (II), or a mixture thereof, or pharmaceutically acceptable salt, tautomer, prodrug, or stereoisomer thereof; herein ====, X, $R^1$, $R^2$, $R^3$, $R^4$, p, and m are as defined herein. In certain embodiments, the pathogenic condition is a bacterial infection. In certain embodiments, the pathogenic condition is a viral infection.

In certain embodiments, the compound inhibits retrograde endosomal transport of the pathogen (viral) genome to the cell nucleus.

In certain embodiments, the viral infection is an infection caused by human papillomavirus (HPV). In certain embodiments, the HPV is HPV-16 or HPV-18.

In certain embodiments, the viral infection is an infection caused by human immunodeficiency virus (HIV). In certain embodiments, the HIV is HIV type 1 (HIV-1).

In certain embodiments, the viral infection is an infection caused by influenza virus.

In certain embodiments, the viral infection is an infection caused by polyomavirus. In certain embodiments, the polyomavirus is JC-polyomavirus, BK-polyomavirus KI-polyomavirus, WU-polyomavirus, Merkel cell polyomavirus, HPyV6, HPyV7, trichodysplasia spinulosa-associated polyomavirus, HPyV9, MW polyomavirus, or the monkey polyomavirus SV40.

In still yet another aspect, provided is a method of treating an infection by a pathogen secreting $AB_5$ toxin, the method comprising administering to a subject suffering from or likely to suffer from the infection an effective amount of a compound of Formula (I) or (II). In certain embodiments, the pathogen secreting $AB_5$ toxin is bacteria. In certain embodiments, pathogen is *E. coli*. In certain embodiments, the $AB_5$ toxin is selected from the group consisting of ricin, Shiga toxin, Shiga-like toxins, cholera toxin, heat-labile enterotoxin, pertussis toxin, and subtilase cytotoxin.

In yet another aspect, provided are novel compounds of Formula (I) and (II), or pharmaceutically acceptable salts, tautomers, prodrugs, or stereoisomers thereof, provided the compound is not:

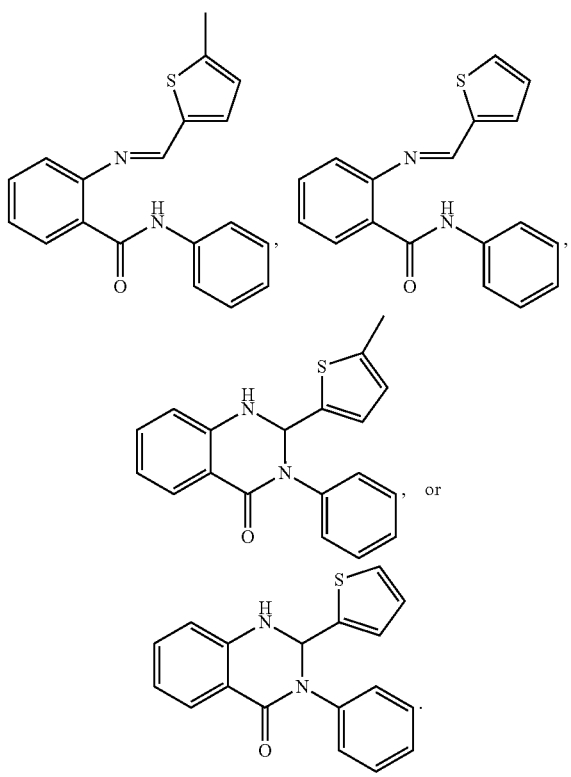

In still yet another aspect, provided are pharmaceutical compositions comprising a compound of Formula (I) and (II), or pharmaceutically acceptable salts, tautomers, prodrugs, or stereoisomers thereof, and a pharmaceutically acceptable excipient. In certain embodiments, the pharmaceutical composition is useful as a medicament for the treatment and prevention of an infection or condition as described herein.

The details of one or more embodiments of the invention are set forth in the Detailed Description of Certain Embodiments, as described below. Other features, objects, and advantages of the invention will be apparent from the Definitions, Examples, Figures, and Claims.

BRIEF DESCRIPTION OF THE DRAWINGS

FIG. 1A: Dose dependent effect of Retro-$2^{cycl}$ treatment on infection. Cells were pre-incubated with the indicated concentrations of Retro-$2^{cycl}$ prior to infection with JCpyV, BKpyV, and SV40 at an MOI of 0.5. Cells were fixed and stained for VP1 and infected cells were scored by flow cytometry. Infections were normalized to a vehicle control treated infected sample. Data represents the mean of three replicates and error bars represent the standard deviation. FIG. 1B: Retro-$2^{cycl}$ does not block infection of Adenovirus pseudovirus. Vero cells were pretreated with equivalent concentrations of Retro-$2^{cycl}$ as A prior to infection with an Ad5-GFP pseudovirus at an MOI of 0.5. Cells were detached at 72 hpi and GFP positive cells were scored by flow cytometry and normalized to a DMSO treated sample. Data represents the mean of three replicates and error bars indicate standard deviation.

FIG. 8A: Condensation of 2-aminobenzailide with 4-methyl-2-thiophencarboxaldehyde in methanol yields two products termed Retro-2 and Retro-$2^{cycl}$. These compounds were separated and independently characterized. FIG. 8B: The structure of Retro-$2^{cycl}$, shown in ball and stick representation, was solved by x-ray diffraction and was verified to be a dihydroquinazolanone. FIG. 8C: Retro-$2^{cycl}$ protects cells from infection by polyomaviruses. Cells were pretreated with Retro-2 analogs and infected with JCPyV at an MOI of 0.5. Retro-2 and Retro-$2^{cycl}$ were shown to be equally effective in reducing infectivity, suggesting that Retro-2 rapidly converts to Retro-$2^{cycl}$ in solution. Conversely, a reduced form of Retro-2 or a meta substituted form of Retro-2, which cannot cyclize, poorly inhibit JCPyV infectivity As a positive control, cells were incubated with 20 ng/mL of brefeldin A, and this was shown to be highly neutralizing of JCPyV infectivity. Cells were fixed and stained for VP1 and infected cells were scored by flow cytometry. Infected cells were normalized to a vehicle treated control and an uninfected, vehicle control sample was included to ensure no background signal existed. Data represent the average of triplicate samples. Error bars indicate standard deviation. FIG. 8D: Treatment of Retro-2 with sodium cyanoborohydride and acetic acid in methanol results in the formation of Retro-2$^{red}$, which is unable to cyclize. Observation of such a reaction indicates that Retro-2 and Retro-2$^{cycl}$ are in equilibrium under protic conditions. FIG. 8E: Retro-2$^{meta}$, a regioisomer of Retro-2 that is also unable to cyclize.

FIG. 10A: Colocalization was assessed using Manders coefficients of colocalization and at least five cells were analyzed per sample. Error bars denote standard deviation. FIG. 10B: Cells were pretreated with the indicated drug for 0.5 h prior to inoculation with JCpyV, BKpyV, or SV40 at an MOI of 1 or CTxB (2.0 µg/mL). Cells were then incubated for 8 h with the indicated drug and fixed and permeabilized. Cells were then stained with a polyclonal antibody to PDI to stain the ER (red) or a monoclonal antibody to SV40 (green). Arrows indicate colocalization between virions and PDI. FIG. 10C: Retro-2$^{cycl}$ treatment redistributed JCpyV to early endosomes. Cells were transfected with early endosomal and ER markers (Early endosome (Rab5-RFP) in green; Endoplasmic reticulum (CFP-HO) in blue; JCV in red). In cells treated with Retro-2$^{cycl}$, more virions are seen to colocalize with Rab5 positive enodosomes and less colocalization is seen with the ER.

FIG. 11A: VP2 is exposed at time points late during infection. Cells were pretreated with the indicated drug and then inoculated with JCpyV, BKpyV, or SV40 at an MOI of 10 in the presence of drug prior to incubation for 10 h before fixation and staining for VP2. VP2 punctae and nuceli are indicated with arrows (punctae are also shown in green and nuclei are show in blue). FIG. 11B: VP2 is exposed in the ER. Cells were incubated with JCpyV for 10 h, then fixed and stained for VP1 (green), VP2 (red), PDI (purple), and the nucleus was stained with BOBO-3 (blue). Enlarge portions of the fluorescence micrograph is shown on the right with panels for individual antibody staining FIG. 11C: Quantitation of A. Cells from triplicate samples were scored for the presence of VP2 in these samples.

DEFINITIONS

Chemical Definitions

Figure 1A:
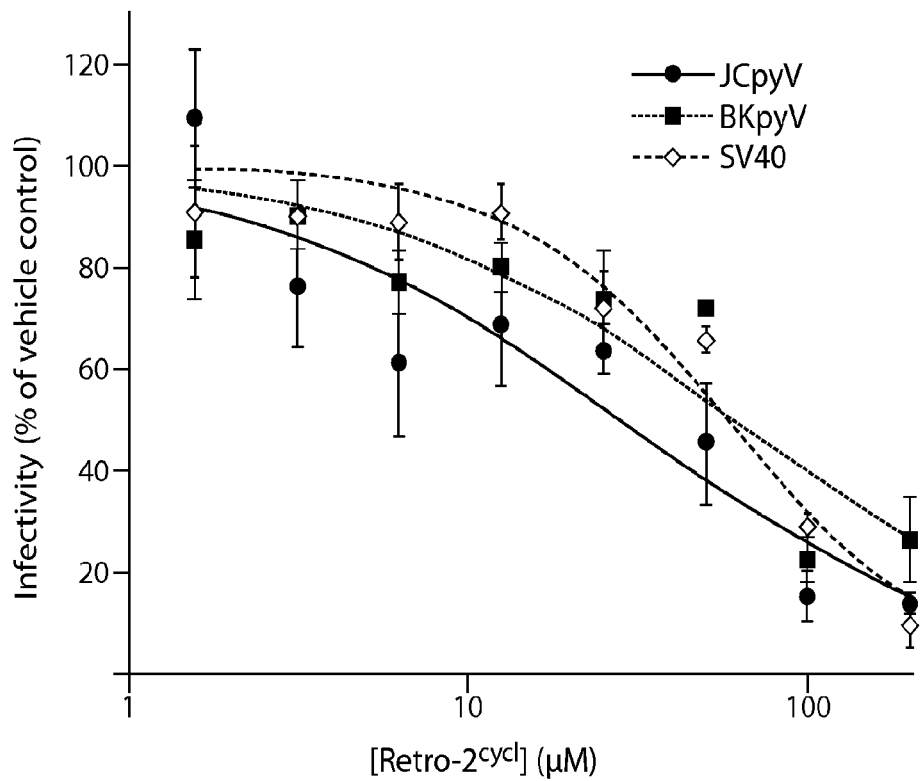
FIGS. 1A-1B depict that Retro-$2^{cycl}$ prevents infectivity of three polyomaviruses.

Definitions of specific functional groups and chemical terms are described in more detail below. The chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, E. L. *Stereochemistry of Carbon Compounds* (McGraw-Hill, NY, 1962); and Wilen, S. H. *Tables of Resolving Agents and Optical Resolutions* p. 268 (E. L. Eliel, Ed., Univ. of Notre Dame Press, Notre Dame, Ind. 1972). The invention additionally encompasses compounds as individual isomers substantially free of other isomers, and alternatively, as mixtures of various isomers.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

As used herein, "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), iso-propyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently unsubstituted (an "unsubstituted alkyl") or substituted (a "substituted alkyl") with one or more substituents. In certain embodiments, the alkyl group is an unsubstituted $C_{1-10}$ alkyl (e.g., —$CH_3$). In certain embodiments, the alkyl group is a substituted $C_{1-10}$ alkyl.

"Perhaloalkyl" is a substituted alkyl group as defined herein wherein all of the hydrogen atoms are independently replaced by a halogen, e.g., fluoro, bromo, chloro, or iodo. In some embodiments, the alkyl moiety has 1 to 8 carbon atoms ("$C_{1-8}$ perhaloalkyl"). In some embodiments, the alkyl moiety has 1 to 6 carbon atoms ("$C_{1-6}$ perhaloalkyl"). In some embodiments, the alkyl moiety has 1 to 4 carbon atoms ("$C_{1-4}$ perhaloalkyl"). In some embodiments, the alkyl moiety has 1 to 3 carbon atoms ("$C_{1-3}$ perhaloalkyl"). In some embodiments, the alkyl moiety has 1 to 2 carbon atoms ("$C_{1-2}$ perhaloalkyl"). In some embodiments, all of the hydrogen atoms are replaced with fluoro. In some embodiments, all of the hydrogen atoms are replaced with chloro. Examples of perhaloalkyl groups include —$CF_3$, —$CF_2CF_3$, —$CF_2CF_2CF_3$, —$CCl_3$, —$CFCl_2$, —$CF_2Cl$, and the like.

As used herein, "alkenyl" refers to a radical of a straight-chain or branched hydrocarbon group having from 2 to 10 carbon atoms and one or more double bonds (e.g., 1, 2, 3, or 4 double bonds) ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted $C_{2-10}$ alkenyl. In certain embodiments, the alkenyl group is a substituted $C_{2-10}$ alkenyl.

As used herein, "alkynyl" refers to a radical of a straight-chain or branched hydrocarbon group having from 2 to 10 carbon atoms and one or more triple bonds (e.g., 1, 2, 3, or 4 triple bonds) ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted $C_{2-10}$ alkynyl. In certain embodiments, the alkynyl group is a substituted $C_{2-10}$ alkynyl.

As used herein, "carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 7 ring carbon atoms ("$C_{3-7}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or polycyclic (e.g., containing a fused, bridged or spiro ring system such as a bicyclic system ("bicyclic carbocyclyl") or tricyclic system ("tricyclic carbocyclyl")) and can be saturated or can contain one or more carbon-carbon double or triple bonds. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted $C_{3-10}$ carbocyclyl. In certain embodiments, the carbocyclyl group is a substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("C$_{5-6}$ cycloalkyl"). In some embodiments, a cycloalkyl group has 5 to 10 ring carbon atoms ("C$_{5-10}$ cycloalkyl"). Examples of C$_{5-6}$ cycloalkyl groups include cyclopentyl (C$_5$) and cyclohexyl (C$_6$). Examples of C$_{3-6}$ cycloalkyl groups include the aforementioned C$_{5-6}$ cycloalkyl groups as well as cyclopropyl (C$_3$) and cyclobutyl (C$_4$). Examples of C$_{3-8}$ cycloalkyl groups include the aforementioned C$_{3-6}$ cycloalkyl groups as well as cycloheptyl (C$_7$) and cyclooctyl (C$_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is an unsubstituted C$_{3-10}$ cycloalkyl. In certain embodiments, the cycloalkyl group is a substituted C$_{3-10}$ cycloalkyl.

As used herein, "heterocyclyl" or "heterocyclic" refers to a radical of a 3- to 14-membered nonaromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon carbon double or triple bonds. Heterocyclyl polycyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered nonaromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered nonaromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered nonaromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include, without limitation, azirdinyl, oxiranyl, thiorenyl. Exemplary 4-membered heterocyclyl groups containing 1 heteroatom include, without limitation, azetidinyl, oxetanyl and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing 2 heteroatoms include, without limitation, dioxolanyl, oxathiolanyl and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, dioxanyl. Exemplary 6-membered heterocyclyl groups containing 2 heteroatoms include, without limitation, triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo-[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

As used herein, "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("C$_{6-14}$ aryl"). In some embodiments, an aryl group has 6 ring carbon atoms ("C$_6$ aryl"; e.g., phenyl). In some embodiments, an aryl group has 10 ring carbon atoms ("C$_{10}$ aryl"; e.g., naphthyl such as 1-naphthyl and 2-naphthyl). In some embodiments, an aryl group has 14 ring carbon atoms ("C$_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted C$_{6-14}$ aryl. In certain embodiments, the aryl group is a substituted C$_{6-14}$ aryl.

"Aralkyl" is a subset of "alkyl" and refers to an alkyl group, as defined herein, substituted by an aryl group, as defined herein, wherein the point of attachment is on the alkyl moiety.

As used herein, "heteroaryl" refers to a radical of a 5-14 membered monocyclic or polycyclic (e.g., bicyclic or tricyclic) 4n+2 aromatic ring system (e.g., having 6, 10, or 14 π electrons shared in a cyclic array) having ring carbon atoms and 1-4 ring heteroatoms provided in the aromatic ring system, wherein each heteroatom is independently selected from nitrogen, oxygen and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-membered heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

"Heteroaralkyl" is a subset of "alkyl" and refers to an alkyl group, as defined herein, substituted by a heteroaryl group, as defined herein, wherein the point of attachment is on the alkyl moiety.

As used herein, the term "partially unsaturated" refers to a ring moiety that includes at least one double or triple bond. The term "partially unsaturated" is intended to encompass rings having multiple sites of unsaturation, but is not intended to include aromatic groups (e.g., aryl or heteroaryl moieties) as herein defined.

As used herein, the term "saturated" refers to a ring moiety that does not contain a double or triple bond, i.e., the ring contains all single bonds.

Affixing the suffix "-ene" to a group indicates the group is a divalent moiety, e.g., alkylene is the divalent moiety of alkyl, alkenylene is the divalent moiety of alkenyl, and alkynylene is the divalent moiety of alkynyl.

Alkyl, alkenyl, alkynyl, carbocyclyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). For purposes of this invention, heteroatoms such as nitrogen, oxygen, and sulfur may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)

$SR^{aa}$, $-SC(=O)SR^{aa}$, $-OC(=O)SR^{aa}$, $-SC(=O)OR^{aa}$, $-SC(=O)R^{aa}$, $-P(=O)_2R^{aa}$, $-OP(=O)_2R^{aa}$, $-P(=O)(R^{aa})_2$, $-OP(=O)(R^{aa})_2$, $-OP(=O)(OR^{cc})_2$, $-P(=O)_2N(R^{bb})_2$, $-OP(=O)_2N(R^{bb})_2$, $-P(=O)(NR^{bb})_2$, $-OP(=O)(NR^{bb})_2$, $-NR^{bb}P(=O)(OR^{cc})_2$, $-NR^{bb}P(=O)(NR^{bb})_2$, $-P(R^{cc})_2$, $-P(R^{cc})_3$, $-OP(R^{cc})_2$, $-OP(R^{cc})_3$, $-B(R^{aa})_2$, $-B(OR^{cc})_2$, $-BR^{aa}(OR^{cc})$, $C_{1-10}$ alkyl, $C_{1-10}$ perhaloalkyl, $C_{2-10}$ alkenyl, $C_{2-10}$ alkynyl, $C_{3-14}$ carbocyclyl, 3-14 membered heterocyclyl, $C_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 $R^{dd}$ groups;

or two geminal hydrogens on a carbon atom are replaced with the group $=O$, $=S$, $=NN(R^{bb})_2$, $=NNR^{bb}C(=O)R^{aa}$, $=NNR^{bb}C(=O)OR^{aa}$, $=NNR^{bb}S(=O)_2R^{aa}$, $=NR^{bb}$, or $=NOR^{cc}$;

each instance of $R^{aa}$ is, independently, selected from $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{bb}$ is, independently, selected from hydrogen, $-OH$, $-OR^{aa}$, $-N(R^{cc})_2$, $-CN$, $-C(=O)R^{aa}$, $-C(=O)N(R^{cc})_2$, $-CO_2R^{aa}$, $-SO_2R^{aa}$, $-C(=NR^{cc})OR^{aa}$, $-C(=NR^{cc})N(R^{cc})_2$, $-SO_2N(R^{cc})_2$, $-SO_2R^{cc}$, $-SO_2OR^{cc}$, $-SOR^{aa}$, $-C(=S)N(R^{cc})_2$, $-C(=O)SR^{cc}$, $-C(=S)SR^{cc}$, $-P(=O)_2R^{aa}$, $-P(=O)(R^{aa})_2$, $-P(=O)_2N(R^{cc})_2$, $-P(=O)(NR^{cc})_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{cc}$ is, independently, selected from hydrogen, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups;

each instance of $R^{dd}$ is, independently, selected from halogen, $-CN$, $-NO_2$, $-N_3$, $-SO_2H$, $-SO_3H$, $-OH$, $-OR^{ee}$, $-ON(R^{ff})_2$, $-N(R^{ff})_2$, $-N(R^{ff})_3^+X^-$, $-N(OR^{ee})R^{ff}$, $-SH$, $-SR^{ee}$, $-SSR^{ee}$, $-C(=O)R^{ee}$, $-CO_2H$, $-CO_2R^{ee}$, $-OC(=O)R^{ee}$, $-OCO_2R^{ee}$, $-C(=O)N(R^{ff})_2$, $-OC(=O)N(R^{ff})_2$, $-NR^{ff}C(=O)R^{ee}$, $-NR^{ff}CO_2R^{ee}$, $-NR^{ff}C(=O)N(R^{ff})_2$, $-C(=NR^{ff})OR^{ee}$, $-OC(=NR^{ff})R^{ee}$, $-OC(=NR^{ff})OR^{ee}$, $-C(=NR^{ff})N(R^{ff})_2$, $-OC(=NR)N(R^{ff})_2$, $-NR^{ff}C(=NR^{ff})N(R^{ff})_2$, $-NR^{ff}SO_2R^{ee}$, $-SO_2N(R^{ff})_2$, $-SO_2R^{ee}$, $-SO_2OR^{ee}$, $-OSO_2R^{ee}$, $-S(=O)R^{ee}$, $-Si(R^{ee})_3$, $-OSi(R^{ee})_3$, $-C(=S)N(R^{ff})_2$, $-C(=O)SR^{ee}$, $-C(=S)SR^{ee}$, $-SC(=S)SR^{ee}$, $-P(=O)_2R^{ee}$, $-P(=O)(R^{ee})_2$, $-OP(=O)(R^{ee})_2$, $-OP(=O)(OR^{ee})_2$, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form $=O$ or $=S$;

each instance of $R^{ee}$ is, independently, selected from $C_{1-6}$ alkyl, $C_1$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_{6-10}$ aryl and 5-10 membered heteroaryl, or two $R^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, $-CN$, $-NO_2$, $-N_3$, $-SO_2H$, $-SO_3H$, $-OH$, $-OC_{1-6}$ alkyl, $-ON(C_{1-6}$ alkyl$)_2$, $-N(C_{1-6}$ alkyl$)_2$, $-N(C_{1-6}$ alkyl$)_3^+X^-$, $-NH(C_{1-6}$ alkyl$)_2^+X^-$, $-NH_2(C_{1-6}$ alkyl$)^+X^-$, $-NH_3^+X^-$, $-N(OC_{1-6}$ alkyl$)(C_{1-6}$ alkyl$)$, $-N(OH)(C_{1-6}$ alkyl$)$, $-NH(OH)$, $-SH$, $-SC_{1-6}$ alkyl, $-SS(C_{1-6}$ alkyl$)$, $-C(=O)(C_{1-6}$ alkyl$)$, $-CO_2H$, $-CO_2(C_{1-6}$ alkyl$)$, $-OC(=O)(C_{1-6}$ alkyl$)$, $-OCO_2(C_{1-6}$ alkyl$)$, $-C(=O)NH_2$, $-C(=O)N(C_{1-6}$ alkyl$)_2$, $-OC(=O)NH(C_{1-6}$ alkyl$)$, $-NHC(=O)(C_{1-6}$ alkyl$)$, $-N(C_{1-6}$ alkyl$)C(=O)(C_{1-6}$ alkyl$)$, $-NHCO_2(C_{1-6}$ alkyl$)$, $-NHC(=O)N(C_{1-6}$ alkyl$)_2$, $-NHC(=O)NH(C_{1-6}$ alkyl$)$, $-NHC(=O)NH_2$, $-C(=NH)O(C_{1-6}$ alkyl$)$, $-OC(=NH)(C_{1-6}$ alkyl$)$, $-OC(=NH)OC_{1-6}$ alkyl, $-C(=NH)N(C_{1-6}$ alkyl$)_2$, $-C(=NH)NH(C_{1-6}$ alkyl$)$, $-C(=NH)NH_2$, $-OC(=NH)N(C_{1-6}$ alkyl$)_2$, $-OC(NH)NH(C_{1-6}$ alkyl$)$, $-OC(NH)NH_2$, $-NHC(NH)N(C_{1-6}$ alkyl$)_2$, $-NHC(=NH)NH_2$, $-NHSO_2(C_{1-6}$ alkyl$)$, $-SO_2N(C_{1-6}$ alkyl$)_2$, $-SO_2NH(C_{1-6}$ alkyl$)$, $-SO_2NH_2$, $-SO_2C_{1-6}$ alkyl, $-SO_2OC_{1-6}$ alkyl, $-OSO_2C_{1-6}$ alkyl, $-SOC_{1-6}$ alkyl, $-Si(C_{1-6}$ alkyl$)_3$, $-OSi(C_{1-6}$ alkyl$)_3$-$C(=S)N(C_{1-6}$ alkyl$)_2$, $C(=S)NH(C_{1-6}$ alkyl$)$, $C(=S)NH_2$, $-C(=O)S(C_{1-6}$ alkyl$)$, $-C(=S)SC_{1-6}$ alkyl, $-SC(=S)SC_{1-6}$ alkyl, $-P(=O)_2(C_{1-6}$ alkyl$)$, $-P(=O)(C_{1-6}$ alkyl$)_2$, $-OP(=O)(C_{1-6}$ alkyl$)_2$, $-OP(=O)(OC_{1-6}$ alkyl$)_2$, $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, 5-10 membered heteroaryl; or two geminal $R^{gg}$ substituents can be joined to form $=O$ or $=S$; wherein $X^-$ is a counterion.

As used herein, the term "hydroxyl" or "hydroxy" refers to the group $-OH$. The term "substituted hydroxyl" or "substituted hydroxyl," by extension, refers to a hydroxyl group wherein the oxygen atom directly attached to the parent molecule is substituted with a group other than hydrogen, and includes groups selected from $-OR^{aa}$, $-ON(R^{bb})_2$, $-OC(=O)SR^{aa}$, $-OC(=O)R^{aa}$, $-OCO_2R^{aa}$, $-OC(=O)N(R^{bb})_2$, $-OC(=NR^{bb})R^{aa}$, $-OC(=NR^{bb})OR^{aa}$, $-OC(=NR^{bb})N(R^{bb})_2$, $-OS(=O)R^{aa}$, $-OSO_2R^{aa}$, $-OSi(R^{aa})_3$, $-OP(R^{cc})_2$, $-OP(R^{cc})_3$, $-OP(=O)_2R^{aa}$, $-OP(=O)(R^{aa})_2$, $-OP(=O)(OR^{cc})_2$, $-OP(=O)_2N(R^{bb})_2$, and $-OP(=O)(NR^{bb})_2$, wherein $R^{aa}$, $R^{bb}$, and $R^{cc}$ are as defined herein.

As used herein, the term "thiol" or "thio" refers to the group $-SH$. The term "substituted thiol" or "substituted thio," by extension, refers to a thiol group wherein the sulfur atom directly attached to the parent molecule is substituted with a group other than hydrogen, and includes groups selected from $-SR^{aa}$, $-S=SR^{cc}$, $-SC(=S)SR^{aa}$, $-SC(=O)SR^{aa}$, $-SC(=O)OR^{aa}$, and $-SC(=O)R^{aa}$, wherein $R^{aa}$ and $R^{cc}$ are as defined herein.

As used herein, the term, "amino" refers to the group $-NH_2$. The term "substituted amino," by extension, refers to a monosubstituted amino, a disubstituted amino, or a trisubstituted amino, as defined herein.

As used herein, the term "monosubstituted amino" refers to an amino group wherein the nitrogen atom directly attached to the parent molecule is substituted with one hydrogen and one group other than hydrogen, and includes groups selected from —NH($R^{bb}$), —NHC(=O)$R^{aa}$, —NHCO$_2R^{aa}$, —NHC(=O)N($R^{bb}$)$_2$, —NHC(=N$R^{bb}$)N($R^{bb}$)$_2$, —NHSO$_2R^{aa}$, —NHP(=O)(O$R^{cc}$)$_2$, and —NHP(=O)(N$R^{bb}$)$_2$, wherein $R^{aa}$, —$R^{bb}$ and $R^{cc}$ are as defined herein, and wherein $R^{bb}$ of the group —NH($R^{bb}$) is not hydrogen.

As used herein, the term "disubstituted amino" refers to an amino group wherein the nitrogen atom directly attached to the parent molecule is substituted with two groups other than hydrogen, and includes groups selected from —N($R^{bb}$)$_2$, —N$R^{bb}$C(=O)$R^{aa}$, —N$R^{bb}$CO$_2R^{aa}$, —N$R^{bb}$C(=O)N($R^{bb}$)$_2$, —N$R^{bb}$C(=N$R^{bb}$)N($R^{bb}$)$_2$, —N$R^{bb}$SO$_2R^{aa}$, —N$R^{bb}$P(=O)(O$R^{cc}$)$_2$, and —N$R^{bb}$P(=O)(N$R^{bb}$)$_2$, wherein $R^{aa}$, $R^{bb}$, and $R^{cc}$ are as defined herein, with the proviso that the nitrogen atom directly attached to the parent molecule is not substituted with hydrogen.

As used herein, the term "trisubstituted amino" refers to an amino group wherein the nitrogen atom directly attached to the parent molecule is substituted with three groups, and includes groups selected from —N($R^{bb}$)$_3$ and —N($R^{bb}$)$_3^+$ $X^-$, wherein $R^{bb}$ and $X^-$ are as defined herein.

As used herein, the term "acyl" refers a group wherein the carbon directly attached to the parent molecule is sp$^2$ hybridized, and is substituted with an oxygen, nitrogen or sulfur atom, e.g., a group selected from ketones (—C(=O)$R^{aa}$), carboxylic acids (—CO$_2$H), aldehydes (—CHO), esters (—CO$_2R^{aa}$, —C(=O)S$R^{aa}$, —C(=S)S$R^{aa}$), amides (—C(=O)N($R^{bb}$)$_2$, —C(=O)N$R^{bb}$SO$_2R^{aa}$, —C(=S)N($R^{bb}$)$_2$), and imines (—C(=N$R^{bb}$)$R^{aa}$, —C(=N$R^{bb}$)O$R^{aa}$, C(=N$R^{bb}$)N($R^{bb}$)$_2$), wherein $R^{aa}$ and $R^{bb}$ are as defined herein.

As used herein, the term "halo" or "halogen" refers to fluorine (fluoro, F), chlorine (chloro, —Cl), bromine (bromo, —Br), or iodine (iodo, —I).

As used herein, a "counterion" is a negatively charged group associated with a positively charged quarternary amine in order to maintain electronic neutrality. Exemplary counterions include halide ions (e.g., F$^-$, Cl$^-$, Br$^-$, I$^-$), NO$_3^-$, ClO$_4^-$, OH$^-$, H$_2$PO$_4^-$, HSO$_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

Nitrogen atoms can be substituted or unsubstituted as valency permits, and include primary, secondary, tertiary, and quarternary nitrogen atoms. Exemplary nitrogen atom substitutents include, but are not limited to, hydrogen, —OH, —O$R^{aa}$, —N($R^{cc}$)$_2$, —CN, —C(=O)$R^{aa}$, —C(=O)N($R^{cc}$)$_2$, —CO$_2R^{aa}$, —SO$_2R^{aa}$, —C(=N$R^{bb}$)$R^{aa}$, —C(=N$R^{cc}$)O$R^{aa}$, —C(=N$R^{cc}$)N($R^{cc}$)$_2$, —SO$_2$N($R^{cc}$)$_2$, —SO$_2R^{cc}$, —SO$_2$O$R^{cc}$, —SO$R^{aa}$, —C(=S)N($R^{cc}$)$_2$, —C(=O)S$R^{cc}$, —C(=S)S$R^{cc}$, —P(=O)$_2R^{aa}$, —P(=O)($R^{aa}$)$_2$, —P(=O)$_2$N($R^{cc}$)$_2$, —P(=O)(N$R^{cc}$)$_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl, or two $R^{cc}$ groups attached to an N atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined above.

In certain embodiments, the substituent present on the nitrogen atom is an nitrogen protecting group (also referred to herein as an "amino protecting group"). Nitrogen protecting groups include, but are not limited to, —OH, —O$R^{aa}$, —N($R^{cc}$)$_2$, —C(=O)$R^{aa}$, —C(=O)N($R^{cc}$)$_2$, —CO$_2R^{aa}$, —SO$_2R^{aa}$, —C(=N$R^{cc}$)$R^{aa}$, —C(=N$R^{cc}$)O$R^{aa}$, —C(=N$R^{cc}$)N($R^{cc}$)$_2$, —SO$_2$N($R^{cc}$)$_2$, —SO$_2R^{cc}$, —SO$_2$O$R^{cc}$, —SO$R^{aa}$, —C(=S)N($R^{cc}$)$_2$, —C(=O)S$R^{cc}$, —C(=S)S$R^{cc}$, $C_{1-10}$ alkyl (e.g., aralkyl, heteroaralkyl), $C_{2-10}$ alkenyl, $C_{2-10}$ alkynyl, $C_{3-10}$ carbocyclyl, 3-14 membered heterocyclyl, $C_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Nitrogen protecting groups are well known in the art and include those described in detail in Protecting Groups in Organic Synthesis, T. W. Greene and P. G. M. Wuts, 3$^{rd}$ edition, John Wiley & Sons, 1999, incorporated herein by reference.

For example, nitrogen protecting groups such as amide groups (e.g., —C(=O)$R^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(=O)O$R^{aa}$) include, but are not limited to, methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10, 10-dioxo-10,10,10,10-tetrahydrothioxanthyl)]methyl carbamate (DBDT-moc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido) ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium) benzyl carbamate, and 2,4,6-trimethylbenzyl carbamate.

Nitrogen protecting groups such as sulfonamide groups (e.g., —S(=O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to herein as an "hydroxyl protecting group"). Oxygen protecting groups include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$, —P(=O)$_2$R$^{aa}$, —P(=O)(R$^{aa}$)$_2$, —P(=O)(OR$^{cc}$)$_2$, —P(=O)$_2$N(R$^{bb}$)$_2$, and —P(=O)(NR$^{bb}$)$_2$, wherein R$^{aa}$, R$^{bb}$, and R$^{cc}$ are as defined herein. Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl) ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxide, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl) methyl, 3-(imidazol-1-yl)bis(4',4"-dimethoxyphenyl) methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), methyl carbonate, 9-fluorenylmethyl carbonate (Fmoc), ethyl carbonate, 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), isobutyl carbonate, vinyl carbonate, allyl carbonate, t-butyl carbonate (BOC), p-nitrophenyl carbonate, benzyl carbonate, p-methoxybenzyl carbonate, 3,4-dimethoxybenzyl carbonate, o-nitrobenzyl carbonate, p-nitrobenzyl carbonate, S-benzyl thiocarbonate, 4-ethoxy-1-napthtyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on an sulfur atom is a sulfur protecting group (also referred to as a "thiol protecting group"). Sulfur protecting groups include, but are not limited to, $-R^{aa}$, $-N(R^{bb})_2$, $-C(=O)SR^{aa}$, $-C(=O)R^{aa}$, $-CO_2R^{aa}$, $-C(=O)N(R^{bb})_2$, $-C(=NR^{bb})R^{aa}$, $-C(=NR^{bb})OR^{aa}$, $-C(=NR^{bb})N(R^{bb})_2$, $-S(=O)R^{aa}$, $-SO_2R^{aa}$, $-Si(R^{aa})_3$, $-P(R^{cc})_2$, $-P(R^{cc})_3$, $-P(=O)_2R^{aa}$, $-P(=O)(R^{aa})_2$, $-P(=O)(OR^{cc})_2$, $-P(=O)_2N(R^{bb})_2$, and $-P(=O)(NR^{bb})_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

These and other exemplary substituents are described in more detail in the Detailed Description, Examples, and claims. The invention is not intended to be limited in any manner by the above exemplary listing of substituents.

Other Definitions

As used herein, the term "salt" or "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describes pharmaceutically acceptable salts in detail in *J. Pharmaceutical Sciences* (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, non-toxic ammonium, quaternary ammonium, and amine cations formed using counterions such as halide, hydroxide, carboxylate, sulfate, phosphate, nitrate, lower alkyl sulfonate, and aryl sulfonate.

As used herein, the term "prodrug" means a compound that can hydrolyze, oxidize, or otherwise react under biological conditions (e.g., in vitro or in vivo enzymatic conditions) to provide a pharmacologically active compound. In certain cases, a prodrug has improved physical and/or delivery properties over the parent compound. Prodrugs are typically designed to enhance pharmacologically, pharmaceutically and/or pharmacokinetically based properties associated with the parent compound. The advantage of a prodrug can lie in its physical properties, such as enhanced water solubility for parenteral administration at physiological pH compared to the parent compound, or it enhances absorption from the digestive tract, or it may enhance drug stability for long-term storage.

"Tautomer" includes two or more interconvertible compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may be catalyzed by acid or base. Exemplary tautomerizations include keto-to-enol; amide-to-imide; lactam-to-lactim; enamine-to-imine; and enamine-to-(a different) enamine tautomerizations.

A "subject" to which administration is contemplated includes, but is not limited to, humans (i.e., a male or female of any age group, e.g., a pediatric subject (e.g, infant, child, adolescent) or adult subject (e.g., young adult, middle-aged adult or senior adult)) and/or other non-human animals, for example mammals (e.g., primates (e.g., cynomolgus monkeys, rhesus monkeys); commercially relevant mammals such as cattle, pigs, horses, sheep, goats, cats, and/or dogs), and/or birds (e.g., commercially relevant birds such as chickens, ducks, geese, and/or turkeys). In certain embodiments, the non-human animal is a mammal. The non-human animal may be a male or female and at any stage of development. A non-human animal may be a transgenic animal.

As used herein, and unless otherwise specified, the terms "treat," "treating" and "treatment" contemplate an action that occurs while a subject is suffering from the specified condition (e.g., a pathogenic infection) which reduces the severity of the condition or retards or slows the progression of the condition ("therapeutic treatment"), and also contemplates an action that occurs before a subject begins to suffer from the specified condition and which inhibits or reduces the severity of the condition ("prophylactic treatment").

In general, the "effective amount" of a compound refers to an amount sufficient to elicit the desired biological response, i.e., treating the condition (e.g., infection). As will be appreciated by those of ordinary skill in this art, the effective amount of a compound of the invention may vary depending on such factors as the desired biological endpoint, the pharmacokinetics of the compound, the disease being treated, the mode of administration, and the age, health, and condition of the subject. For example, the effective amount of a compound with anti-infective activity is the amount that results in a sufficient concentration to kill the pathogen (e.g., virus), or to reduce the infectivity of the pathogen (e.g., virus). An effective amount encompasses therapeutic and prophylactic treatment.

As used herein "infectivity" refers to the degree of pathogenicity of a pathogen (virus) as indicated by case fatality rates and/or the ability of the pathogen (e.g., virus) to invade the tissues of the subject; e.g., the ability of the pathogen (e.g., virus) to cause an infection. To reduce the infectivity refers to a reduction of this pathogenic capacity of the pathogen (e.g., virus).

As used herein, and unless otherwise specified, a "therapeutically effective amount" of a compound is an amount sufficient to provide a therapeutic benefit in the treatment of the condition (e.g., infection) or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms or causes of condition, or enhances the therapeutic efficacy of another therapeutic agent.

As used herein, and unless otherwise specified, a "prophylactically effective amount" of a compound is an amount sufficient to prevent the condition (e.g., infection, e.g., to prevent its recurrence), or one or more symptoms associated with the condition. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

As used herein, use of the phrase "at least one instance" refers to 1, 2, 3, or 4 instances, but also encompasses a range, e.g., for example, from 1 to 4, from 1 to 3, from 1 to 2, from 2 to 4, from 2 to 3, or from 3 to 4 instances, inclusive.

As used herein, a "pure" compound indicates that the isolated compound is substantially free of other compounds (contaminants). "Substantially free" in this context indicates the compound comprises less than 15%, less than 10%, less than 9%, less than 8%, less than 7%, less than 6%, less than 5%, less than 4%, less than 3%, less than 2%, less than 1%, less than 0.5%, less than 0.1%, e.g., less than between about 0.1% to about 10%, of other compounds and/or contaminants as determined analytically, e.g., by NMR spectroscopy. In certain embodiments, compounds of Formula (II) are pure and isolated, alone or present in a pharmaceutical composition, and are substantially free of compounds of Formula (I).

DETAILED DESCRIPTION OF CERTAIN EMBODIMENTS OF THE INVENTION

As generally described herein, the present invention is based on the discovery that the imine 2-(((5-methylthiophen-2-yl)methylene)amino)-N-phenylbenzamide (RETRO-2) and the corresponding cyclized product, 2-(5-methylthiophen-2-yl)-3-phenyl-2,3-dihydroquinazolin-4 (1H)-one (Retro-2$^{cycl}$) are inhibitors of polyomavirus (JCV, BKV, and SV40) infectivity. RETRO-2 rapidly converts to Retro-2$^{cycl}$ in solution, and it is likely that the active compound against polyomavirus infectivity is Retro-2$^{cycl}$. It is envisioned that varying substitution at the 5-position of the thiophenyl ring and/or substitution on one or both of the phenyl rings may lead to other potent inhibitors of polyomaviral infection. It is further envisioned that such compounds may also exhibit good activity against other conditions, e.g., other pathogenic conditions associated with endosomal trafficking or sorting.

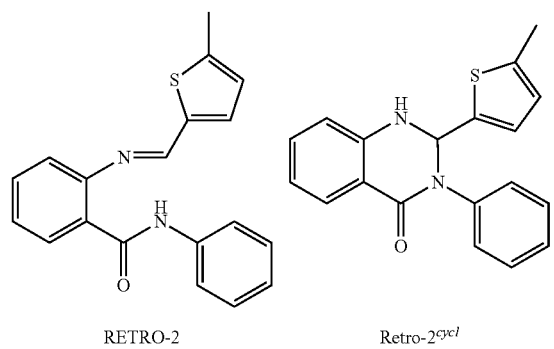 [SMILES: Cc1ccc(/C=N/c2ccccc2C(=O)Nc2ccccc2)s1 ; Cc1ccc(C2Nc3ccccc3C(=O)N2c2ccccc2)s1]

RETRO-2         Retro-2$^{cycl}$

In one aspect, provided are compounds of Formula (I) and (II):

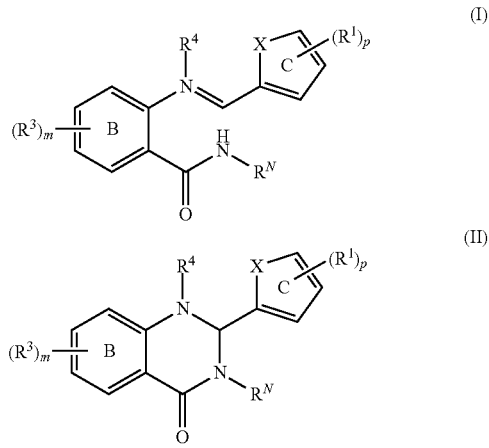

and pharmaceutically acceptable salts, tautomers, prodrugs, and stereoisomers thereof;
wherein:
X is O, S, or NH;
each instance of R$^1$ is independently halo, —NO$_2$, —CN, —SCN, —OR$^{A1}$, —SR$^{A1}$, —N(R$^{A1}$)$_2$, —C(=O)R$^{A1}$, —OC(=O)R$^{A1}$, —SC(=O)R$^{A1}$, —NR$^{A1}$C(=O)R$^{A1}$, —S(=O)$_2$R$^{A1}$, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, and substituted or unsubstituted heteroaryl; each instance of $R^{A1}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, substituted or unsubstituted hydroxyl, substituted or unsubstituted amino, substituted or unsubstituted thiol, an oxygen protecting group when attached to an oxygen atom, a sulfur protecting group when attached to a sulfur atom, or a nitrogen protecting group when attached to a nitrogen atom, or two $R^{A1}$ groups are joined to form a substituted or unsubstituted heterocyclic or heteroaryl ring;

or two $R^1$ groups are joined to form a substituted or unsubstituted aryl, substituted or unsubstituted heteroaryl, substituted or unsubstituted carbocyclic, or substituted or unsubstituted heterocyclic ring;

$R^N$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl;

each instance of $R^3$ is independently halo, $-NO_2$, $-CN$, $-SCN$, $-OR^{A3}$, $-SR^{A3}$, $-N(R^{A3})_2$, $-C(=O)R^{A3}$, $-OC(=O)R^{A3}$, $-SC(=O)R^{A3}$, $-NR^{A3}C(=O)R^{A3}$, $-S(=O)_2R^{A3}$, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, and substituted or unsubstituted heteroaryl, each instance of $R^{A3}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, substituted or unsubstituted hydroxyl, substituted or unsubstituted amino, substituted or unsubstituted thiol, an oxygen protecting group when attached to an oxygen atom, a sulfur protecting group when attached to a sulfur atom, or a nitrogen protecting group when attached to a nitrogen atom, or two $R^{A3}$ groups are joined to form a substituted or unsubstituted heterocyclic or heteroaryl ring;

or two $R^3$ groups are joined to form a substituted or unsubstituted aryl, substituted or unsubstituted heteroaryl, substituted or unsubstituted carbocyclic, or substituted or unsubstituted heterocyclic ring;

$R^4$ is hydrogen, substituted or unsubstituted alkyl, or an nitrogen protecting group;

═ corresponds to a single or double bond;

p is 0, 1, or 2; and m is 0, 1, 2, 3, or 4.

Compounds of Formula (I) and (II) are envisioned useful in the treatment and prevention of a viral infection and/or a pathogenic condition associated with aberrant endosomal trafficking, as further described herein.

Various Embodiments of Compounds of Formula (I) and (II)

As generally defined above for compounds of Formula (I) and (II), X is O, S, or NH. In certain embodiments, X is O. In certain embodiments, X is S. In certain embodiments, X is NH.

As generally defined above for compounds of Formula (I) and (II), each instance of $R^1$ is independently halo, $-NO_2$, $-CN$, $-SCN$, $-OR^{A1}$, $-SR^{A1}$, $-N(R^{A1})_2$, $-C(=O)R^{A1}$, $-OC(=O)R^{A1}$, $-SC(=O)R^{A1}$, $-NR^{A1}C(=O)R^{A1}$, $-S(=O)_2R^{A1}$, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, and substituted or unsubstituted heteroaryl, wherein each instance of $R^{A1}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, substituted or unsubstituted hydroxyl, substituted or unsubstituted amino, substituted or unsubstituted thiol, an oxygen protecting group when attached to an oxygen atom, a sulfur protecting group when attached to a sulfur atom, or a nitrogen protecting group when attached to a nitrogen atom, or two $R^{A1}$ groups are joined to form a substituted or unsubstituted heterocyclic or heteroaryl ring, or two $R^1$ groups are joined to form a substituted or unsubstituted aryl, substituted or unsubstituted heteroaryl, substituted or unsubstituted carbocyclic, or substituted or unsubstituted heterocyclic ring.

In certain embodiments, at least one instance of $R^1$ is halo, e.g., fluoro (—F), chloro (—Cl), bromo (—Br), or iodo (—I).

In certain embodiments, at least one instance of $R^1$ is substituted or unsubstituted alkyl, e.g., substituted or unsubstituted $C_{1-6}$alkyl, substituted or unsubstituted $C_{1-2}$alkyl, substituted or unsubstituted $C_{2-3}$alkyl, substituted or unsubstituted $C_{3-4}$alkyl, substituted or unsubstituted $C_{4-5}$alkyl, substituted or unsubstituted $C_{5-6}$alkyl, substituted or unsubstituted $C_1$alkyl, substituted or unsubstituted $C_2$alkyl, substituted or unsubstituted $C_3$alkyl, substituted or unsubstituted $C_4$alkyl, substituted or unsubstituted $C_5$alkyl, or substituted or unsubstituted $C_6$alkyl. In certain embodiments, $R^1$ is methyl ($C_1$), ethyl ($C_2$), n-propyl ($C_3$), isopropyl ($C_3$), n-butyl ($C_4$), tert-butyl ($C_4$), sec-butyl ($C_4$), isobutyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), or n-hexyl ($C_6$).

In certain embodiments, at least one instance of $R^1$ is substituted or unsubstituted alkenyl, e.g., substituted or unsubstituted $C_{2-6}$alkenyl, substituted or unsubstituted $C_{2-3}$alkenyl, substituted or unsubstituted $C_{3-4}$alkenyl, substituted or unsubstituted $C_{4-5}$alkenyl, substituted or unsubstituted $C_{5-6}$alkenyl, substituted or unsubstituted $C_2$alkenyl, substituted or unsubstituted $C_3$alkenyl, substituted or unsubstituted $C_4$alkenyl, substituted or unsubstituted $C_5$alkenyl, or substituted or unsubstituted $C_6$alkenyl. In certain embodiments, $R^1$ is substituted or unsubstituted allyl ($C_3$).

In certain embodiments, at least one instance of $R^1$ is substituted or unsubstituted alkynyl, e.g., substituted or unsubstituted $C_{2-6}$alkynyl, substituted or unsubstituted $C_{2-3}$alkynyl, substituted or unsubstituted $C_{3-4}$alkynyl, substituted or unsubstituted $C_{4-5}$alkynyl, substituted or unsubstituted $C_{5-6}$alkynyl, substituted or unsubstituted $C_2$alkynyl, substituted or unsubstituted $C_3$alkynyl, substituted or unsubstituted $C_4$alkynyl, substituted or unsubstituted $C_5$alkynyl, or substituted or unsubstituted $C_6$alkynyl. In certain embodiments, $R^1$ is substituted or unsubstituted acetylene ($C_2$) or substituted or unsubstituted propargyl ($C_3$).

In certain embodiments, at least one instance of $R^1$ is substituted or unsubstituted carbocyclyl, e.g., substituted or unsubstituted $C_{3-6}$carbocyclyl, substituted or unsubstituted $C_{3-4}$carbocyclyl, substituted or unsubstituted $C_{4-5}$carbocyclyl, or substituted or unsubstituted $C_{5-6}$carbocyclyl.

In certain embodiments, at least one instance of $R^1$ is substituted or unsubstituted heterocyclyl, e.g., substituted or unsubstituted 3- to 6-membered heterocyclyl, substituted or unsubstituted 3- to 4-membered heterocyclyl, substituted or unsubstituted 4- to 5-membered heterocyclyl, or substituted or unsubstituted 5- to 6-membered heterocyclyl.

In certain embodiments, at least one instance of $R^1$ is substituted or unsubstituted aryl, e.g., substituted or unsubstituted phenyl.

In certain embodiments, at least one instance of $R^1$ is substituted or unsubstituted heteroaryl, e.g., substituted or unsubstituted 5- to 6-membered heteroaryl.

In certain embodiments, at least one instance of $R^1$ is $-NO_2$. In certain embodiments, $R^1$ is $-CN$. In certain embodiments, $R^1$ is $-SCN$.

In certain embodiments, at least one instance of $R^1$ is $-OR^{A1}$, e.g., wherein $R^{A1}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or an oxygen protecting group.

In certain embodiments, at least one instance of $R^1$ is $-SR^{A1}$, e.g., wherein $R^{A1}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a sulfur protecting group.

In certain embodiments, at least one instance of $R^1$ is $-N(R^{A1})_2$, e.g., wherein each instance of $R^{A1}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group, or two $R^{A1}$ groups are joined to form a substituted or unsubstituted heterocyclic or heteroaryl ring.

In certain embodiments, at least one instance of $R^1$ is $-C(=O)R^{A1}$, e.g., wherein $R^{A1}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, substituted or unsubstituted hydroxyl, substituted or unsubstituted amino, or substituted or unsubstituted thiol.

In certain embodiments, at least one instance of $R^1$ is $-OC(=O)R^{A1}$, e.g., wherein $R^{A1}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, substituted or unsubstituted hydroxyl, substituted or unsubstituted amino, or substituted or unsubstituted thiol.

In certain embodiments, at least one instance of $R^1$ is $-SC(=O)R^{A1}$, e.g., wherein $R^{A1}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, substituted or unsubstituted hydroxyl, substituted or unsubstituted amino, or substituted or unsubstituted thiol.

In certain embodiments, at least one instance of $R^1$ is $-NR^{A1}C(=O)R^{A1}$, e.g., wherein $R^{A2}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, substituted or unsubstituted hydroxyl, substituted or unsubstituted amino, or substituted or unsubstituted thiol, or $R^{A1}$ is a nitrogen protecting group when attached to the nitrogen atom.

In certain embodiments, at least one instance of $R^1$ is $-S(=O)_2R^{A1}$, e.g., wherein $R^{A1}$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, substituted or unsubstituted hydroxyl, substituted or unsubstituted amino, or substituted or unsubstituted thiol.

In any of the above described embodiments, in certain instances, $R^{A1}$ is hydrogen.

In any of the above described embodiments, in certain instances, $R^{A1}$ is substituted or unsubstituted alkyl, e.g., substituted or unsubstituted $C_{1-6}$alkyl, substituted or unsubstituted $C_{1-2}$alkyl, substituted or unsubstituted $C_{2-3}$ alkyl, substituted or unsubstituted $C_{3-4}$alkyl, substituted or unsubstituted $C_{4-5}$alkyl, substituted or unsubstituted $C_{5-6}$alkyl, substituted or unsubstituted $C_1$alkyl, substituted or unsubstituted $C_2$alkyl, substituted or unsubstituted $C_3$alkyl, substituted or unsubstituted $C_4$alkyl, substituted or unsubstituted $C_5$alkyl, or substituted or unsubstituted $C_6$alkyl. In certain embodiments, $R^{A1}$ is methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), or n-hexyl ($C_6$).

In any of the above described embodiments, in certain instances, $R^{A1}$ is substituted or unsubstituted alkenyl, e.g., substituted or unsubstituted $C_{2-6}$alkenyl, substituted or unsubstituted $C_{2-3}$alkenyl, substituted or unsubstituted $C_{3-4}$alkenyl, substituted or unsubstituted $C_{4-5}$alkenyl, substituted or unsubstituted $C_{5-6}$alkenyl, substituted or unsubstituted $C_2$alkenyl, substituted or unsubstituted $C_3$alkenyl, substituted or unsubstituted $C_4$alkenyl, substituted or unsubstituted $C_5$alkenyl, or substituted or unsubstituted $C_6$alkenyl. In certain embodiments, $R^{A1}$ is substituted or unsubstituted allyl ($C_3$).

In any of the above described embodiments, in certain instances, $R^{A1}$ is substituted or unsubstituted alkynyl, e.g., substituted or unsubstituted $C_{2-6}$alkynyl, substituted or unsubstituted $C_{2-3}$alkynyl, substituted or unsubstituted $C_{3-4}$alkynyl, substituted or unsubstituted $C_{4-5}$alkynyl, substituted or unsubstituted $C_{5-6}$alkynyl, substituted or unsubstituted $C_2$alkynyl, substituted or unsubstituted $C_3$alkynyl, substituted or unsubstituted $C_4$alkynyl, substituted or unsubstituted $C_5$alkynyl, or substituted or unsubstituted $C_6$alkynyl. In certain embodiments, $R^{A1}$ is substituted or unsubstituted acetylene ($C_2$) or substituted or unsubstituted propargyl ($C_3$).

In any of the above described embodiments, in certain instances, $R^{A1}$ is substituted or unsubstituted carbocyclyl, e.g., substituted or unsubstituted $C_{3-6}$carbocyclyl, substituted or unsubstituted $C_{3-4}$carbocyclyl, substituted or unsubstituted $C_{4-5}$ carbocyclyl, or substituted or unsubstituted $C_{5-6}$ carbocyclyl.

In any of the above described embodiments, in certain instances, $R^{A1}$ is substituted or unsubstituted heterocyclyl, e.g., substituted or unsubstituted 3- to 6-membered heterocyclyl, substituted or unsubstituted 3- to 4-membered heterocyclyl, substituted or unsubstituted 4- to 5-membered heterocyclyl, or substituted or unsubstituted 5- to 6-membered heterocyclyl.

In any of the above described embodiments, in certain instances, $R^{A1}$ is substituted or unsubstituted aryl, e.g., substituted or unsubstituted phenyl.

In any of the above described embodiments, in certain instances, $R^{A1}$ is substituted or unsubstituted heteroaryl, e.g., substituted or unsubstituted 5- to 6-membered heteroaryl.

In any of the above described embodiments, in certain instances, $R^{A1}$ is substituted or unsubstituted hydroxyl, substituted or unsubstituted amino, substituted or unsubstituted thiol, an oxygen protecting group when attached to an oxygen atom, a sulfur protecting group when attached to a sulfur atom, or a nitrogen protecting group when attached to a nitrogen atom.

In any of the above described embodiments, in certain instances, two $R^{A1}$ groups are joined to form a substituted or unsubstituted heterocyclic or heteroaryl ring, e.g., joined to form a substituted or unsubstituted heterocyclic or heteroaryl ring, e.g., substituted or unsubstituted 3- to 6-membered heterocyclyl, substituted or unsubstituted 3- to 4-membered heterocyclyl, substituted or unsubstituted 4- to 5-membered heterocyclyl, or substituted or unsubstituted 5- to 6-membered heterocyclyl, or an substituted or unsubstituted 5- to 6-membered heteroaryl.

In certain embodiments, two $R^1$ groups are joined to form a substituted or unsubstituted aryl, substituted or unsubstituted heteroaryl, substituted or unsubstituted carbocyclic, or substituted or unsubstituted heterocyclic ring. Thus, for example, in any of the embodiments described herein, wherein p is 2, two $R^1$ groups vicinal to each other may be joined to form a substituted or unsubstituted aryl, substituted or unsubstituted heteroaryl, substituted or unsubstituted carbocyclic, or substituted or unsubstituted heterocyclic ring. Various bicyclic Ring C systems are contemplated from the joining of two vicinal $R^1$ groups.

In certain embodiments, two $R^1$ groups are joined to form a substituted or unsubstituted carbocyclyl, e.g., substituted or unsubstituted $C_{3-6}$carbocyclyl, substituted or unsubstituted $C_{3-4}$carbocyclyl, substituted or unsubstituted $C_{4-5}$ carbocyclyl, or substituted or unsubstituted $C_{5-6}$ carbocyclyl.

In certain embodiments, two $R^1$ groups are joined to form a substituted or unsubstituted heterocyclyl, e.g., substituted or unsubstituted 3- to 6-membered heterocyclyl, substituted or unsubstituted 3- to 4-membered heterocyclyl, substituted or unsubstituted 4- to 5-membered heterocyclyl, or substituted or unsubstituted 5- to 6-membered heterocyclyl.

In certain embodiments, two $R^1$ groups are joined to form a substituted or unsubstituted aryl, e.g., substituted or unsubstituted phenyl.

In certain embodiments, two $R^1$ groups are joined to form a substituted or unsubstituted heteroaryl, e.g., substituted or unsubstituted 5- to 6-membered heteroaryl.

As generally defined above for compounds of Formula (I) and (II), p is 0, 1, or 2, and refers to the number of substituents (or lack of substituents when p is 0) attached to Ring C:

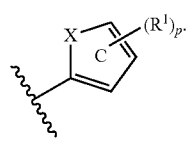

In certain embodiments, p is 0, and Ring C is an unsubstituted ring of the formula:

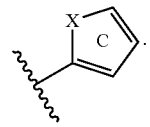

In certain embodiments, p is 1, and Ring C is a monosubstituted ring, e.g., of the formula:

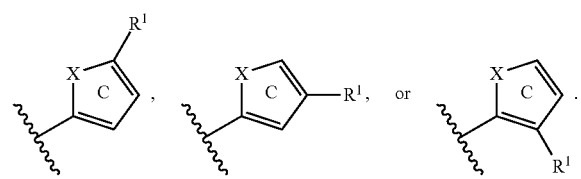

In certain embodiments, p is 2, and Ring C is a disubstituted ring, e.g., of the formula:

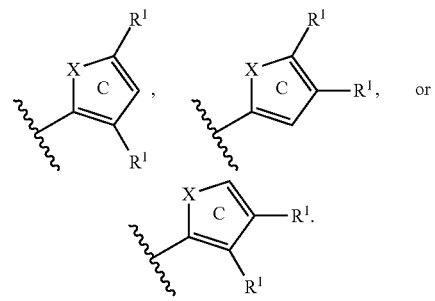

As generally defined above for compounds of Formula (I) and (II), $R^N$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl.

In certain embodiments, $R^N$ is hydrogen.

In certain embodiments, $R^N$ is substituted or unsubstituted alkyl, e.g., substituted or unsubstituted $C_{1-6}$alkyl, substituted or unsubstituted $C_{1-2}$alkyl, substituted or unsubstituted $C_{2-3}$alkyl, substituted or unsubstituted $C_{3-4}$alkyl, substituted or unsubstituted $C_{4-5}$alkyl, substituted or unsubstituted $C_{5-6}$alkyl, substituted or unsubstituted $C_1$alkyl, substituted or unsubstituted $C_2$alkyl, substituted or unsubstituted $C_3$alkyl, substituted or unsubstituted $C_4$alkyl, substituted or unsubstituted $C_5$alkyl, or substituted or unsubstituted $C_6$alkyl. In certain embodiments, $R^N$ is methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), or n-hexyl ($C_6$).

In certain embodiments, $R^N$ is substituted or unsubstituted alkenyl, e.g., substituted or unsubstituted $C_{2-6}$alkenyl, substituted or unsubstituted $C_{2-3}$alkenyl, substituted or unsubstituted $C_{3-4}$alkenyl, substituted or unsubstituted $C_{4-5}$alkenyl, substituted or unsubstituted $C_{5-6}$ alkenyl, substituted or unsubstituted $C_2$alkenyl, substituted or unsubstituted $C_3$alkenyl, substituted or unsubstituted $C_4$alkenyl, substituted or unsubstituted C$_5$alkenyl, or substituted or unsubstituted C$_6$alkenyl. In certain embodiments, R$^N$ is substituted or unsubstituted allyl (C$_3$).

In certain embodiments, R$^N$ is substituted or unsubstituted alkynyl, e.g., substituted or unsubstituted C$_{2-6}$alkynyl, substituted or unsubstituted C$_{2-3}$alkynyl, substituted or unsubstituted C$_{3-4}$alkynyl, substituted or unsubstituted C$_{4-5}$alkynyl, substituted or unsubstituted C$_{5-6}$alkynyl, substituted or unsubstituted C$_2$alkynyl, substituted or unsubstituted C$_3$alkynyl, substituted or unsubstituted C$_4$alkynyl, substituted or unsubstituted C$_5$alkynyl, or substituted or unsubstituted C$_6$alkynyl. In certain embodiments, R$^N$ is substituted or unsubstituted acetylene (C$_2$) or substituted or unsubstituted propargyl (C$_3$).

In certain embodiments, R$^N$ is substituted or unsubstituted carbocyclyl, e.g., substituted or unsubstituted C$_{3-6}$carbocyclyl, substituted or unsubstituted C$_{3-4}$carbocyclyl, substituted or unsubstituted C$_{4-5}$ carbocyclyl, or substituted or unsubstituted C$_{5-6}$ carbocyclyl.

In certain embodiments, R$^N$ is substituted or unsubstituted heterocyclyl, e.g., substituted or unsubstituted 3- to 6-membered heterocyclyl, substituted or unsubstituted 3- to 4-membered heterocyclyl, substituted or unsubstituted 4- to 5-membered heterocyclyl, or substituted or unsubstituted 5- to 6-membered heterocyclyl.

In certain embodiments, R$^N$ is substituted or unsubstituted aryl, e.g., substituted or unsubstituted phenyl.

In certain embodiments, R$^N$ is substituted or unsubstituted heteroaryl, e.g., substituted or unsubstituted 5- to 6-membered heteroaryl.

In certain specific embodiments, wherein R$^N$ is a substituted alkyl, substituted alkenyl, substituted alkynyl, or substituted aryl group, R$^N$ comprises Ring A directly attached to the parent moiety (wherein L$^1$ is a bond) or attached via a linker group (wherein L$^1$ is substituted or unsubstituted alkylene, substituted or unsubstituted alkenylene, or substituted or unsubstituted alkynylene):

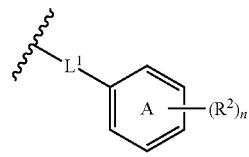

each instance of R$^2$ is independently halo, —NO$_2$, —CN, —SCN, —OR$^{A2}$, —SR$^{A2}$, —N(R$^{A2}$)$_2$, —C(=O)R$^{A2}$, —OC(=O)R$^{A2}$, —SC(=O)R$^{A2}$, —NR$^{A2}$C(=O)R$^{A2}$, —S(=O)$_2$R$^{A2}$, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, and substituted or unsubstituted heteroaryl, each instance of R$^{A2}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, substituted or unsubstituted hydroxyl, substituted or unsubstituted amino, substituted or unsubstituted thiol, an oxygen protecting group when attached to an oxygen atom, a sulfur protecting group when attached to a sulfur atom, or a nitrogen protecting group when attached to a nitrogen atom, or two R$^{A2}$ groups are joined to form a substituted or unsubstituted heterocyclic or heteroaryl ring;

or two R$^2$ groups are joined to form a substituted or unsubstituted aryl, substituted or unsubstituted heteroaryl, substituted or unsubstituted carbocyclic, or substituted or unsubstituted heterocyclic ring; and n is 0, 1, 2, 3, 4 or 5.

It is understood that for such compounds comprising Ring A, n refers to the number of substituents (or lack of substituents when n is 0) attached to Ring A:

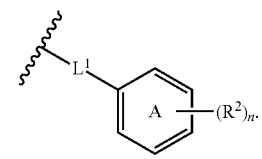

In certain embodiments, n is 0, and Ring A is an unsubstituted ring of the formula:

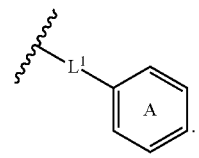

In certain embodiments, n is 1, and Ring A is a monosubstituted ring, e.g., of the formula:

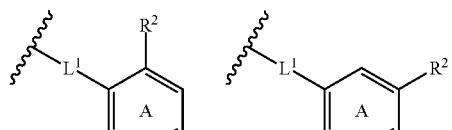

ortho            meta

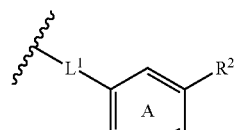

para

In certain embodiments, n is 2, and Ring A is a disubstituted ring, e.g., of the formula:

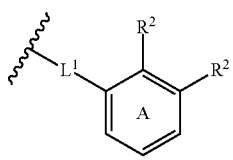 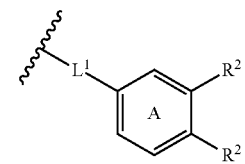

2,3              3,4

-continued

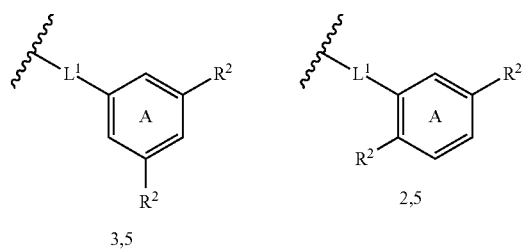

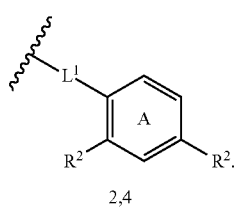

In certain embodiments, n is 3, and Ring A is a trisubstituted ring, e.g., of the formula:

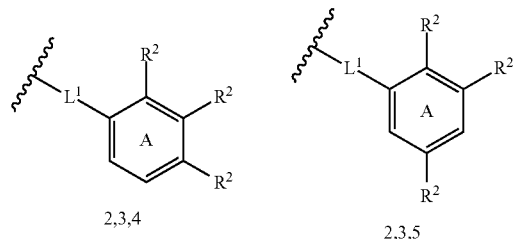

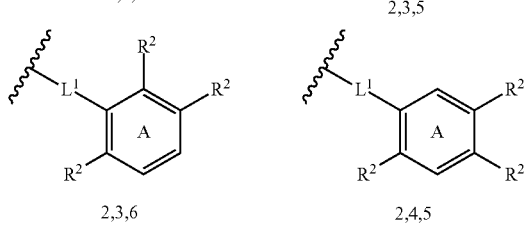

In certain embodiments, n is 4, and Ring A is a tetrasubstituted ring, e.g., of the formula:

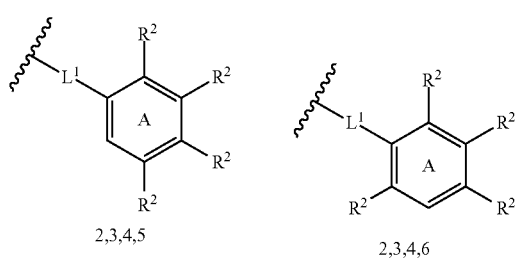

-continued

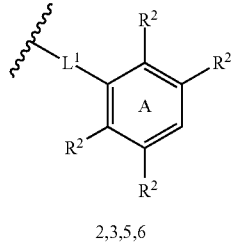

In certain embodiments, n is 5, and Ring A is a pentasubstituted ring of the formula:

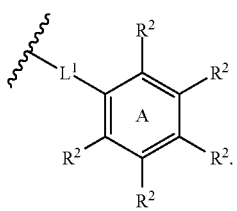

In certain embodiments, at least one instance of $R^2$ is halo, e.g., fluoro (—F), chloro (—Cl), bromo (—Br), or iodo (—I).

In certain embodiments, $L^1$ is a bond.

In certain embodiments, $L^1$ is substituted or unsubstituted alkylene, e.g., substituted or unsubstituted $C_{1-6}$alkylene, substituted or unsubstituted $C_{1-2}$alkylene, substituted or unsubstituted $C_{1-3}$alkylene, substituted or unsubstituted $C_{2-3}$alkylene, substituted or unsubstituted $C_{3-4}$alkylene, substituted or unsubstituted $C_{4-5}$alkylene, substituted or unsubstituted $C_{5-6}$alkylene, substituted or unsubstituted $C_1$alkylene, substituted or unsubstituted $C_2$alkylene, substituted or unsubstituted $C_3$alkylene, substituted or unsubstituted $C_4$alkylene, substituted or unsubstituted $C_5$alkylene, or substituted or unsubstituted $C_6$alkylene. In certain embodiments, $L^1$ is methylene ($C_1$), ethylene ($C_2$), n-propylene ($C_3$), n-butylene ($C_4$), n-pentylene ($C_5$), or n-hexylene ($C_6$). In certain embodiments, $L^1$ is —CH(CH$_3$)— having (R) or (S) stereochemistry.

In certain embodiments, $L^1$ is substituted or unsubstituted alkenylene, e.g., substituted or unsubstituted $C_{2-6}$alkenylene, substituted or unsubstituted $C_{2-3}$alkenylene, substituted or unsubstituted $C_{3-4}$alkenylene, substituted or unsubstituted $C_{4-5}$alkenylene, substituted or unsubstituted $C_{5-6}$alkenylene, substituted or unsubstituted $C_2$alkenylene, substituted or unsubstituted $C_3$alkenylene, substituted or unsubstituted $C_4$alkenylene, substituted or unsubstituted $C_5$alkenylene, or substituted or unsubstituted $C_6$alkenylene.

In certain embodiments, L is substituted or unsubstituted alkynylene, e.g., substituted or unsubstituted $C_{2-6}$alkynylene, substituted or unsubstituted $C_{2-3}$alkynylene, substituted or unsubstituted $C_{3-4}$alkynylene, substituted or unsubstituted $C_{4-5}$alkynylene, substituted or unsubstituted $C_{5-6}$alkynylene, substituted or unsubstituted $C_2$alkynylene, substituted or unsubstituted $C_3$alkynylene, substituted or unsubstituted $C_4$alkynylene, substituted or unsubstituted $C_5$alkynylene, or substituted or unsubstituted $C_6$alkynylene.

In certain embodiments, at least one instance of $R^2$ is substituted or unsubstituted alkyl, e.g., substituted or unsubstituted $C_{1-6}$alkyl, substituted or unsubstituted $C_{1-2}$alkyl, substituted or unsubstituted $C_{2-3}$ alkyl, substituted or unsubstituted $C_{3-4}$alkyl, substituted or unsubstituted $C_{4-5}$alkyl, substituted or unsubstituted $C_{5-6}$alkyl, substituted or unsubstituted $C_1$alkyl, substituted or unsubstituted $C_2$alkyl, substituted or unsubstituted $C_3$alkyl, substituted or unsubstituted $C_4$alkyl, substituted or unsubstituted $C_5$alkyl, or substituted or unsubstituted $C_6$alkyl. In certain embodiments, $R^2$ is methyl ($C_1$), ethyl ($C_2$), n-propyl ($C_3$), isopropyl ($C_3$), n-butyl ($C_4$), tert-butyl ($C_4$), sec-butyl ($C_4$), isobutyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), or n-hexyl ($C_6$).

In certain embodiments, at least one instance of $R^2$ is substituted or unsubstituted alkenyl, e.g., substituted or unsubstituted $C_{2-6}$alkenyl, substituted or unsubstituted $C_{2-3}$alkenyl, substituted or unsubstituted $C_{3-4}$alkenyl, substituted or unsubstituted $C_{4-5}$alkenyl, substituted or unsubstituted $C_{5-6}$alkenyl, substituted or unsubstituted $C_2$alkenyl, substituted or unsubstituted $C_3$alkenyl, substituted or unsubstituted $C_4$alkenyl, substituted or unsubstituted $C_5$alkenyl, or substituted or unsubstituted $C_6$alkenyl. In certain embodiments, $R^2$ is substituted or unsubstituted allyl ($C_3$).

In certain embodiments, at least one instance of $R^2$ is substituted or unsubstituted alkynyl, e.g., substituted or unsubstituted $C_{2-6}$alkynyl, substituted or unsubstituted $C_{2-3}$alkynyl, substituted or unsubstituted $C_{3-4}$alkynyl, substituted or unsubstituted $C_{4-5}$alkynyl, substituted or unsubstituted $C_{5-6}$alkynyl, substituted or unsubstituted $C_2$alkynyl, substituted or unsubstituted $C_3$alkynyl, substituted or unsubstituted $C_4$alkynyl, substituted or unsubstituted $C_5$alkynyl, or substituted or unsubstituted $C_6$alkynyl. In certain embodiments, $R^2$ is substituted or unsubstituted acetylene ($C_2$) or substituted or unsubstituted propargyl ($C_3$).

In certain embodiments, at least one instance of $R^2$ is substituted or unsubstituted carbocyclyl, e.g., substituted or unsubstituted $C_{3-6}$carbocyclyl, substituted or unsubstituted $C_{3-4}$carbocyclyl, substituted or unsubstituted $C_{4-5}$ carbocyclyl, or substituted or unsubstituted $C_{5-6}$ carbocyclyl.

In certain embodiments, at least one instance of $R^2$ is substituted or unsubstituted heterocyclyl, e.g., substituted or unsubstituted 3- to 6-membered heterocyclyl, substituted or unsubstituted 3- to 4-membered heterocyclyl, substituted or unsubstituted 4- to 5-membered heterocyclyl, or substituted or unsubstituted 5- to 6-membered heterocyclyl.

In certain embodiments, at least one instance of $R^2$ is substituted or unsubstituted aryl, e.g., substituted or unsubstituted phenyl.

In certain embodiments, at least one instance of $R^2$ is substituted or unsubstituted heteroaryl, e.g., substituted or unsubstituted 5- to 6-membered heteroaryl.

In certain embodiments, at least one instance of $R^2$ is $-NO_2$. In certain embodiments, at least one instance of $R^2$ is $-CN$. In certain embodiments, at least one instance of $R^2$ is $-SCN$.

In certain embodiments, at least one instance of $R^2$ is $-OR^{A2}$, e.g., wherein $R^{A2}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or an oxygen protecting group. In certain embodiments, R2 is $-OR^{A2}$ wherein $R^{A2}$ is substituted or unsubstituted alkyl.

In certain embodiments, at least one instance of $R^2$ is $-SR^{A2}$, e.g., wherein $R^{A2}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a sulfur protecting group.

In certain embodiments, at least one instance of $R^2$ is $-N(R^{A2})_2$, e.g., wherein each instance of $R^{A2}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group, or two $R^{A2}$ groups are joined to form a substituted or unsubstituted heterocyclic or heteroaryl ring.

In certain embodiments, at least one instance of $R^2$ is $-C(=O)R^{A2}$, e.g., wherein $R^{A2}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, substituted or unsubstituted hydroxyl, substituted or unsubstituted amino, or substituted or unsubstituted thiol.

In certain embodiments, at least one instance of $R^2$ is $-OC(=O)R^{A2}$, e.g., wherein $R^{A2}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, substituted or unsubstituted hydroxyl, substituted or unsubstituted amino, or substituted or unsubstituted thiol.

In certain embodiments, at least one instance of $R^2$ is $-SC(=O)R^{A2}$, e.g., wherein $R^{A2}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, substituted or unsubstituted hydroxyl, substituted or unsubstituted amino, or substituted or unsubstituted thiol.

In certain embodiments, at least one instance of $R^2$ is $-NR^{A2}C(=O)R^{A2}$, e.g., wherein $R^{A2}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, substituted or unsubstituted hydroxyl, substituted or unsubstituted amino, substituted or unsubstituted thiol, or $R^{A2}$ is a nitrogen protecting group when attached to the nitrogen atom.

In certain embodiments, at least one instance of $R^2$ is $-S(=O)_2R^{A2}$, e.g., wherein $R^{A2}$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, substituted or unsubstituted hydroxyl, substituted or unsubstituted amino, or substituted or unsubstituted thiol.

In any of the above described embodiments, in certain instances, $R^{A2}$ is hydrogen.

In any of the above described embodiments, in certain instances, $R^{A2}$ is substituted or unsubstituted alkyl, e.g., substituted or unsubstituted $C_{1-6}$alkyl, substituted or unsubstituted $C_{1-2}$alkyl, substituted or unsubstituted $C_{2-3}$ alkyl, substituted or unsubstituted $C_{3-4}$alkyl, substituted or unsubstituted $C_{4-5}$alkyl, substituted or unsubstituted $C_{5-6}$alkyl, substituted or unsubstituted $C_1$alkyl, substituted or unsubstituted $C_2$alkyl, substituted or unsubstituted $C_3$alkyl, substituted or unsubstituted $C_4$alkyl, substituted or unsubstituted C$_5$alkyl, or substituted or unsubstituted C$_6$alkyl. In certain embodiments, R$^{A2}$ is methyl (C$_1$), ethyl (C$_2$), n-propyl (C$_3$), isopropyl (C$_3$), n-butyl (C$_4$), tert-butyl (C$_4$), sec-butyl (C$_4$), iso-butyl (C$_4$), n-pentyl (C$_5$), 3-pentanyl (C$_5$), amyl (C$_5$), neopentyl (C$_5$), 3-methyl-2-butanyl (C$_5$), tertiary amyl (C$_5$), or n-hexyl (C$_6$).

In any of the above described embodiments, in certain instances, R$^{A2}$ is substituted or unsubstituted alkenyl, e.g., substituted or unsubstituted C$_{2-6}$alkenyl, substituted or unsubstituted C$_{2-3}$alkenyl, substituted or unsubstituted C$_{3-4}$alkenyl, substituted or unsubstituted C$_{4-5}$alkenyl, substituted or unsubstituted C$_{5-6}$alkenyl, substituted or unsubstituted C$_2$alkenyl, substituted or unsubstituted C$_3$alkenyl, substituted or unsubstituted C$_4$alkenyl, substituted or unsubstituted C$_5$alkenyl, or substituted or unsubstituted C$_6$alkenyl. In certain embodiments, R$^{A2}$ is substituted or unsubstituted allyl (C$_3$).

In any of the above described embodiments, in certain instances, R$^{A2}$ is substituted or unsubstituted alkynyl, e.g., substituted or unsubstituted C$_{2-6}$alkynyl, substituted or unsubstituted C$_{2-3}$alkynyl, substituted or unsubstituted C$_{3-4}$alkynyl, substituted or unsubstituted C$_{4-5}$alkynyl, substituted or unsubstituted C$_{5-6}$alkynyl, substituted or unsubstituted C$_2$alkynyl, substituted or unsubstituted C$_3$alkynyl, substituted or unsubstituted C$_4$alkynyl, substituted or unsubstituted C$_5$alkynyl, or substituted or unsubstituted C$_6$alkynyl. In certain embodiments, R$^{A2}$ is substituted or unsubstituted acetylene (C$_2$) or substituted or unsubstituted propargyl (C$_3$).

In any of the above described embodiments, in certain instances, R$^{A2}$ is substituted or unsubstituted carbocyclyl, e.g., substituted or unsubstituted C$_{3-6}$carbocyclyl, substituted or unsubstituted C$_{3-4}$carbocyclyl, substituted or unsubstituted C$_{4-5}$ carbocyclyl, or substituted or unsubstituted C$_{5-6}$ carbocyclyl.

In any of the above described embodiments, in certain instances, R$^{A2}$ is substituted or unsubstituted heterocyclyl, e.g., substituted or unsubstituted 3- to 6-membered heterocyclyl, substituted or unsubstituted 3- to 4-membered heterocyclyl, substituted or unsubstituted 4- to 5-membered heterocyclyl, or substituted or unsubstituted 5- to 6-membered heterocyclyl.

In any of the above described embodiments, in certain instances, R$^{A2}$ is substituted or unsubstituted aryl, e.g., substituted or unsubstituted phenyl.

In any of the above described embodiments, in certain instances, R$^{A2}$ is substituted or unsubstituted heteroaryl, e.g., substituted or unsubstituted 5- to 6-membered heteroaryl.

In any of the above described embodiments, in certain instances, R$^{A2}$ is substituted or unsubstituted hydroxyl, substituted or unsubstituted amino, substituted or unsubstituted thiol, an oxygen protecting group when attached to an oxygen atom, a sulfur protecting group when attached to a sulfur atom, or a nitrogen protecting group when attached to a nitrogen atom.

In any of the above described embodiments, in certain instances, two R$^{A2}$ groups are joined to form a substituted or unsubstituted heterocyclic or heteroaryl ring, e.g., substituted or unsubstituted 3- to 6-membered heterocyclyl, substituted or unsubstituted 3- to 4-membered heterocyclyl, substituted or unsubstituted 4- to 5-membered heterocyclyl, or substituted or unsubstituted 5- to 6-membered heterocyclyl, or an substituted or unsubstituted 5- to 6-membered heteroaryl.

In certain embodiments, two R$^2$ groups are joined to form a substituted or unsubstituted aryl, substituted or unsubstituted heteroaryl, substituted or unsubstituted carbocyclic, or substituted or unsubstituted heterocyclic ring. Thus, for example, in any of the embodiments described herein, wherein n is 2, two R$^2$ groups vicinal to each other may be joined to form a substituted or unsubstituted aryl, substituted or unsubstituted heteroaryl, substituted or unsubstituted carbocyclic, or substituted or unsubstituted heterocyclic ring. Various bicyclic Ring A systems are contemplated from the joining of two vicinal R$^2$ groups.

In certain embodiments, two R$^2$ groups are joined to form a substituted or unsubstituted carbocyclyl, e.g., substituted or unsubstituted C$_{3-6}$carbocyclyl, substituted or unsubstituted C$_{3-4}$carbocyclyl, substituted or unsubstituted C$_{4-5}$ carbocyclyl, or substituted or unsubstituted C$_{5-6}$ carbocyclyl.

In certain embodiments, two R$^2$ groups are joined to form a substituted or unsubstituted heterocyclyl, e.g., substituted or unsubstituted 3- to 6-membered heterocyclyl, substituted or unsubstituted 3- to 4-membered heterocyclyl, substituted or unsubstituted 4- to 5-membered heterocyclyl, or substituted or unsubstituted 5- to 6-membered heterocyclyl.

In certain embodiments, two R$^2$ groups are joined to form a substituted or unsubstituted aryl, e.g., substituted or unsubstituted phenyl.

In certain embodiments, two R$^2$ groups are joined to form a substituted or unsubstituted heteroaryl, e.g., substituted or unsubstituted 5- to 6-membered heteroaryl.

As generally defined above for compounds of Formula (I) and (II), m is 0, 1, 2, 3, or 4, and refers to the number of substituents (or lack of substituents when m is 0) attached to Ring B:

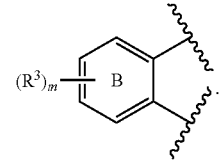

In certain embodiments, m is 0, and Ring B is unsubstituted, e.g., to provide a Ring B of the formula:

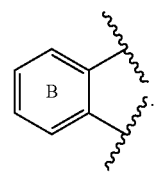

In certain embodiments, m is 1, and Ring B is monosubstituted, e.g., to provide a Ring B of the formula:

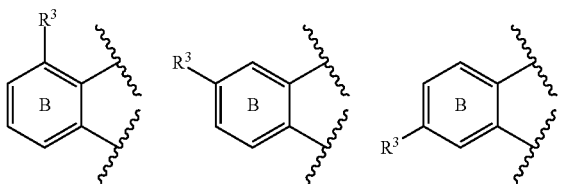

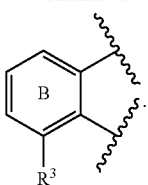

In certain embodiments, m is 2, and Ring B is disubstituted, e.g., to provide a Ring B of the formula:

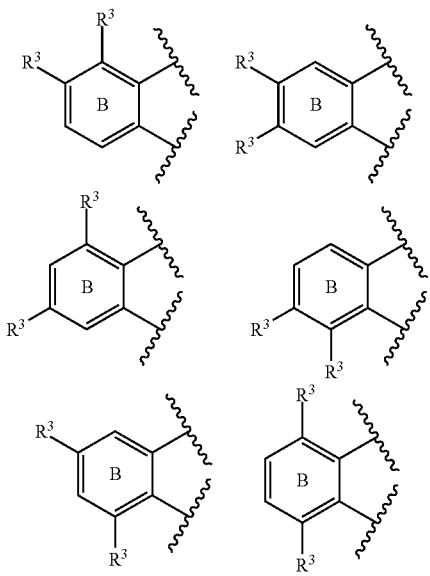

In certain embodiments, m is 3, and Ring B is trisubstituted, e.g., to provide a Ring B of the formula:

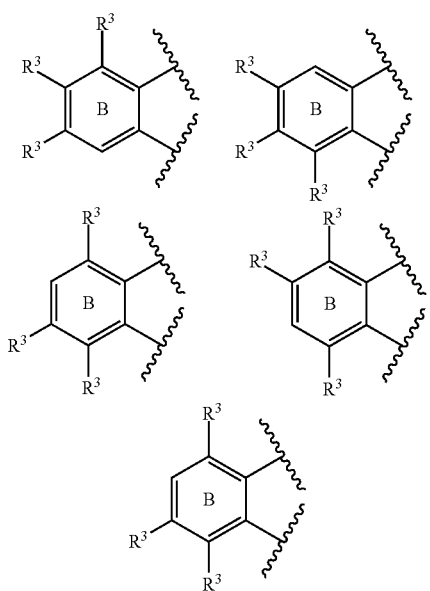

In certain embodiments, m is 4, and Ring B is tetrasubstituted, e.g., to provide a Ring B of the formula:

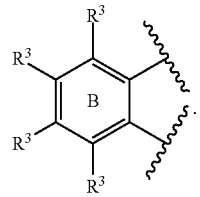

As generally defined above for compounds of Formula (I) and (II), each instance of $R^3$ is independently halo, $-NO_2$, $-CN$, $-SCN$, $-OR^{43}$, $-SR$, $-N(R^{43})_2$, $-C(=O)R^{43}$, $-OC(=O)R^{43}$, $-SC(=O)R^{43}$, $-NR^{43}C(=O)R^{43}$, $-S(=O)_2R^{43}$, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, and substituted or unsubstituted heteroaryl, wherein each instance of $R^{43}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, substituted or unsubstituted hydroxyl, substituted or unsubstituted amino, substituted or unsubstituted thiol, an oxygen protecting group when attached to an oxygen atom, a sulfur protecting group when attached to a sulfur atom, or a nitrogen protecting group when attached to a nitrogen atom, or two $R^{43}$ groups are joined to form a substituted or unsubstituted heterocyclic or heteroaryl ring; or two $R^3$ groups are joined to form a substituted or unsubstituted aryl, substituted or unsubstituted heteroaryl, substituted or unsubstituted carbocyclic, or substituted or unsubstituted heterocyclic ring; and wherein m is 0, 1, 2, 3, or 4.

In certain embodiments, at least one instance of $R^3$ is halo, e.g., fluoro (—F), chloro (—Cl), bromo (—Br), or iodo (—I).

In certain embodiments, at least one instance of $R^3$ is substituted or unsubstituted alkyl, e.g., substituted or unsubstituted $C_{1-6}$alkyl, substituted or unsubstituted $C_{1-2}$alkyl, substituted or unsubstituted $C_{2-3}$ alkyl, substituted or unsubstituted $C_{3-4}$alkyl, substituted or unsubstituted $C_{4-5}$alkyl, substituted or unsubstituted $C_{5-6}$alkyl, substituted or unsubstituted $C_1$alkyl, substituted or unsubstituted $C_2$alkyl, substituted or unsubstituted $C_3$alkyl, substituted or unsubstituted $C_4$alkyl, substituted or unsubstituted $C_5$alkyl, or substituted or unsubstituted $C_6$alkyl. In certain embodiments, $R^3$ is methyl ($C_1$), ethyl ($C_2$), n-propyl ($C_3$), isopropyl ($C_3$), n-butyl ($C_4$), tert-butyl ($C_4$), sec-butyl ($C_4$), isobutyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), or n-hexyl ($C_6$).

In certain embodiments, at least one instance of $R^3$ is substituted or unsubstituted alkenyl, e.g., substituted or unsubstituted $C_{2-6}$alkenyl, substituted or unsubstituted $C_{2-3}$alkenyl, substituted or unsubstituted $C_{3-4}$alkenyl, substituted or unsubstituted $C_{4-5}$alkenyl, substituted or unsubstituted $C_{5-6}$alkenyl, substituted or unsubstituted $C_2$alkenyl, substituted or unsubstituted $C_3$alkenyl, substituted or unsubstituted $C_4$alkenyl, substituted or unsubstituted $C_5$alkenyl, or substituted or unsubstituted $C_6$alkenyl. In certain embodiments, $R^3$ is substituted or unsubstituted allyl ($C_3$).

In certain embodiments, at least one instance of $R^3$ is substituted or unsubstituted alkynyl, e.g., substituted or unsubstituted $C_{2-6}$alkynyl, substituted or unsubstituted $C_{2-3}$alkynyl, substituted or unsubstituted $C_{3-4}$alkynyl, substituted or unsubstituted $C_{4-5}$alkynyl, substituted or unsubstituted $C_{5-6}$alkynyl, substituted or unsubstituted $C_2$alkynyl, substituted or unsubstituted $C_3$alkynyl, substituted or unsubstituted $C_4$alkynyl, substituted or unsubstituted $C_5$alkynyl, or substituted or unsubstituted $C_6$alkynyl. In certain embodiments, $R^3$ is substituted or unsubstituted acetylene ($C_2$) or substituted or unsubstituted propargyl ($C_3$).

In certain embodiments, at least one instance of $R^3$ is substituted or unsubstituted carbocyclyl, e.g., substituted or unsubstituted $C_{3-6}$carbocyclyl, substituted or unsubstituted $C_{3-4}$carbocyclyl, substituted or unsubstituted $C_{4-5}$ carbocyclyl, or substituted or unsubstituted $C_{5-6}$ carbocyclyl.

In certain embodiments, at least one instance of $R^3$ is substituted or unsubstituted heterocyclyl, e.g., substituted or unsubstituted 3- to 6-membered heterocyclyl, substituted or unsubstituted 3- to 4-membered heterocyclyl, substituted or unsubstituted 4- to 5-membered heterocyclyl, or substituted or unsubstituted 5- to 6-membered heterocyclyl.

In certain embodiments, at least one instance of $R^3$ is substituted or unsubstituted aryl, e.g., substituted or unsubstituted phenyl.

In certain embodiments, at least one instance of $R^3$ is substituted or unsubstituted heteroaryl, e.g., substituted or unsubstituted 5- to 6-membered heteroaryl.

In certain embodiments, at least one instance of $R^3$ is —$NO_2$. In certain embodiments, at least one instance of $R^3$ is —CN. In certain embodiments, at least one instance of $R^3$ is —SCN. In certain embodiments, at least one instance of $R^3$ is —$OR^{A3}$, e.g., wherein $R^{A3}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or an oxygen protecting group.

In certain embodiments, at least one instance of $R^3$ is —$SR^{A3}$, e.g., wherein $R^{A3}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a sulfur protecting group.

In certain embodiments, at least one instance of $R^3$ is —$N(R^{A3})_2$, e.g., wherein each instance of $R^{A3}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group, or two $R^{A3}$ groups are joined to form a substituted or unsubstituted heterocyclic or heteroaryl ring.

In certain embodiments, at least one instance of $R^3$ is —$C(=O)R^{A3}$, e.g., wherein $R^{A3}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, substituted or unsubstituted hydroxyl, substituted or unsubstituted amino, or substituted or unsubstituted thiol.

In certain embodiments, at least one instance of $R^3$ is —$OC(=O)R^{A3}$, e.g., wherein $R^{A3}$ is hydrogen, substituted or unsubstituted alkyl, substituted or unsubstituted alkenyl, substituted or unsubstituted carbocyclyl, substituted or unsubstituted heterocyclyl, substituted or unsubstituted aryl, substituted or unsubstituted heteroaryl, substituted or unsubstituted hydroxyl, substituted or unsubstituted amino, or substituted or unsubstituted thiol.

In certain embodiments, at least one instance of $R^3$ is —$SC(=O)R^{A3}$, e.g., wherein $R^{A3}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, substituted or unsubstituted hydroxyl, substituted or unsubstituted amino, or substituted or unsubstituted thiol.

In certain embodiments, at least one instance of $R^3$ is —$NR^{A3}C(=O)R^{A3}$, e.g., wherein $R^{A3}$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, substituted or unsubstituted hydroxyl, substituted or unsubstituted amino, or substituted or unsubstituted thiol, or $R^{A3}$ is a nitrogen protecting group when attached to the nitrogen atom.

In certain embodiments, at least one instance of $R^3$ is —$S(=O)_2R^{A3}$, e.g., wherein $R^{A3}$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, substituted or unsubstituted hydroxyl, substituted or unsubstituted amino, or substituted or unsubstituted thiol.

In any of the above described embodiments, in certain instances, $R^{A3}$ is hydrogen.

In any of the above described embodiments, in certain instances, $R^{A3}$ is substituted or unsubstituted alkyl, e.g., substituted or unsubstituted $C_{1-6}$alkyl, substituted or unsubstituted $C_{1-2}$alkyl, substituted or unsubstituted $C_{2-3}$ alkyl, substituted or unsubstituted $C_{3-4}$alkyl, substituted or unsubstituted $C_{4-5}$alkyl, substituted or unsubstituted $C_{5-6}$alkyl, substituted or unsubstituted $C_1$alkyl, substituted or unsubstituted $C_2$alkyl, substituted or unsubstituted $C_3$alkyl, substituted or unsubstituted $C_4$alkyl, substituted or unsubstituted $C_5$alkyl, or substituted or unsubstituted $C_6$alkyl. In certain embodiments, $R^{A3}$ is methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), or n-hexyl ($C_6$).

In any of the above described embodiments, in certain instances, $R^{A3}$ is substituted or unsubstituted alkenyl, e.g., substituted or unsubstituted $C_{2-6}$alkenyl, substituted or unsubstituted $C_{2-3}$alkenyl, substituted or unsubstituted $C_{3-4}$alkenyl, substituted or unsubstituted $C_{4-5}$alkenyl, substituted or unsubstituted $C_{5-6}$alkenyl, substituted or unsubstituted $C_2$alkenyl, substituted or unsubstituted $C_3$alkenyl, substituted or unsubstituted $C_4$alkenyl, substituted or unsubstituted $C_5$alkenyl, or substituted or unsubstituted $C_6$alkenyl. In certain embodiments, $R^{A3}$ is substituted or unsubstituted allyl ($C_3$).

In any of the above described embodiments, in certain instances, $R^{A3}$ is substituted or unsubstituted alkynyl, e.g., substituted or unsubstituted $C_{2-6}$alkynyl, substituted or unsubstituted $C_{2-3}$alkynyl, substituted or unsubstituted $C_{3-4}$alkynyl, substituted or unsubstituted $C_{4-5}$alkynyl, substituted or unsubstituted $C_{5-6}$alkynyl, substituted or unsubstituted $C_2$alkynyl, substituted or unsubstituted $C_3$alkynyl, substituted or unsubstituted $C_4$alkynyl, substituted or unsubstituted $C_5$alkynyl, or substituted or unsubstituted $C_6$alkynyl. In certain embodiments, $R^{A3}$ is substituted or unsubstituted acetylene ($C_2$) or substituted or unsubstituted propargyl ($C_3$).

In any of the above described embodiments, in certain instances, $R^{A3}$ is substituted or unsubstituted carbocyclyl, e.g., substituted or unsubstituted $C_{3-6}$carbocyclyl, substituted or unsubstituted $C_{3-4}$carbocyclyl, substituted or unsubstituted $C_{4-5}$ carbocyclyl, or substituted or unsubstituted $C_{5-6}$ carbocyclyl.

In any of the above described embodiments, in certain instances, $R^{A3}$ is substituted or unsubstituted heterocyclyl, e.g., substituted or unsubstituted 3- to 6-membered heterocyclyl, substituted or unsubstituted 3- to 4-membered heterocyclyl, substituted or unsubstituted 4- to 5-membered heterocyclyl, or substituted or unsubstituted 5- to 6-membered heterocyclyl.

In any of the above described embodiments, in certain instances, $R^{A3}$ is substituted or unsubstituted aryl, e.g., substituted or unsubstituted phenyl.

In any of the above described embodiments, in certain instances, $R^{A3}$ is substituted or unsubstituted heteroaryl, e.g., substituted or unsubstituted 5- to 6-membered heteroaryl. In any of the above described embodiments, in certain instances, $R^{A3}$ is substituted or unsubstituted hydroxyl, substituted or unsubstituted amino, substituted or unsubstituted thiol, an oxygen protecting group when attached to an oxygen atom, a sulfur protecting group when attached to a sulfur atom, or a nitrogen protecting group when attached to a nitrogen atom.

In any of the above described embodiments, in certain instances, two $R^{A3}$ groups are joined to form a substituted or unsubstituted heterocyclic or heteroaryl ring, e.g., substituted or unsubstituted 3- to 6-membered heterocyclyl, substituted or unsubstituted 3- to 4-membered heterocyclyl, substituted or unsubstituted 4- to 5-membered heterocyclyl, or substituted or unsubstituted 5- to 6-membered heterocyclyl, or an substituted or unsubstituted 5- to 6-membered heteroaryl.

In certain embodiments, two $R^3$ groups are joined to form a substituted or unsubstituted aryl, substituted or unsubstituted heteroaryl, substituted or unsubstituted carbocyclic, or substituted or unsubstituted heterocyclic ring. Thus, for example, in any of the embodiments described herein, wherein m is 2, two $R^3$ groups vicinal to each other may be joined to form a substituted or unsubstituted aryl, substituted or unsubstituted heteroaryl, substituted or unsubstituted carbocyclic, or substituted or unsubstituted heterocyclic ring. Various bicyclic Ring B systems are contemplated from the joining of two vicinal $R^3$ groups.

In certain embodiments, two $R^3$ groups are joined to form a substituted or unsubstituted carbocyclyl, e.g., substituted or unsubstituted $C_{3-6}$carbocyclyl, substituted or unsubstituted $C_{3-4}$carbocyclyl, substituted or unsubstituted $C_{4-5}$ carbocyclyl, or substituted or unsubstituted $C_{5-6}$ carbocyclyl.

In certain embodiments, two $R^3$ groups are joined to form a substituted or unsubstituted heterocyclyl, e.g., substituted or unsubstituted 3- to 6-membered heterocyclyl, substituted or unsubstituted 3- to 4-membered heterocyclyl, substituted or unsubstituted 4- to 5-membered heterocyclyl, or substituted or unsubstituted 5- to 6-membered heterocyclyl. In certain embodiments, two $R^3$ groups are joined to form a substituted or unsubstituted aryl, e.g., substituted or unsubstituted phenyl.

In certain embodiments, two $R^3$ groups are joined to form a substituted or unsubstituted heteroaryl, e.g., substituted or unsubstituted 5- to 6-membered heteroaryl. As generally defined above for compounds of Formula (II), $R^4$ is hydrogen, substituted or unsubstituted alkyl, or an nitrogen protecting group, and ==== corresponds to a single or double bond.

In certain embodiments, $R^4$ is hydrogen.

In certain embodiments, $R^4$ is substituted or unsubstituted alkyl, e.g., substituted or unsubstituted $C_{1-6}$alkyl, substituted or unsubstituted $C_{1-2}$alkyl, substituted or unsubstituted $C_{2-3}$alkyl, substituted or unsubstituted $C_{3-4}$alkyl, substituted or unsubstituted $C_{4-5}$alkyl, substituted or unsubstituted $C_{5-6}$alkyl, substituted or unsubstituted $C_1$alkyl, substituted or unsubstituted $C_2$alkyl, substituted or unsubstituted $C_3$alkyl, substituted or unsubstituted $C_4$alkyl, substituted or unsubstituted $C_5$alkyl, or substituted or unsubstituted $C_6$alkyl.

In certain embodiments, $R^4$ is an nitrogen protecting group.

In certain embodiments, ==== corresponds to a single bond. In certain embodiments, ==== corresponds to a double bond.

Combinations of the above described embodiments are further contemplated.

For example, in certain embodiments of Formula (I) and (II), wherein p is 1, provided is a compound of Formula (I-a), (I-b), (I-c), (II-a), (II-b), or (II-c):

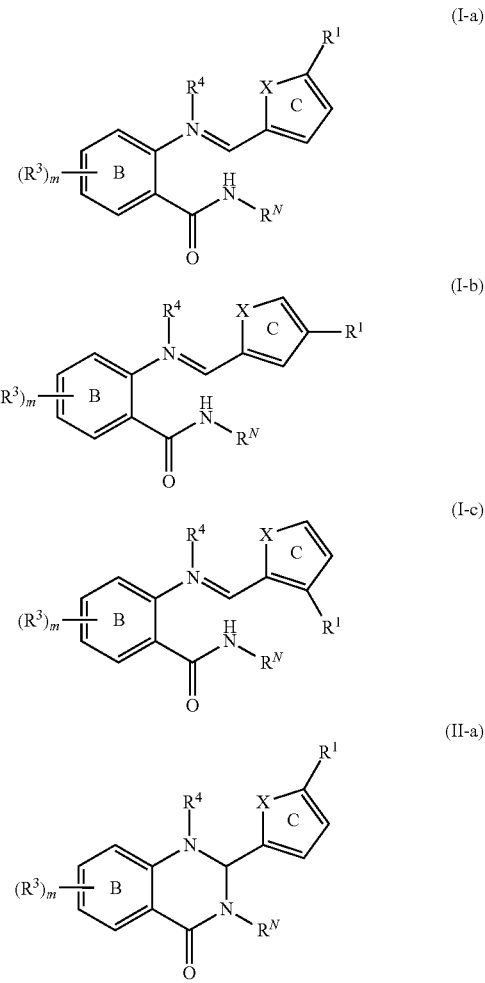

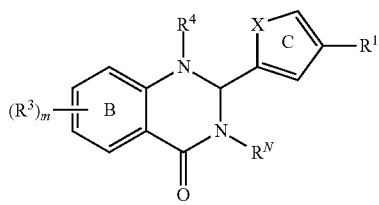
(II-b)

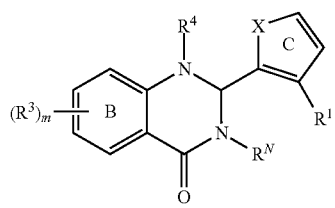
(II-c)

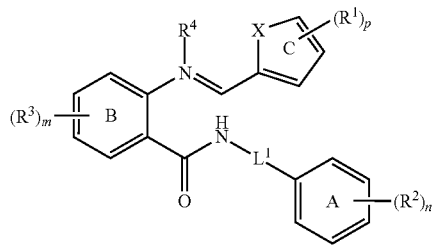
(I-d)

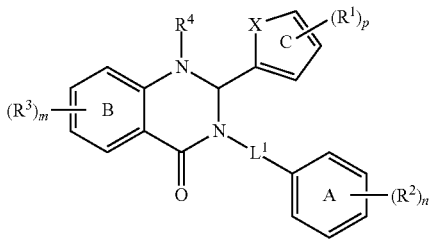
(II-d)

or a pharmaceutically acceptable salt, tautomer, prodrug, or stereoisomer thereof. In certain embodiments, X is S. In certain embodiments, ≡≡≡ corresponds to a double bond. In certain embodiments, $R^1$ is halo or substituted or unsubstituted $C_{1-6}$ alkyl. In certain embodiments, $R^1$ is —Br. In certain embodiments, $R^1$ is methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), or n-hexyl ($C_6$). In certain embodiments, $R^N$ is hydrogen, substituted or unsubstituted alkyl, substituted or unsubstituted alkenyl, substituted or unsubstituted alkynyl. In certain embodiments, $R^N$ is substituted or unsubstituted carbocyclyl. In certain embodiments, $R^N$ is a group of formula

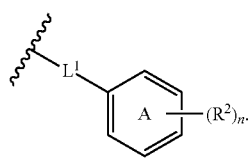

In certain embodiments, n is 0, 1, or 2. In certain embodiments, each instance of $R^2$ is independently halo, —$NO_2$, —$OR^{42}$. In certain embodiments, $L^1$ is a bond. In certain embodiments, $L^1$ is substituted or unsubstituted $C_1$alkylene, substituted or unsubstituted $C_2$alkylene, substituted or unsubstituted $C_3$alkylene. In certain embodiments, $L^1$ is methylene ($C_1$), ethylene ($C_2$), n-propylene ($C_3$). In certain embodiments, $L^1$ is —CH(CH$_3$)— having (R) or (S) stereochemistry. In certain embodiments, m is 0 or 1. In certain embodiments, each instance of $R^3$ is independently halo or substituted or unsubstituted alkyl. In certain embodiments, $R^4$ is hydrogen.

In certain embodiments of Formula (I) and (II), wherein $R^N$ comprises a Ring A, provided is a compound of Formula (I-d) or (II-d):

or a pharmaceutically acceptable salt, tautomer, prodrug, or stereoisomer thereof. In certain embodiments, X is S. In certain embodiments, ≡≡≡ corresponds to a double bond. In certain embodiments, $R^1$ is halo or substituted or unsubstituted $C_{1-6}$ alkyl. In certain embodiments, $R^1$ is —Br. In certain embodiments, $R^1$ is methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), or n-hexyl ($C_6$). In certain embodiments, n is 0, 1, or 2. In certain embodiments, each instance of $R^2$ is independently halo, —$NO_2$, —$OR^{42}$. In certain embodiments, $L^1$ is a bond. In certain embodiments, L is substituted or unsubstituted $C_1$alkylene, substituted or unsubstituted $C_2$alkylene, substituted or unsubstituted $C_3$alkylene. In certain embodiments, $L^1$ is methylene ($C_1$), ethylene ($C_2$), n-propylene ($C_3$). In certain embodiments, $L^1$ is —CH(CH$_3$)— having (R) or (S) stereochemistry. In certain embodiments, m is 0 or 1. In certain embodiments, each instance of $R^3$ is independently halo or substituted or unsubstituted alkyl. In certain embodiments, $R^4$ is hydrogen.

In certain embodiments of Formula (I) and (II), wherein p is 1 and $R^N$ comprises a Ring A, provided is a compound of Formula (I-e) and (II-e):

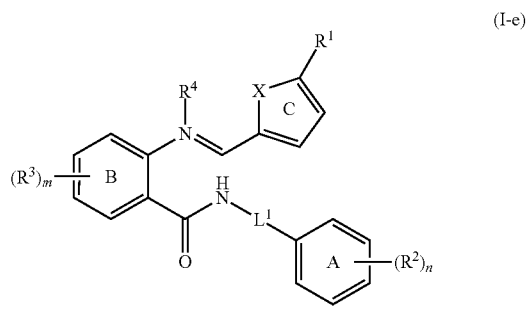
(I-e)

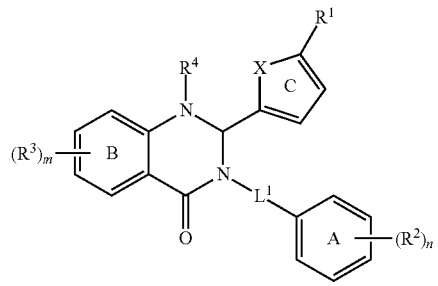
(II-e)
In certain embodiments of Formula (I) and (II), wherein p is 1, n is 0, 1, or 2, and $R^N$ comprises a Ring A, provided is a compound of any one of the following Formula:
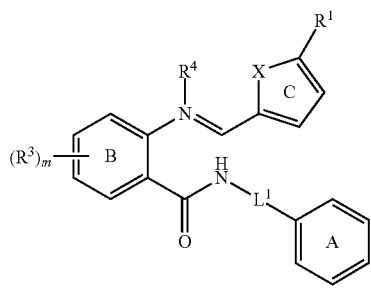
(I-f)
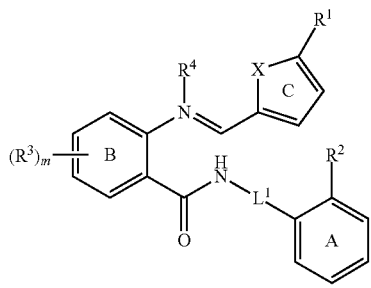
(I-g)
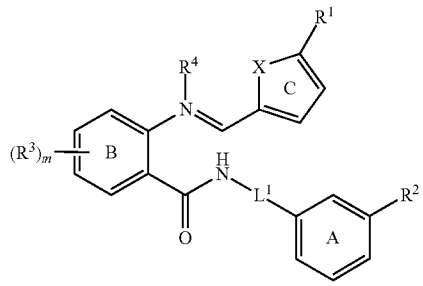
(I-h)
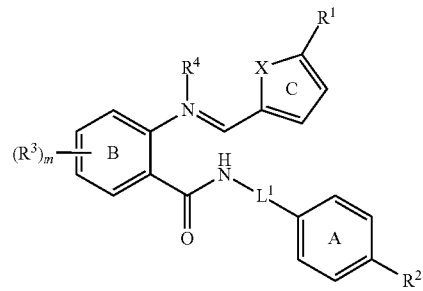
(I-i)
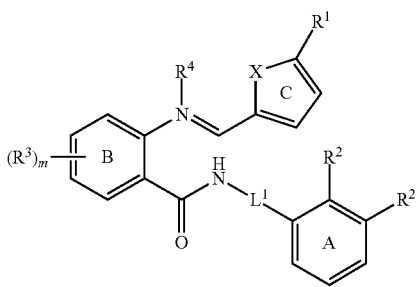
(I-j)
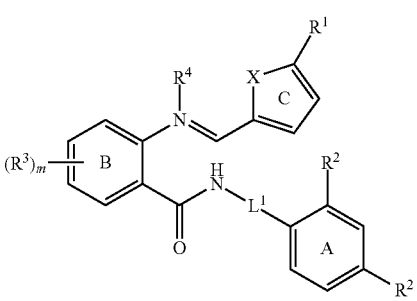
(I-k)
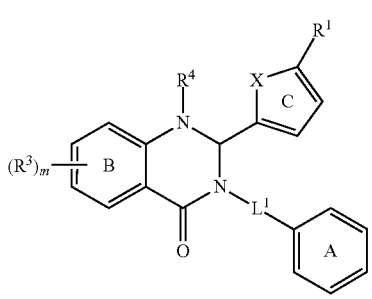
(II-f)
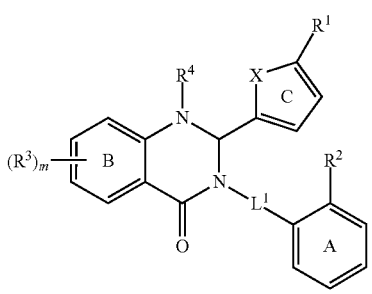
(II-g)
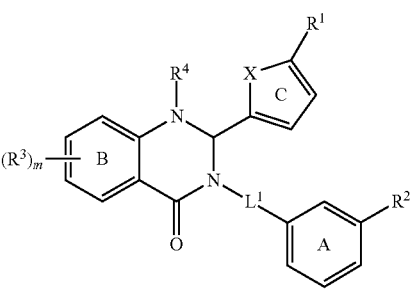
(II-h)

-continued

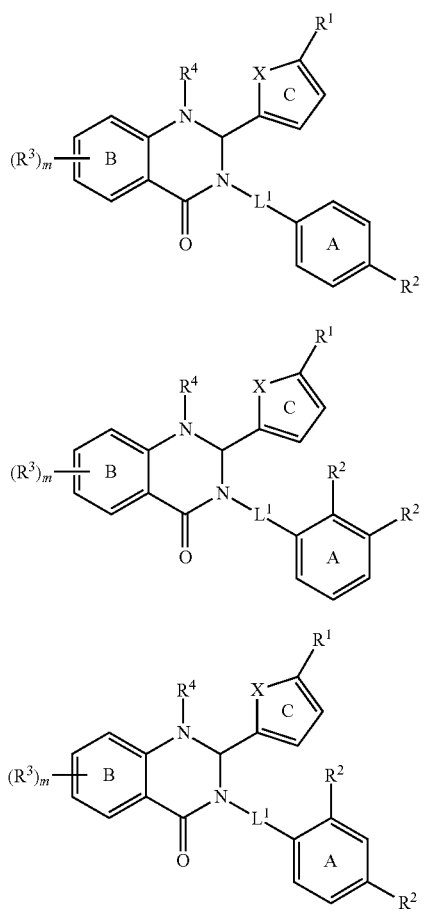

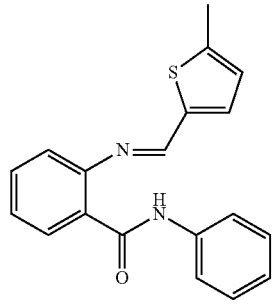
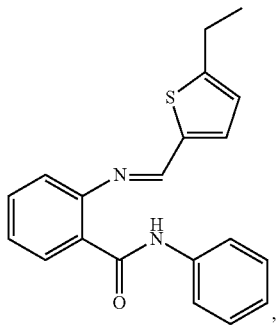

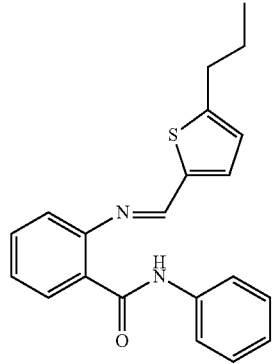
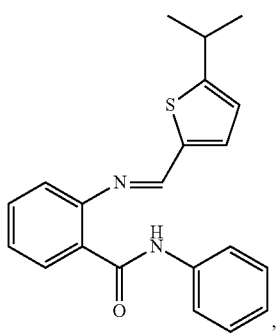

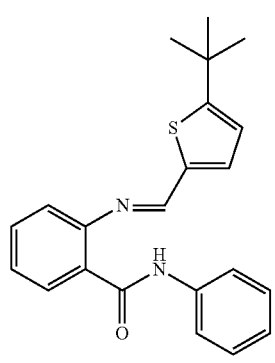
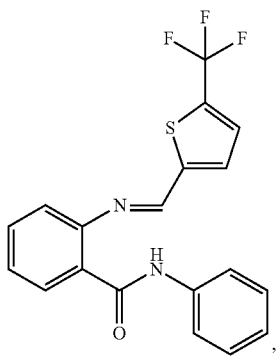

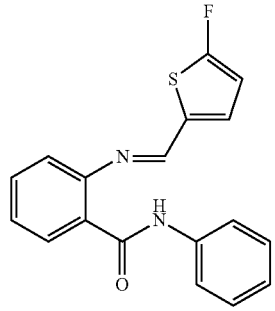
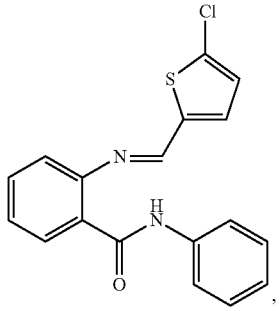

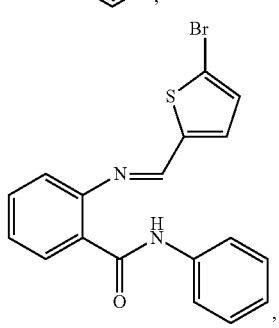
, and or a pharmaceutically acceptable salt, tautomer, prodrug, or stereoisomer thereof. In certain embodiments, X is S. In certain embodiments, ═══ corresponds to a double bond. In certain embodiments, $R^1$ is halo or substituted or unsubstituted $C_{1-6}$ alkyl. In certain embodiments, $R^1$ is —Br. In certain embodiments, $R^1$ is methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), or n-hexyl ($C_6$). In certain embodiments, each instance of $R^2$ is independently halo, —$NO_2$, —$OR^{42}$. In certain embodiments, $L^1$ is a bond. In certain embodiments, $L^1$ is substituted or unsubstituted $C_1$alkylene, substituted or unsubstituted $C_2$alkylene, substituted or unsubstituted $C_3$alkylene. In certain embodiments, $L^1$ is methylene ($C_1$), ethylene ($C_2$), n-propylene ($C_3$). In certain embodiments, $L^1$ is —CH(CH$_3$)— having (R) or (S) stereochemistry. In certain embodiments, m is 0 or 1. In certain embodiments, each instance of $R^3$ is independently halo or substituted or unsubstituted alkyl. In certain embodiments, $R^4$ is hydrogen.

Specific compounds of Formula (I) and (II) are further contemplated herein.

For example, compounds of Formula (I), and pharmaceutically acceptable salts, tautomers, prodrugs, and stereoisomers thereof, include, but are not limited to:

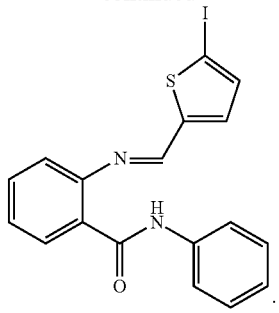 [SMILES: O=C(Nc1ccccc1)c1ccccc1/N=C/c1ccc(I)s1]
However, in certain embodiments, the compound of Formula (I) is not 2-(((5-methylthiophen-2-yl)methylene)amino)-N-phenylbenzamide or N-phenyl-2-((thiophen-2-ylmethylene)amino)benzamide:
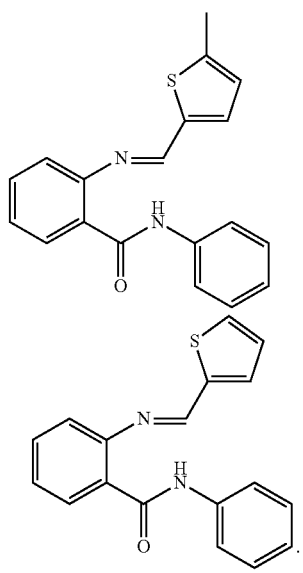
Compounds of Formula (II), and pharmaceutically acceptable salts, tautomers, prodrugs, and stereoisomers thereof, include, but are not limited to:
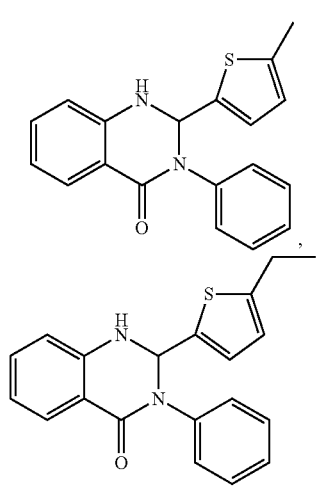
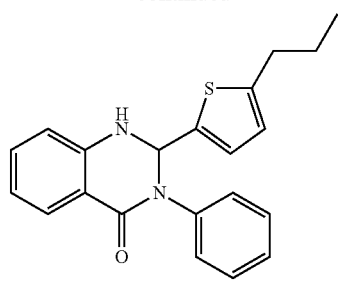
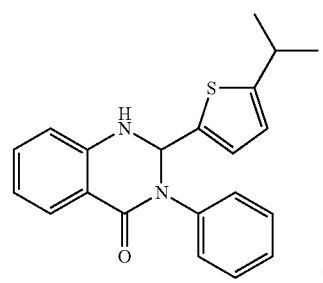
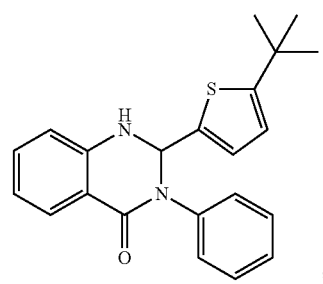
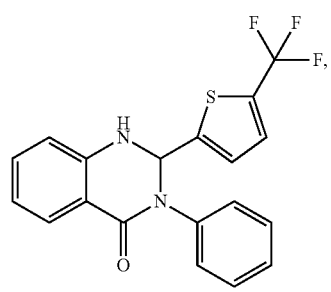
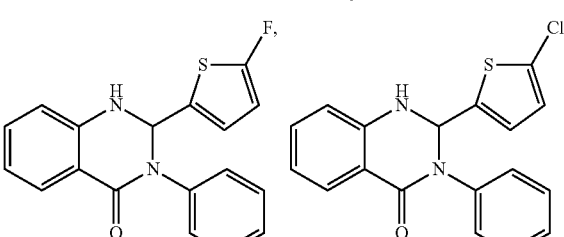
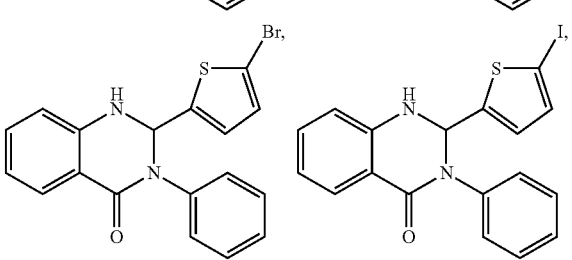

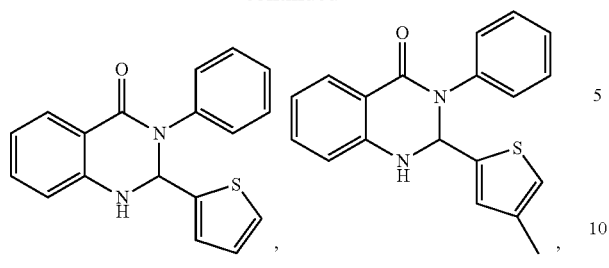,
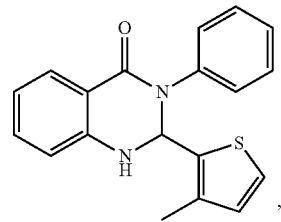,
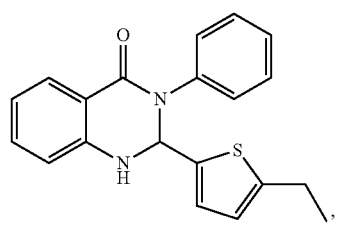,
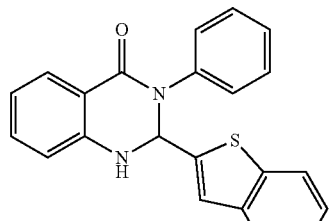,
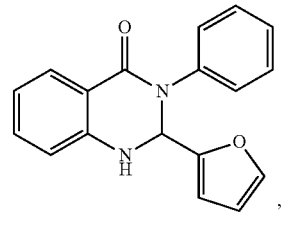,
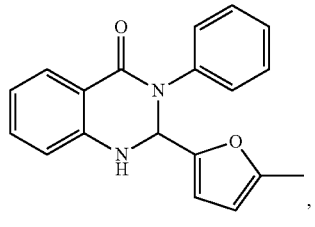,
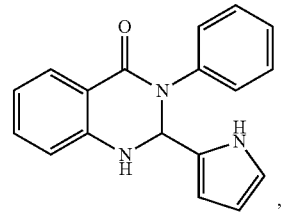,
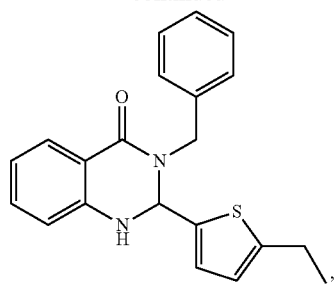,
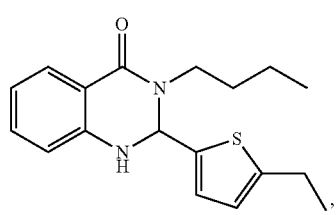,
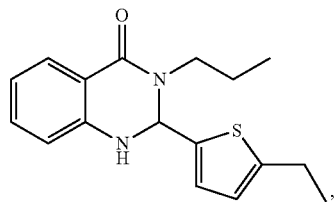,
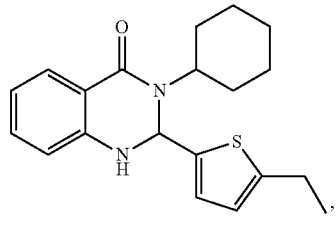,
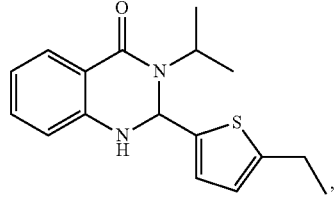,
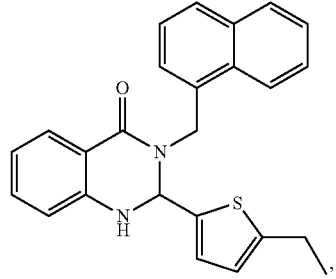,
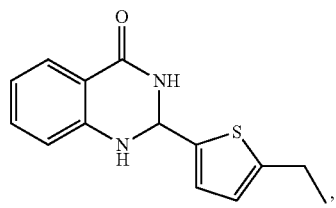,

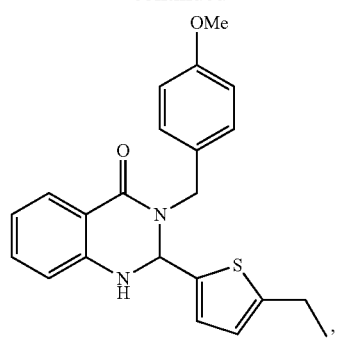
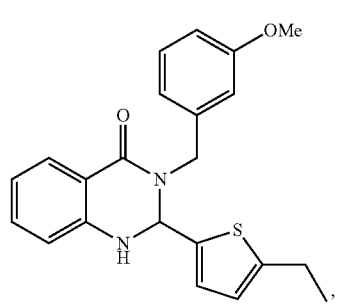
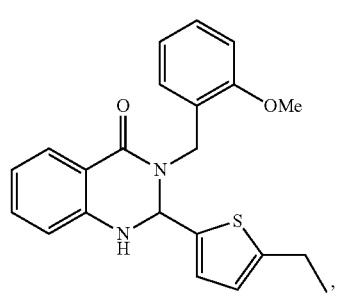
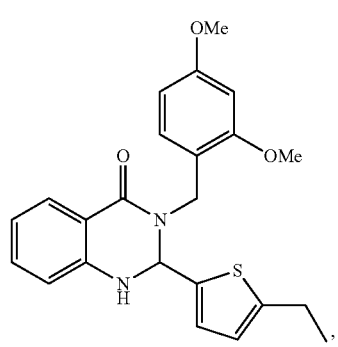
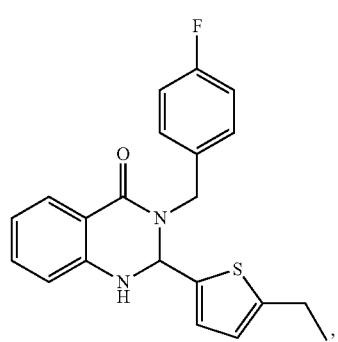
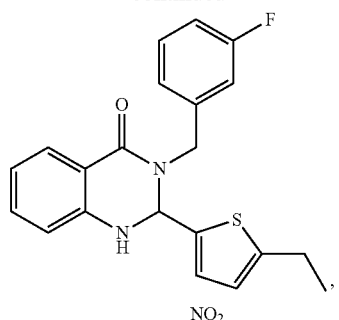
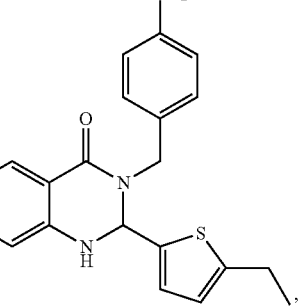
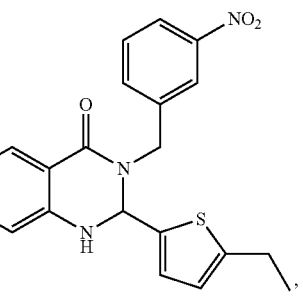
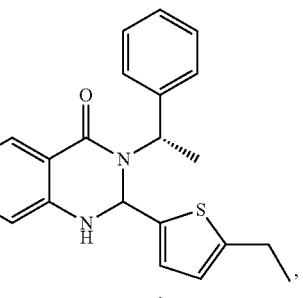
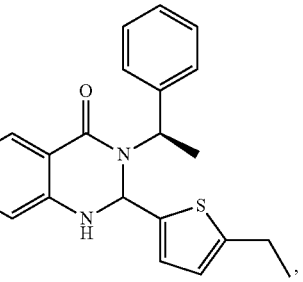
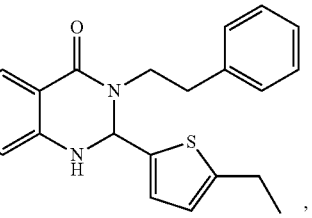

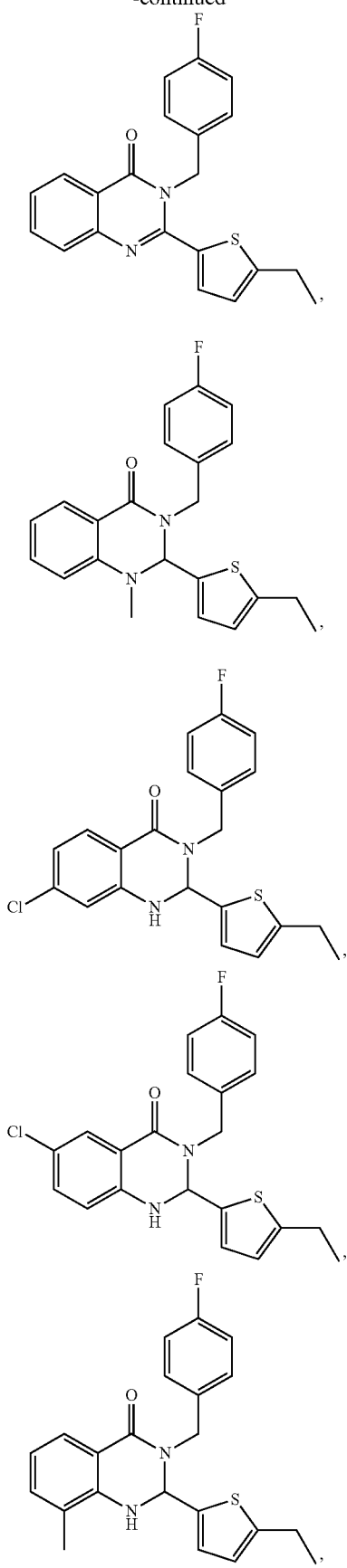
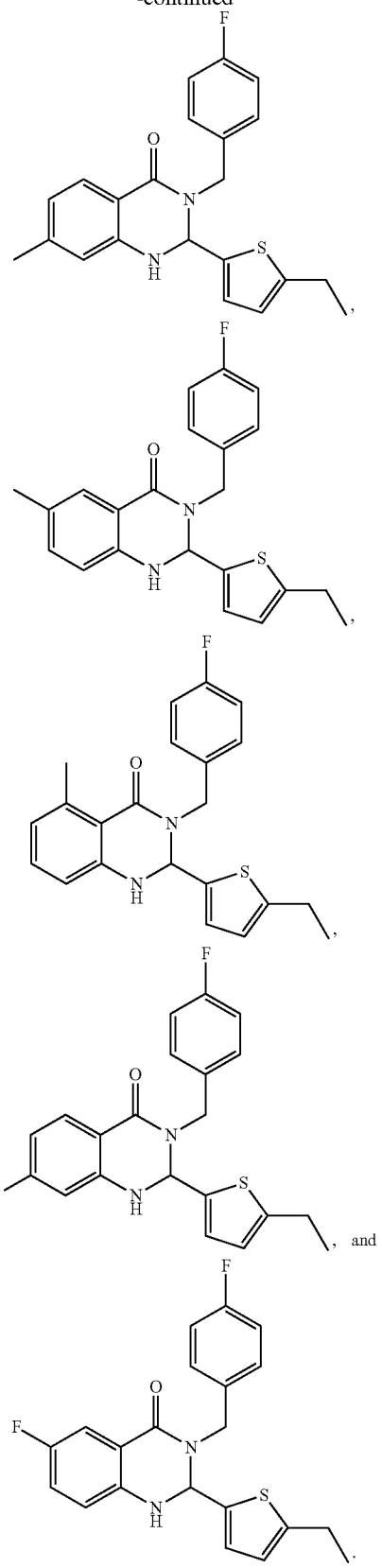
However, in certain embodiments, the compound of Formula (II) is not 2-(5-methylthiophen-2-yl)-3-phenyl-2,3- dihydroquinazolin-4(1H)-one or 3-phenyl-2-(thiophen-2-yl)-2,3-dihydroquinazolin-4(1H)-one:

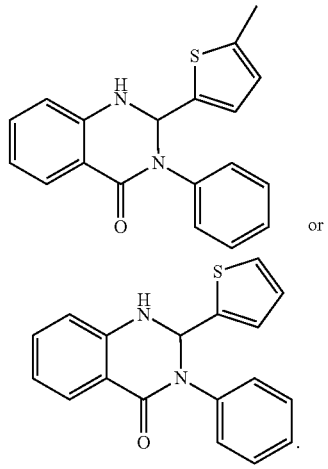

or

Pharmaceutical Compositions

In still yet another aspect, provided are pharmaceutical compositions comprising a compound of Formula (I) and (II), or a mixture thereof, or a pharmaceutically acceptable salt, tautomer, prodrug, or stereoisomer thereof, and a pharmaceutically acceptable excipient. Compounds of Formula (I) and (II) are also referred to herein as the "active ingredient(s)." In certain embodiments, the pharmaceutical composition comprises an effective amount of the active ingredient(s). In certain further embodiments, the pharmaceutical composition is useful as a medicament for the treatment and prevention of a viral infection and/or a pathogenic condition associated with aberrant endosomal trafficking.

Pharmaceutically acceptable excipients include any and all solvents, diluents or other liquid vehicles, dispersion or suspension aids, surface active agents, isotonic agents, thickening or emulsifying agents, preservatives, solid binders, lubricants and the like, as suited to the particular dosage form desired. General considerations in the formulation and/or manufacture of pharmaceutical compositions agents can be found, for example, in *Remington's Pharmaceutical Sciences*, Sixteenth Edition, E. W. Martin (Mack Publishing Co., Easton, Pa., 1980), and *Remington: The Science and Practice of Pharmacy*, 21$^{st}$ Edition (Lippincott Williams & Wilkins, 2005).

Pharmaceutical compositions described herein can be prepared by any method known in the art of pharmacology. In general, such preparatory methods include the steps of bringing the active ingredient(s) into association with a carrier and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is discrete amount of the pharmaceutical composition comprising a predetermined amount of the active ingredient(s). The amount of the active ingredient(s) is generally equal to the dosage of the active ingredient(s) which would be administered to a subject and/or a convenient fraction of such a dosage such as, for example, one-half or one-third of such a dosage. Pharmaceutically acceptable excipients used in the manufacture of the pharmaceutical composition include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and combinations thereof.

Exemplary granulating and/or dispersing agents include potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, etc., and combinations thereof.

Exemplary surface active agents and/or emulsifiers include natural emulsifiers (e.g. *acacia*, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g. Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof.

Exemplary binding agents include starch (e.g. cornstarch and starch paste), gelatin, sugars (e.g. sucrose, glucose, dextrose, dextrin, molasses, lactose, lactitol, mannitol, etc.), natural and synthetic gums (e.g. *acacia*, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, etc., and/or combinations thereof.

Exemplary preservatives include antioxidants, chelating agents, antimicrobial preservatives, antifungal preservatives, alcohol preservatives, acidic preservatives, and other preservatives.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and combinations thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, *eucalyptus*, evening primrose, fish, flaxseed, geraniol, gourd, grape seed, hazel nut, hyssop, isopropyl myristate, jojoba, kukui nut, lavandin, lavender, lemon, *litsea cubeba*, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

Liquid dosage forms for oral and parenteral administration include pharmaceutically acceptable emulsions, microemulsions, solutions, suspensions, syrups and elixirs. In addition to the active ingredient(s)s, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as Cremophor, alcohols, oils, modified oils, glycols, polysorbates, cyclodextrins, polymers, and combinations thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are typically suppositories which can be prepared by mixing the conjugates of this invention with suitable non-irritating excipients or carriers such as cocoa butter, polyethylene glycol or a suppository wax which are solid at ambient temperature but liquid at body temperature and therefore melt in the rectum or vaginal cavity and release the active ingredient(s).

Solid dosage forms for oral administration include capsules, tablets, pills, powders, and granules. In such solid dosage forms, the active ingredient(s) is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and *acacia, c*) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may comprise buffering agents.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

The active ingredient(s) can be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient(s) can be admixed with at least one inert diluent such as sucrose, lactose or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions. Topically-administrable formulations may, for example, comprise from about 0.01% to about 10% (w/w) active ingredient(s), although the concentration of the active ingredient(s) can be as high as the solubility limit of the active ingredient(s) in the solvent. Formulations for topical administration may further comprise one or more of the additional ingredients described herein.

A pharmaceutical composition of the invention can be prepared, packaged, and/or sold in a formulation suitable for pulmonary administration via the buccal cavity. Such a formulation may comprise dry particles which comprise the active ingredient(s) and which have a diameter in the range from about 0.5 to about 7 nanometers or from about 1 to about 6 nanometers. Such compositions are conveniently in the form of dry powders for administration using a device comprising a dry powder reservoir to which a stream of propellant can be directed to disperse the powder and/or using a self propelling solvent/powder dispensing container such as a device comprising the active ingredient(s) dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Pharmaceutical compositions of the invention formulated for pulmonary delivery may provide the active ingredient(s) in the form of droplets of a solution and/or suspension. Such formulations can be prepared, packaged, and/or sold as aqueous and/or dilute alcoholic solutions and/or suspensions, optionally sterile, comprising the active ingredient(s), and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

The formulations described herein as being useful for pulmonary delivery are useful for intranasal delivery of a pharmaceutical composition. Another formulation suitable for intranasal administration is a coarse powder comprising the active ingredient(s) and having an average particle from about 0.2 to 500 micrometers. Such a formulation is administered by rapid inhalation through the nasal passage from a container of the powder held close to the nares.

Formulations suitable for nasal administration may, for example, comprise from about as little as 0.1% (w/w) and as much as 100% (w/w) of the active ingredient(s), and may comprise one or more of the additional ingredients described herein. A pharmaceutical composition can be prepared, packaged, and/or sold in a formulation suitable for buccal administration. Such formulations may, for example, be in the form of tablets and/or lozenges made using conventional methods, and may contain, for example, 0.1 to 20% (w/w) active ingredient(s), the balance comprising an orally dissolvable and/or degradable composition and, optionally, one or more of the additional ingredients described herein. Alternately, formulations suitable for buccal administration may comprise a powder and/or an aerosolized and/or atomized solution and/or suspension comprising the active ingredient(s). Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition can be prepared, packaged, and/or sold in a formulation suitable for ophthalmic administration. Such formulations may, for example, be in the form of eye drops including, for example, a 0.1/1.0% (w/w) solution and/or suspension of the active ingredient(s) in an aqueous or oily liquid carrier. Such drops may further comprise buffering agents, salts, and/or one or more other of the additional ingredients described herein. Other opthalmically-administrable formulations which are useful include those which comprise the active ingredient(s) in microcrystalline form and/or in a liposomal preparation. Ear drops and/or eye drops are contemplated as being within the scope of this invention.

Compounds provided herein are typically formulated in dosage unit form for ease of administration and uniformity of dosage. It will be understood, however, that the total daily usage of the compositions of the present invention will be decided by the attending physician within the scope of sound medical judgment. The specific therapeutically effective dose level for any particular subject or organism will depend upon a variety of factors including the disease, disorder, or condition being treated and the severity of the disorder; the activity of the specific active ingredient(s) employed; the specific composition employed; the age, body weight, general health, sex and diet of the subject; the time of administration, route of administration, and rate of excretion of the specific active ingredient(s) employed; the duration of the treatment; drugs used in combination or coincidental with the specific active ingredient(s) employed; and like factors well known in the medical arts.

The active ingredient(s) provided herein can be administered by any route, including oral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, enteral, sublingual; by intratracheal instillation, bronchial instillation, and/or inhalation; and/or as an oral spray, nasal spray, and/or aerosol. In general the most appropriate route of administration will depend upon a variety of factors including the nature of the agent (e.g., its stability in the environment of the gastrointestinal tract), the condition of the subject (e.g., whether the subject is able to tolerate oral administration), etc.

The exact amount of the active ingredient(s) required to achieve an effective amount will vary from subject to subject, depending, for example, on species, age, and general condition of a subject, severity of the side effects or disorder, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of the active ingredient(s) for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of an inventive compound per unit dosage form. It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

It will be also appreciated that the active ingredient(s), as described herein, can be administered in combination with one or more additional active agents. The active ingredient(s) can be administered concurrently with, prior to, or subsequent to, one or more additional active agents. In general, each active ingredient(s) and additional active agent will be administered at a particular dose and/or on a particular time schedule. In will further be appreciated that the additional active agent utilized in this combination can be administered together in a single composition or administered separately in different compositions. The particular combination to employ in a regimen will take into account compatibility of the active ingredient(s), with the additional active agent and/or the desired therapeutic effect to be achieved. In general, it is expected that additional active agents utilized in combination be utilized at levels that do not exceed the levels at which they are utilized individually. In some embodiments, the levels utilized in combination will be lower than those utilized individually. The additional active agents may improve the active ingredient(s) bioavailability, reduce and/or modify their metabolism, inhibit their excretion, and/or modify their distribution within the body. It will also be appreciated that therapy employed may achieve a desired effect for the same condition, e.g., anti-infective activity, and/or it may achieve different effects (e.g., control of adverse side-effects).

Exemplary one or more additional active agents includes, but is not limited to, anti-viral agents. In certain embodiments, the anti-viral agent is a virus receptor antagonist. In certain embodiments, the virus receptor antagonist is an inhibitor of serotonin receptor. In certain embodiments, the anti-viral agent is an antibody, e.g., designed to recognize the virus and prevent initial infection.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation. General considerations in the formulation and/or manufacture of pharmaceutical compositions can be found, for example, in Remington: The Science and Practice of Pharmacy 21st ed., Lippincott Williams & Wilkins, 2005.

Still further encompassed by the invention are pharmaceutical kits. Pharmaceutical kits provided may comprise a pharmaceutical composition, as described herein, and a container (e.g., a vial, ampoule, bottle, syringe, and/or dispenser package, or other suitable container), and instructions for use. In some embodiments, the kits may optionally further include a second container comprising a suitable aqueous carrier for dilution or suspension of the composition for preparation of administration to a subject. Instructions may provide, for example, instructions for dosage and administration, specialized instructions for particular containers and/or systems for administration, and/or instructions for use in combination with additional therapies.

Methods of Treatment and Use

The present invention is based, in part, on the discovery that the imine 2-(((5-methylthiophen-2-yl)methylene)amino)-N-phenylbenzamide (RETRO-2) and the corresponding cyclized product, 2-(5-methylthiophen-2-yl)-3-phenyl-2,3-dihydroquinazolin-4(1H)-one (Retro-2$^{cycl}$), encompassed by Formula (I) or (II), respectively, are inhibitors of polyomavirus (e.g., JCV, BKV, and SV40) infectivity. Thus, in one aspect, the present invention provides use of compounds of Formula (I) or (II) for treating and preventing viral infections, such as polyomaviral infections. In certain embodiments, the compounds of Formula (I) or (II) are useful in reducing infectivity.

RETRO-2 was initially described in Stechmann et al., Cell (2010) 141:231-242 as an AB5 toxin inhibitor; thus novel compounds of Formula (I) and (II) are further contemplated useful in treating or preventing conditions caused by AB5 toxin, such as treating or preventing an infection with a pathogen (e.g., bacteria) that secretes an AB5 toxin. Such AB5 toxins include, but are not limited to, the toxin ricin, Shiga toxin and Shiga-like toxins, cholera toxin, heat-labile enterotoxin, pertussis toxin, and subtilase cytotoxin.

Figure 6:
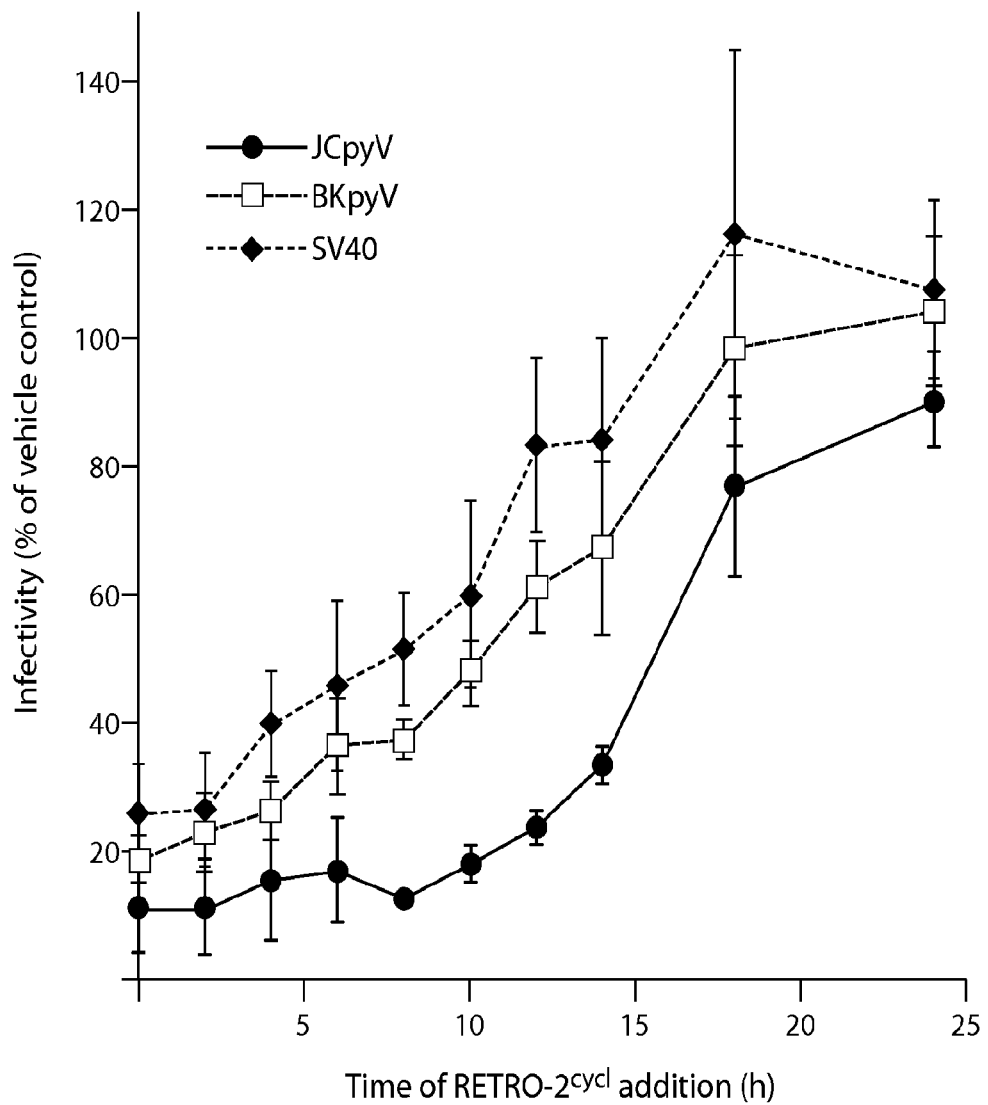
FIG. 6 depicts the time course of inhibition of JCV, BKV, and SV40 infection in cells treated with Retro-$2^{cycl}$.

Polyomaviruses traffic to the ER, but, unlike AB5 toxin, the polyomavirus does not traffic to the ER via the Golgi apparatus, but appears to bypass the Golgi en route to the ER. See, e.g., Ewers et al., Cold Spring Harb Perspect Biol (2011) 3:a004721. Data suggests that the Retro-2$^{cycl}$ blocks one or more steps in this genomic trafficking. See FIG. 6, infra. The present invention further contemplates use of compounds of Formula (I) and (II) as inhibitors of pathogenic conditions associated with endosomal trafficking, e.g., conditions wherein a pathogen uses a host cell's endosomal trafficking pathway.

Thus, in one aspect, the present invention provides a method of treating or preventing a viral infection, the method comprising administering to a subject suffering from or likely to suffer from a viral infection an effective amount of a compound of Formula (I) or (II), or a mixture thereof, or pharmaceutically acceptable salt, tautomer, prodrug, or stereoisomer thereof.

In another aspect, the present invention provides a method of treating or preventing a pathogenic condition associated with endosomal trafficking, the method comprising administering to a subject suffering from or likely to suffer from the condition an effective amount of a compound of Formula (I) or (II), or a mixture thereof, or pharmaceutically acceptable salt, tautomer, prodrug, or stereoisomer thereof. In certain embodiments, the pathogenic condition is a bacterial infection, a fungal infection, a parasitic infection, or a viral infection. In certain embodiments, the pathogenic condition is a bacterial infection. In certain embodiments, the pathogenic condition is a viral infection.

In yet another aspect, the present invention provides a method of treating or preventing an infection by a pathogen that secretes AB5 toxin, the method comprising administering to a subject suffering from or likely to suffer from the infection an effective amount of a compound of Formula (I) or (II), or a mixture thereof, or pharmaceutically acceptable salt, tautomer, prodrug, or stereoisomer thereof. In certain embodiments, the pathogen secreting an AB5 toxin is a bacteria, e.g., E. coli. In certain embodiments, the AB5 toxin is the toxin ricin, Shiga toxin, Shiga-like toxins, cholera toxin, heat-labile enterotoxin, pertussis toxin, or subtilase cytotoxin.

In yet another aspect, the present invention provides a method of treating or preventing an infection by a pathogen that secretes a toxin that relies on retrograde endosomal trafficking, the method comprising administering to a subject suffering from or likely to suffer from the infection an effective amount of a compound of Formula (I) or (II), or a mixture thereof, or pharmaceutically acceptable salt, tautomer, prodrug, or stereoisomer thereof.

Therapeutic and prophylactic methods of the above are contemplated.

For example, in certain embodiments, the methods as described herein are therapeutic treatment methods, comprising administering to a subject suffering from the infection or condition an effective amount of a compound of Formula (I) or (II), or a mixture thereof, or pharmaceutically acceptable salt, tautomer, prodrug, or stereoisomer thereof.

Alternatively, in certain embodiments, the methods as described herein are preventative methods, comprising administering to a subject likely to suffer from the infection or condition an effective amount of a compound of Formula (I) or (II), or a mixture thereof, or pharmaceutically acceptable salt, tautomer, prodrug, or stereoisomer thereof.

In certain embodiments, the viral infection or pathogenic condition requires retrograde endosomal transport of the pathogen's (viral) genome to the cell nucleus. In certain embodiments, the compound of Formula (I) or (II), or a mixture thereof, or pharmaceutically acceptable salt, tautomer, prodrug, or stereoisomer thereof, inhibits retrograde endosomal transport of the pathogen's (viral) genome to the cell nucleus. In certain embodiments, the pathogen is a virus. In certain embodiments, the pathogen is a polyomavirus.

In certain embodiments, the viral infection is an infection caused by human papillomavirus (HPV). In certain embodiments, the HPV is HPV-16 or HPV-18.

In certain embodiments, the viral infection is an infection caused by human immunodeficiency virus (HIV). In certain embodiments, the HIV is HIV type 1 (HIV-1).

In certain embodiments, the viral infection is an infection caused by influenza virus. In certain embodiments, the influenza virus is influenzavirus A, influenzavirus B, influenzavirus C, or human parainfluenza virus. In certain embodiments, influenzavirus A is H1N1, H2N2, H3N2, H5N1, H7N7, H1N2, H9N2, H7N2, H7N3, or H10N7.

In certain embodiments, the viral infection is an infection caused by polyomavirus. In certain embodiments, the polyomavirus is JC-polyomavirus, BK-polyomavirus KI-polyomavirus, WU-polyomavirus, Merkel cell polyomavirus, HPyV6, HPyV7, trichodysplasia spinulosa-associated polyomavirus, HPyV9, MW polyomavirus, or the monkey polyomavirus SV40. In certain embodiments, the viral infection is an infection in a human subject caused by human polyomavirus.

In certain embodiments, the viral infection is JCV, and the subject further suffers from progressive multifocal leukoencephalopathy (PML).

In certain embodiments, the viral infection is BKV, and the subject further suffers from kidney necrosis and/or polyomavirus-induced neuropathy (PVN).

In certain embodiments, the viral infection is KIV or WUV, and the subject further suffers from a respiratory tract infection.

In certain embodiments, the viral infection is MCV, and the subject further suffers from Merkel cell carcinomas of the skin.

In certain embodiments, the viral infection is TSV, and the subject further suffers from proliferative skin lesions.

In certain embodiments, the subject is human. In certain embodiments, the human subject is immusuppresed. In certain embodiments, the subject is immunosuppressed due to an infection (e.g., HIV infection). In certain embodiments, the subject is immunosuppressed due to an autoimmune disease (e.g., rheumatoid arthritis, multiple sclerosis). In certain embodiments, the subject is immunosuppressed due to cancer or cancer treatment (e.g., upon treatment with immunomodulatory drugs). In certain embodiments, the subject is immunosuppressed due to old age (e.g., older than 65 years old). In certain embodiments, the subject is immunosuppressed due to organ transplantation.

EXAMPLES

These and other aspects of the present invention will be further appreciated upon consideration of the following Examples, which are intended to illustrate certain particular embodiments of the invention but are not intended to limit its scope, as defined by the claims.

Retro-$2^{cycl}$ as an Inhibitor of Polyomavirus Infectivity

We discovered a small molecule that inhibits infection by two human polyomaviruses, JCV and BKV, and the monkey polyomavirus SV40, RETRO-2 and Retro-$2^{cycl}$. RETRO-2 forms the closed ring structure Retro-$2^{cycl}$ rapidly in solution, so it is likely that Retro-$2^{cycl}$ is the active form in cellulo and in vivo. As the compound interacts with host cell factors rather than the polyomavirus themselves, it is also likely that escape mutants will arise less frequently. RETRO-2 and Retro-$2^{cycl}$ and analogs thereof represent the first potential treatment that broadly inhibits polyomaviruses.

Figure 2:
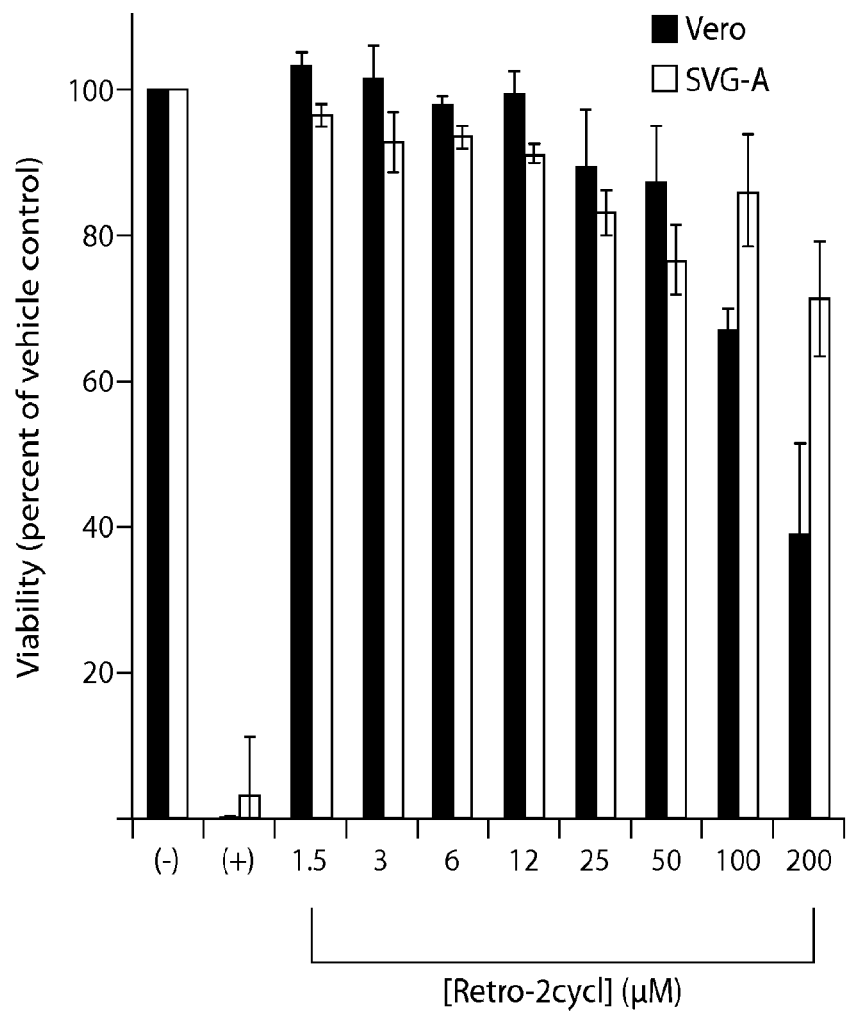
FIG. 2 depicts the viability of cells treated with Retro-$2^{cycl}$.

The viability of SVG-A or Vero cells were first tested after treatment with Retro-$2^{cycl}$. See FIG. 2. Cells were treated with Retro-$2^{cycl}$ at the indicated concentrations for 72 h before viability was assessed using the CellTiter 96 AQueous One Solution Cell Proliferation Assay. As a control, cells were treated with either 0.04% DMSO or with 10% SDS. Error bars denote standard deviation. The data demonstrates Retro-$2^{cycl}$ is effective at doses that do not negatively affect cell viability.

Figure 1B:
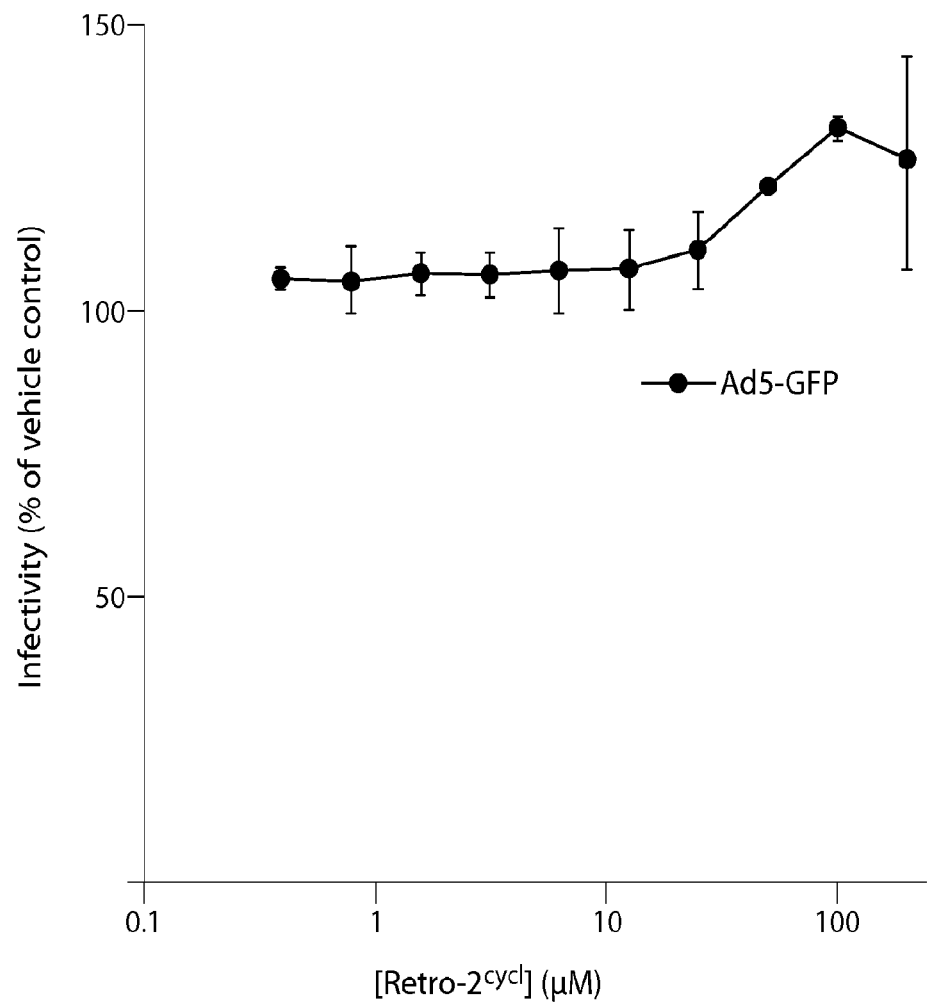

It was further found that Retro-$2^{cycl}$ inhibits infectivity of JCV, BKV, or SV40 at differing concentrations. See FIG. 1. Cells were infected with the indicated concentration of virus for 1 h. Media was then added to these cells containing the indicated concentration of Retro-$2^{cycl}$ and cells were incubated for 72 h. Cells were then detached from each well, fixed, permeabalized, and stained with monoclonal antibody against VP1 that has been covalently labeled with Alexa Fluor 488. Infected cells were scored by flow cytometry, and were normalized against an infected control that was treated with the vehicle DMSO. The DMSO concentration was 0.04% in all samples. Error bars denote standard deviation.

These data demonstrates Retro-$2^{cycl}$ inhibits polyomavirus in a dose dependent manner. As a negative control, Vero cells were incubated with an Adenovirus Type 5 pseudovirus that expresses GFP in transduced cells (Ad5-GFP). Since Adenovirus does not undergo retrograde trafficking the golgi complex or endoplasmic reticulum, treatment with Retro-$2^{cycl}$ was expected to have no effect on cellular transduction. These data demonstrates that Ad5-GFP transduction is unaffected by Retro-$2^{cycl}$ treatment.

Figure 3:
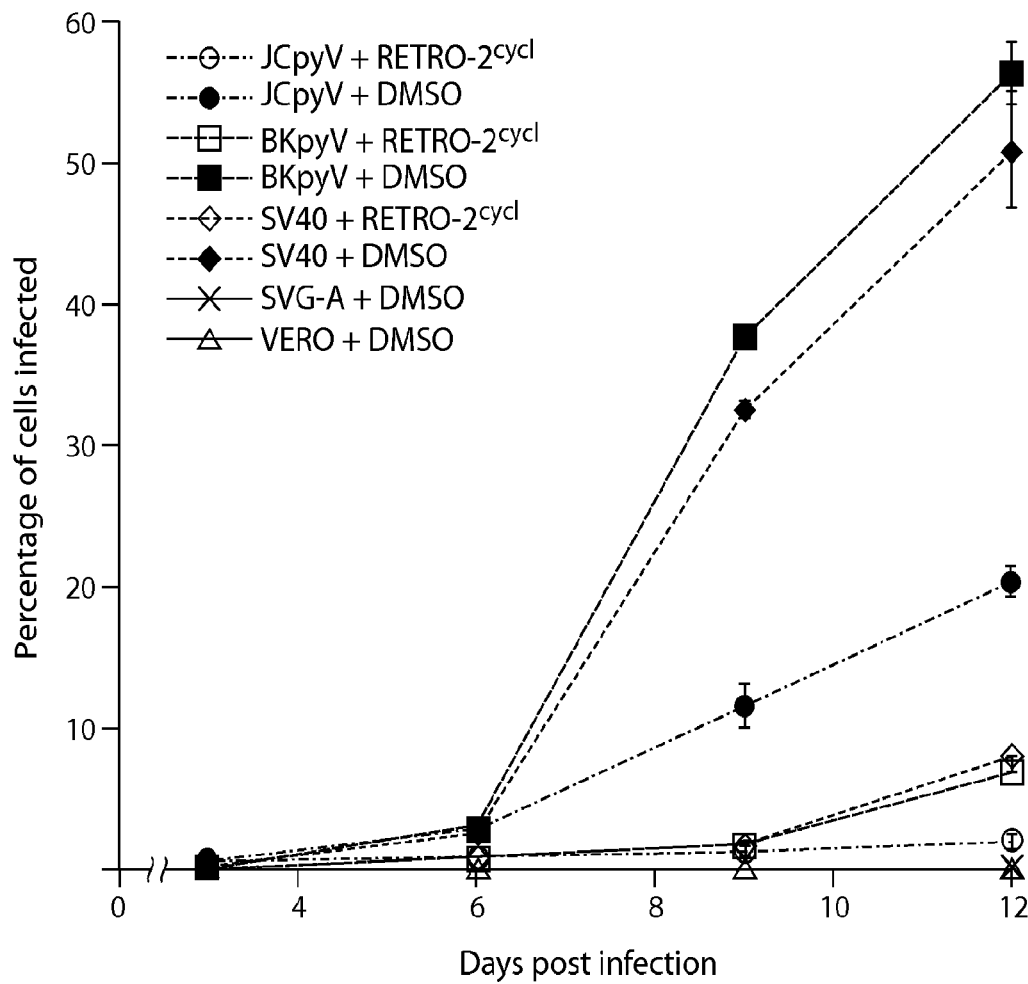
FIG. 3 depicts the inhibitory activity of Retro-$2^{cycl}$ against an already established infection of cells by JCV, BKV, and SV40 polyomaviruses. Retro-$2^{cycl}$ prevents spread of virus in a multicycle growth assay. Cells were infected with JCpyV, BKpyV, or SV40 at an MOI if 0.01 and allowed to replicate for 72 h. Cells were then treated with 0.1 mM Retro-$2^{cycl}$ and this culture media was replaced daily with fresh media containing 0.1 mM Retro-$2^{cycl}$. Cells were scored for infection every three days by flow cytometry. Data represents the mean of three replicates and error bars indicate standard deviation.

Retro-$2^{cycl}$ further prevents spread of JCV, BKV, or SV40 in established tissue culture infections. See FIG. 3. Cells were infected with JCV, BKV, or SV40 at an multiplicity of infection of approximately 0.01 and were allowed to infect cells for 72 h. After 72 h, 100 µM of Retro-$2^{cycl}$ was added to each sample. Tissue culture media was replaced each day with fresh media containing Retro-$2^{cycl}$. Replicates were assayed at 3, 6, 9, and 12 days post infection and the percentage of infected cells was determined by flow cytometry. Error bars denote standard deviation. The data demonstrates Retro-$2^{cycl}$ reduces the spread of polyomavirus over time in tissue culture.

Figure 4:
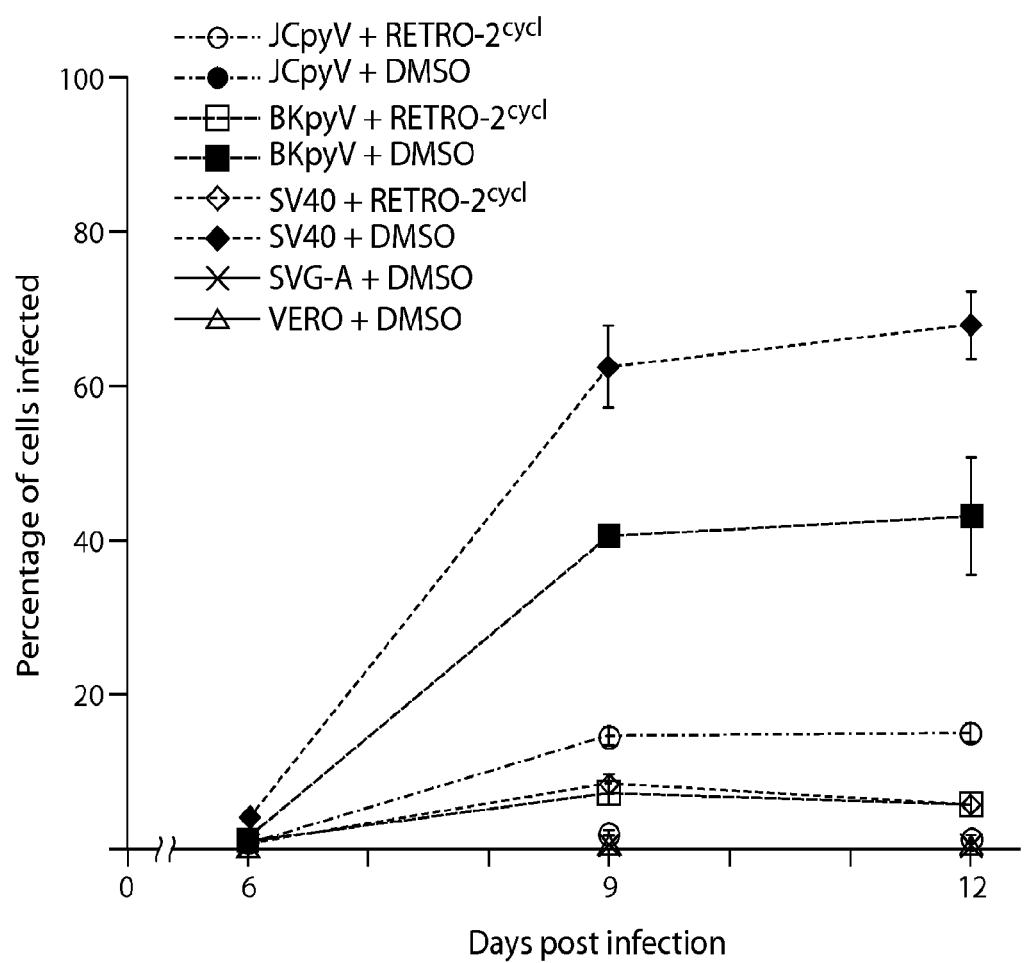
FIG. 4 depicts a reduction in viral loads of polyomavirus (JCV, BKV, SV40) infected cells treated with Retro-$2^{cycl}$. Retro-$2^{cycl}$ treated cultures release less infectious virus into culture media. Tissue culture media from the infected cultures in FIG. 3 was harvested every three days and used to infect nave cells that were not treated with Retro-$2^{cycl}$. Data represents the mean of three replicates and error bars indicate standard deviation.

Treatment of infected cells with Retro-$2^{cycl}$ also reduces the amount of infectious virons released into the tissue culture media. See FIG. 4. At 6, 9, and 12 days post infection, the tissue culture supernatant (of FIG. 3) was removed, and 0.1 mL of each sample was added to uninfected cells. After 72 h, these cells were assayed by flow cytometry to determine the percentage of cells that are infected in each sample. Error bars denote standard deviation. The data demonstrates Retro-$2^{cycl}$ treatment results in significantly less virus being produced in culture.

Figure 5A:
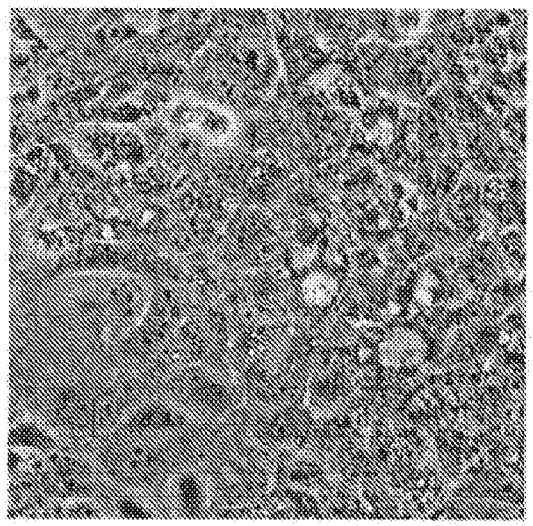
FIGS. 5A-5B depicts inhibition of JCV induced cytopathic effects in cells treated with Retro-$2^{cycl}$ (FIG. 5A) or with the DMSO vehicle control (FIG. 5B).
Figure 5B:
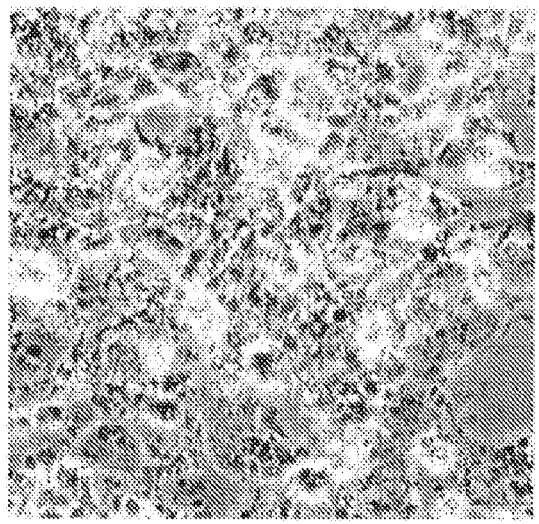

Retro-$2^{cycl}$ also reduces cytopathic effect in SVG-A cells. See FIG. 5. JCV infected SVG-A cells (of FIG. 3) at that were maintained for 12 days with Retro-$2^{cycl}$ or DMSO were detached and seeded into new tissue culture wells and were maintained in media containing Retro-$2^{cycl}$ or DMSO. At 15 days post infection these cells were imaged by phase contrast microscopy.

It was further found that Retro-$2^{cycl}$ inhibits early steps in infectious entry of JCV, BKV, or SV40. See FIG. 6. In order to determine which steps in viral entry are affected by Retro-$2^{cycl}$ treatment of cells, cells were incubated with JCV, BKV, or SV40 at 4 degrees for 1 h to prevent endocytosis. Cells were washed and then media lacking or containing Retro-$2^{cycl}$ (0 h time point) was added and the cells were incubated at 37 degrees. At the indicated time points, media was removed and replaced with media containing Retro-$2^{cycl}$. Cells were then incubated at 37 degrees for a total of 72 h and assayed by flow cytometry for the percentage of infected cells as compared to a vehicle treated negative control. Error bars denote standard deviation. The data demonstrates Retro-$2^{cycl}$ loses most of its inhibitory effect after 12 hours (14 hours for JCV), suggesting Retro-$2^{cycl}$ blocks steps in viral trafficking.

Figure 7:
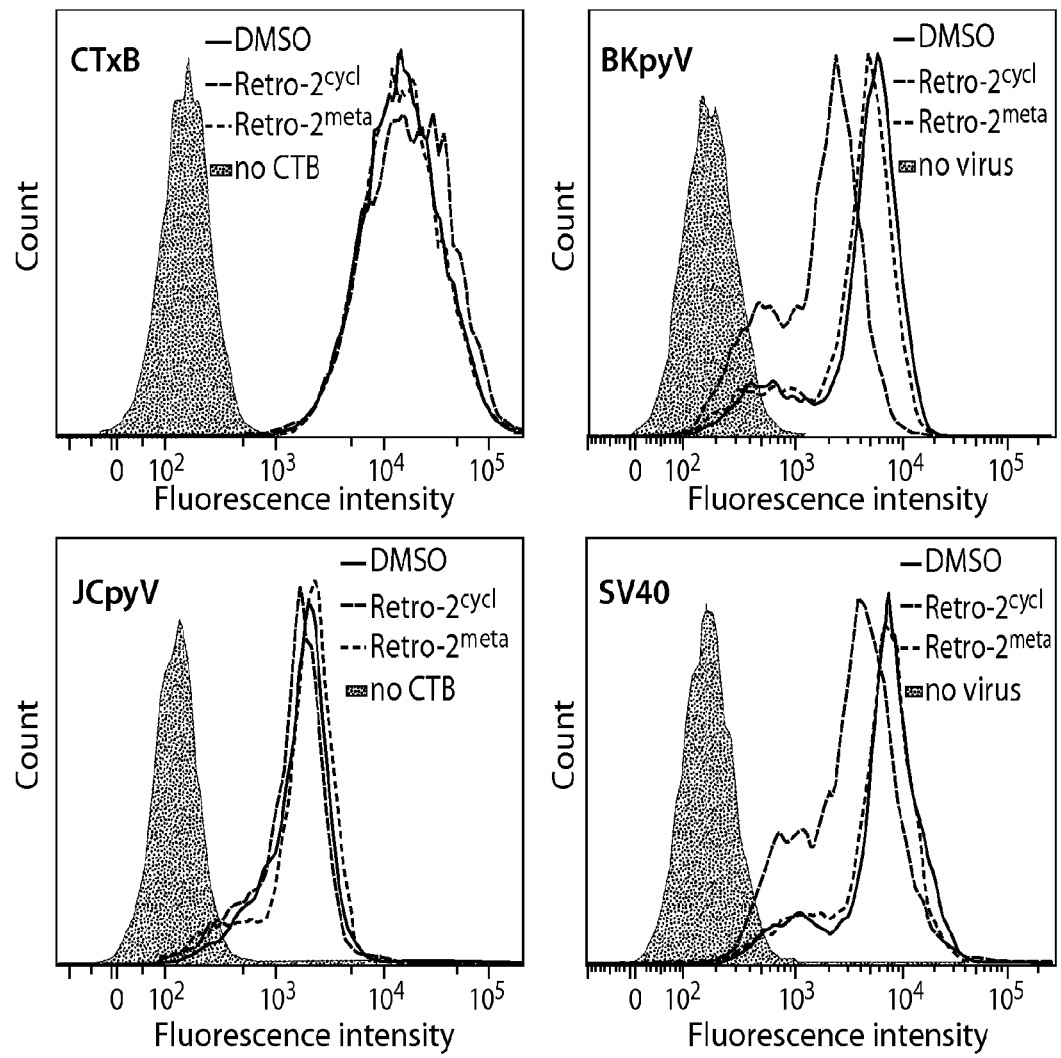
FIG. 7 depicts the lack of inhibition of cell binding by polyomaviruses or cholera toxin B subunit in cells pretreated with Retro-$2^{cycl}$.
Figure 8A:
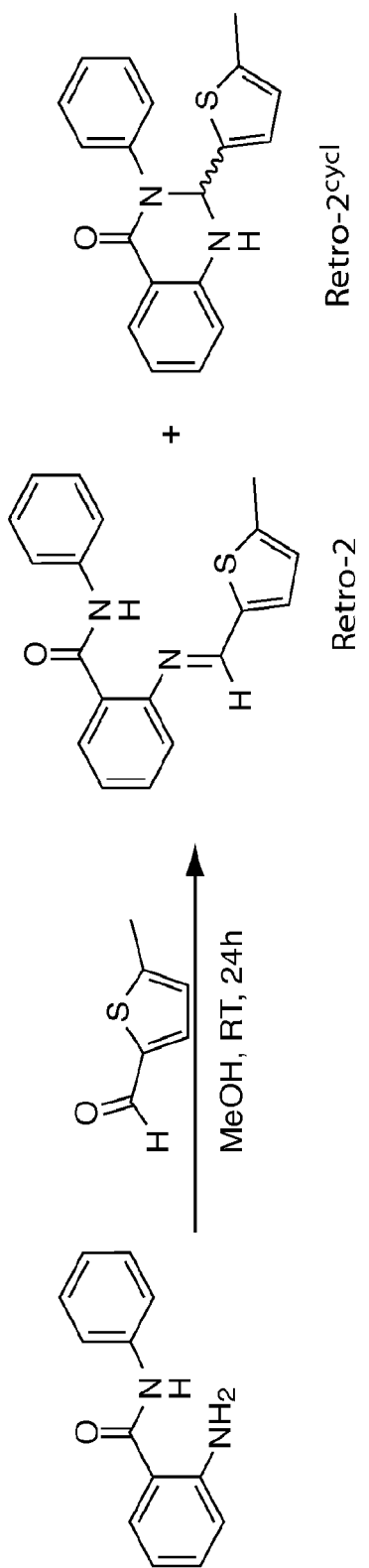
FIGS. 8A-8E depict the structures and inhibitory activities of Retro-2 analogs.
Figure 8B:
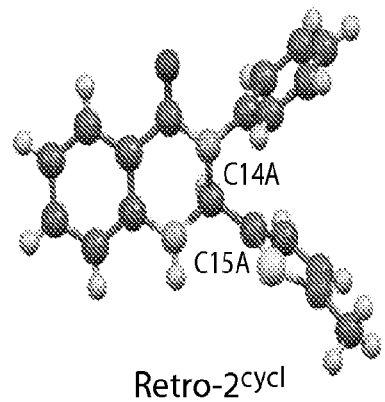
Figure 8C:
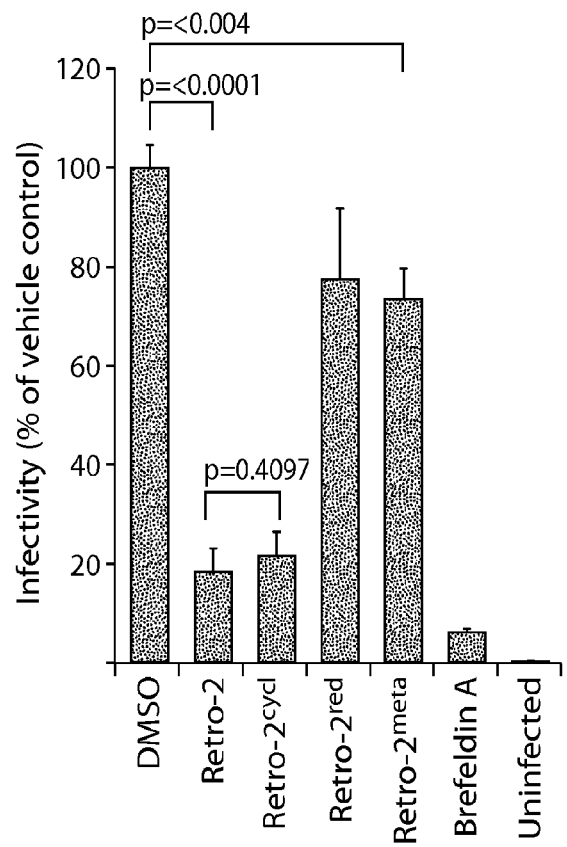
Figure 8D:
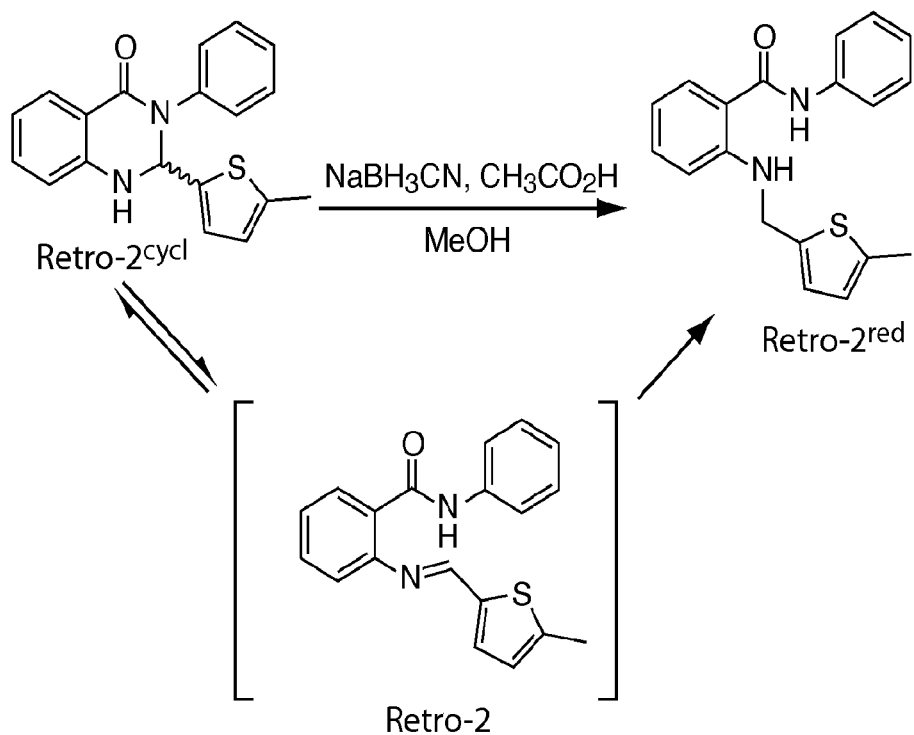
Figure 8E:
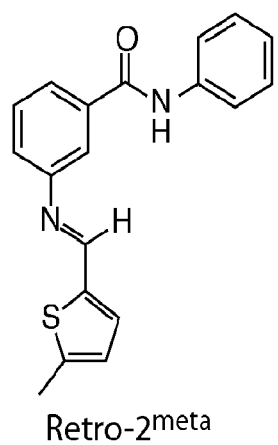

It was also found that Retro-$2^{cycl}$ treatment of cells does not prevent binding of Alexa Fluor 633 labeled JCV (JCV-633). See FIG. 7. SVG-A cells were pretreated with the 100 µM of Retro-$2^{cycl}$ at 4 degrees for 1 h prior to incubation with JCV-633 for 1 h at 4 degrees. Vero cells were pretreated with 100 µM of Retro-$2^{cycl}$ at 4 degrees for 1 h prior to incubation with BKV-633, SV40-633, or CTxB-488 for 1 h at 4 degrees Cells were then assayed by flow cytometry to determine the level of polyomavirus or toxin binding as compared to cells treated with a vehicle control.

Other analogs, such as the ethyl analog of Retro-$2^{cycl}$, were explored. See FIG. 8. Cells were inoculated with JCV at an MOI of approximately 1 for 1 h at 37 degrees. After 1 h, media was added containing analog compounds at 100 µM (FIG. 8) in a final DMSO concentration of 0.04%. After 72 h, cells were assayed by flow cytometry for infected cells and data was normalized to infected cells treated with the DMSO vehicle. Error bars denote standard deviation. The data demonstrate that Retro-2$^{cycl}$ inhibit infection of cells by polyomaviruses.

Figure 10A:
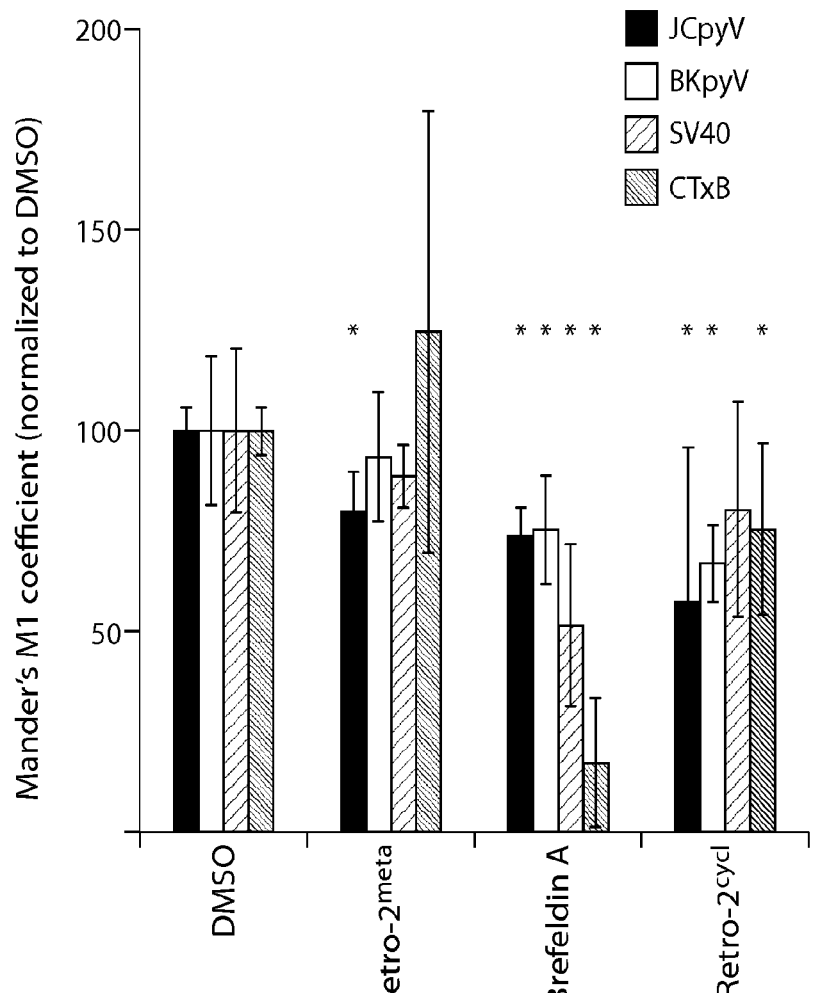
FIGS. 10A-10C depict Retro-2$^{cycl}$ inhibits ER trafficking of polyomaviruses.
Figure 10B:
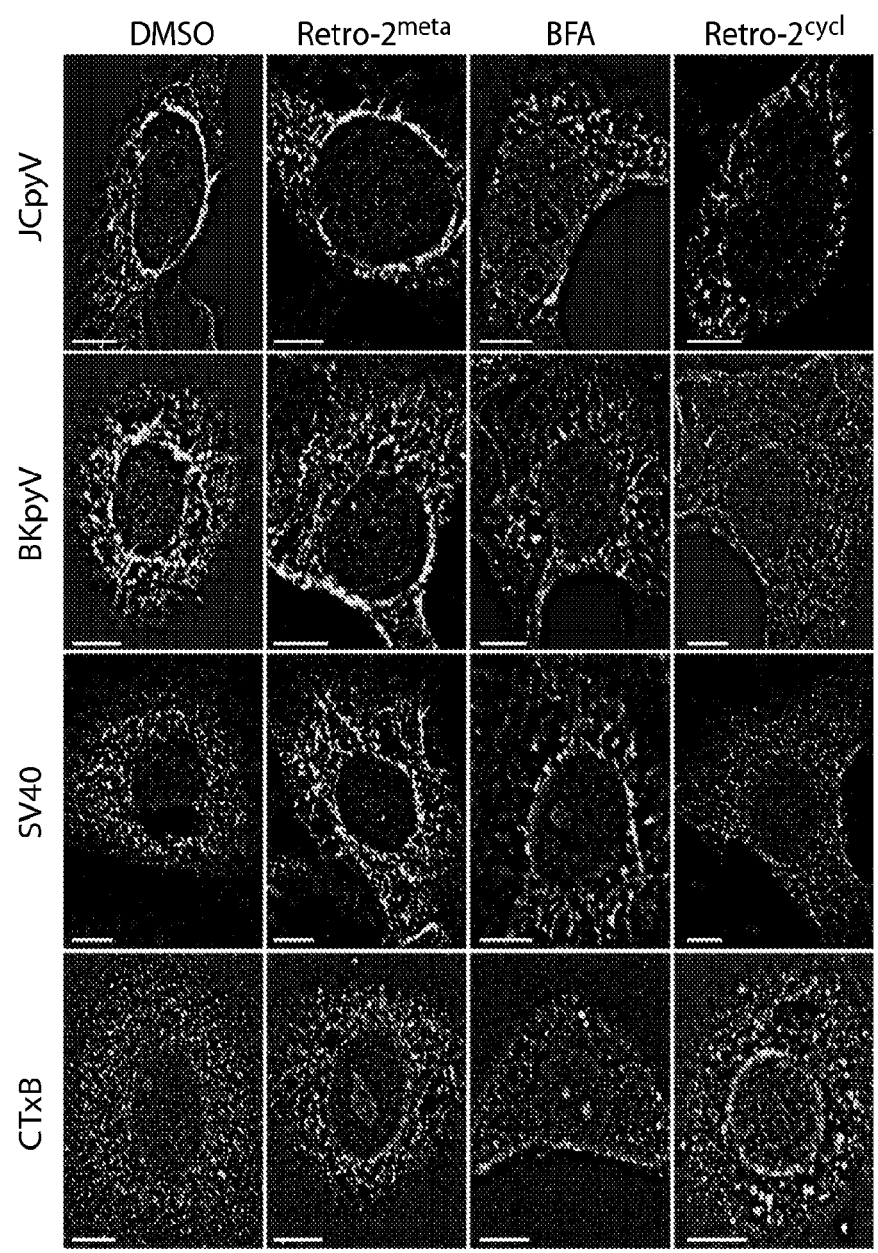
Figure 10C:
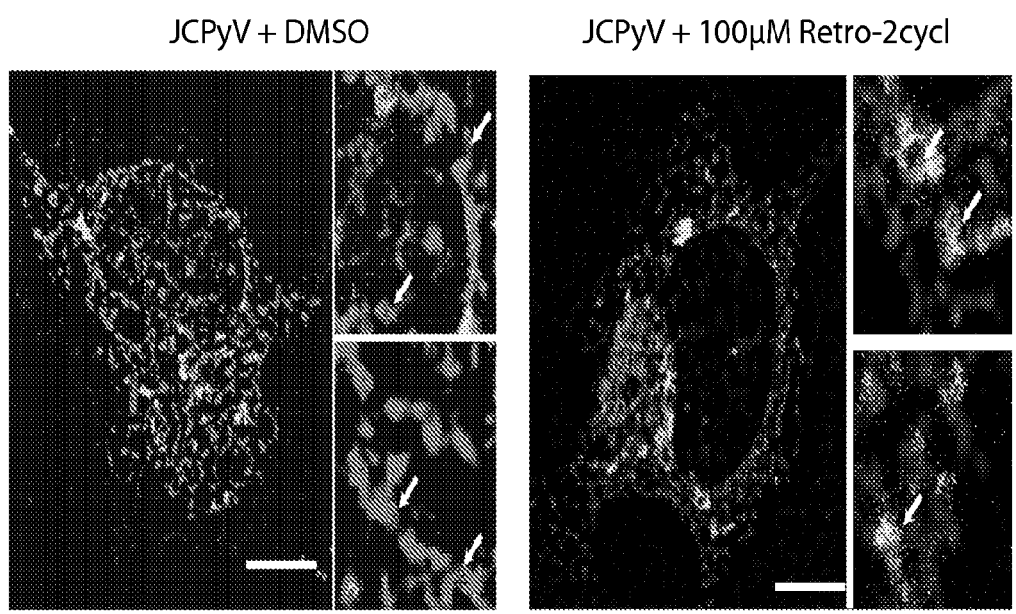
Figure 11A:
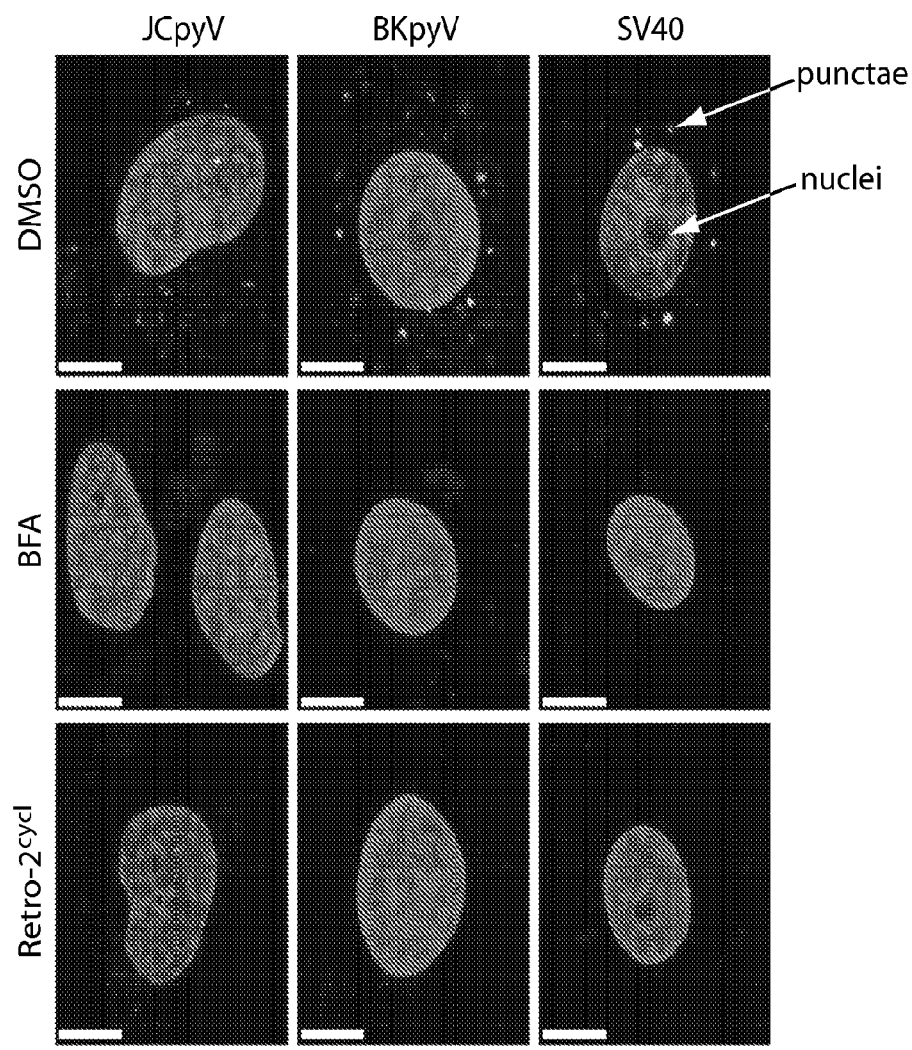
FIG. 11A-11C depict Retro-2$^{cycl}$ inhibits VP2 exposure of polyomaviruses.
Figure 11B:
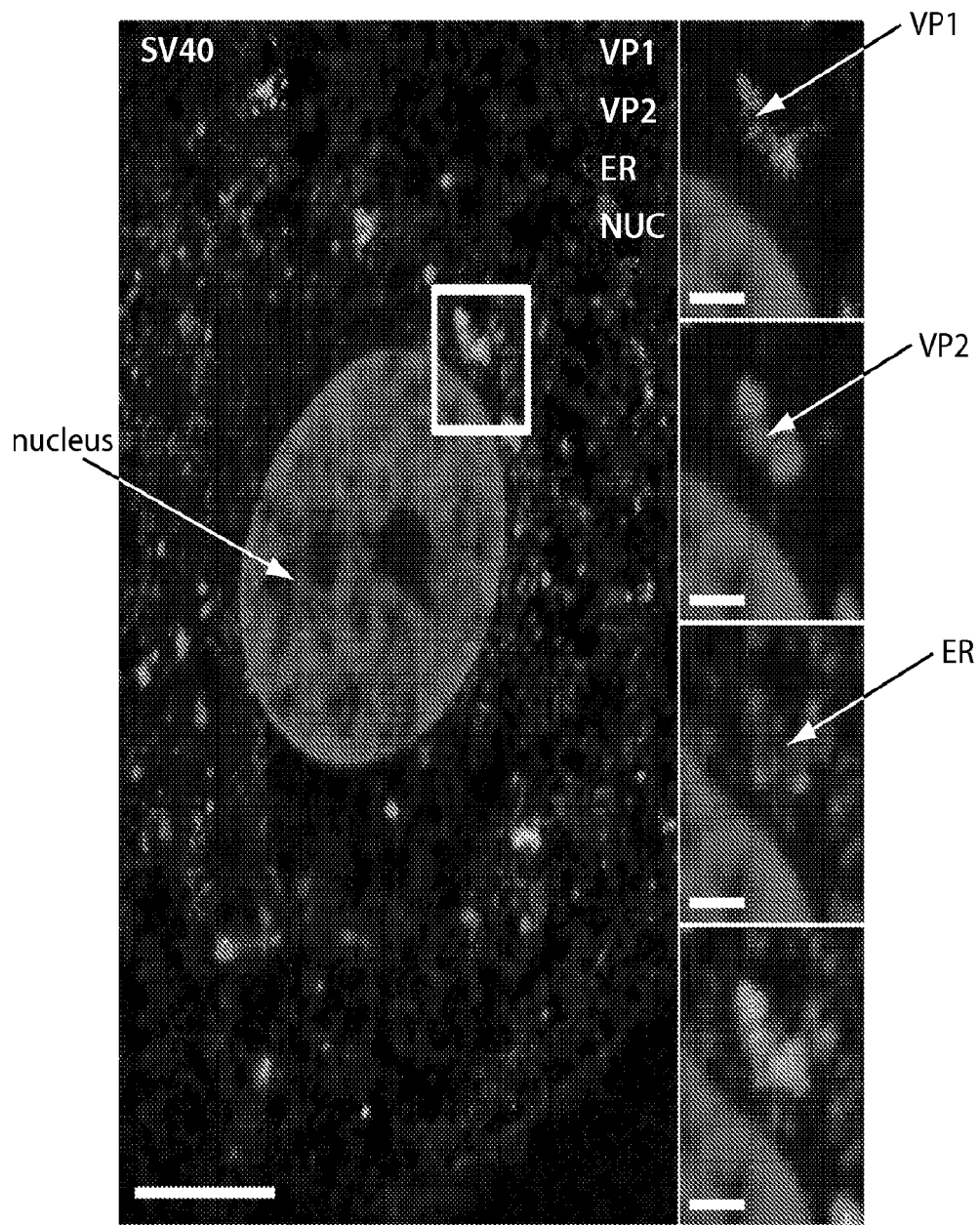
Figure 11C:
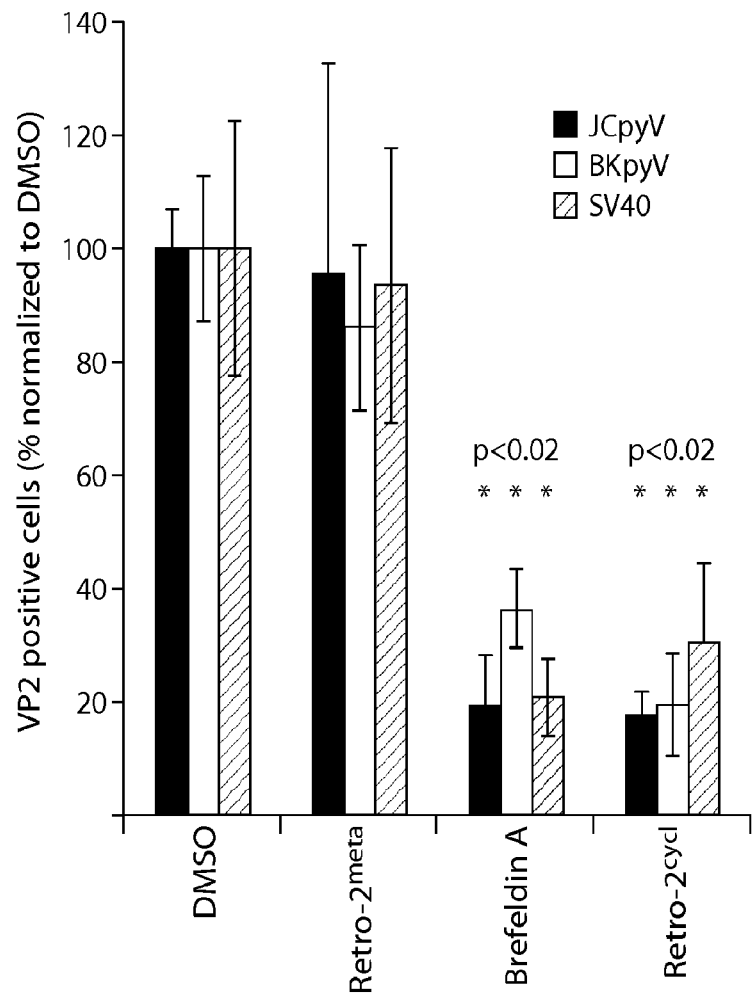

We questioned whether Retro-2$^{cycl}$ prevents polyomavirus ER trafficking. See FIGS. 10 and 11. Cells were chilled to 4 degrees C. and inoculated with labeled JCV. After inoculation, the cells were fixed at 6 hpi, the ER was immunostained with an antibody to protein disulfide isomerase (an ER resident enzyme) and imaged by confocal microscopy. The data demonstrates that Retro-2$^{cycl}$ treatment appears to decrease co-localization of JCV with the ER. Alternatively cells were transfected with early endosomal and ER markers [Early endosome (Rab5-RFP) in green; Endoplasmic reticulum (CFP-HO) in blue; JCV in red]. Transfected cells were then inoculated with JCV-633 and incubated for 6 h prior to confocal imaging. This experiment further demonstrates that Retro-2$^{cycl}$ treatment reduced ER colocalization and increases co-localization of JCV-633 with Rab5 endosomes, and thus prevents JCV from reaching the endoplasmic reticulum in cells (FIG. 10C). FIG. 10A depicts the quantification of the data shown in FIG. 10B, demonstrating that Retro-2$^{cycl}$ decreases ER trafficking of JCV.

A Retrograde Trafficking Inhibitor of Ricin and Shiga-Like Toxins Inhibits Infection of Cells by Human and Monkey Polyomaviruses Human polyomaviruses are widespread pathogens that establish persistent lifelong infections in their hosts. See, e.g., Jiang et al., J Virol (2009) 83: 1350-1358, Kean et al., PLoS Pathog (2009) 5: e1000363. Infection of immunocompetent individuals by polyomaviruses usually results in asymptomatic infection, with occurrence of disease only in immunosuppressed individuals. See, e.g., Jiang et al., J Virol (2009) 83: 1350-1358. Two human polyomaviruses, JC polyomavirus (JCPyV) and BK polyomavirus (BKPyV), establish persistent infections early in life and chronically infect cells of the kidney, urinary tract, tonsillar stromal cells, and bone marrow derived cells. See, e.g., Monaco et al., J Virol (1996) 70: 7004-7012; Monaco et al., J Virol (1998) 72: 9918-9923; Ferenczy et al., Clin Microbiol Rev (2012) 25: 471-506; Shinohara et al., J Med Virol (1993) 41: 301-305. The seroprevelence of JCPyV and BKPyV are 50% and 80% respectively. See, e.g., Chesters et al., J Infect Dis (1983) 147: 676-684; Egli et al., J Infect Dis (2009) 199: 837-846; Knowles et al., J Med Virol (2003) 71: 115-123; Knowles et al., Adv Exp Med Biol (2006) 577: 19-45. It is likely that JCPyV and BKPyV persistently replicate at low levels, as virus is sporadically detected in the urine of 30% of individuals tested. See, e.g., Kitamura et al., J Infect Dis (1990) 161: 1128-1133; Yogo et al., J Virol (1990) 64: 3139-3143; Kahan et al., Am J Clin Pathol (1980) 74: 326-332. Under conditions of immunosuppression, such as acquired immunodeficiency syndrome (AIDS) or immunomodulatory therapy, increased replication of JCPyV results in dissemination of virus to the central nervous system. See, e.g., Ferenczy et al., Clin Microbiol Rev (2012) 25: 471-506. After crossing the blood brain barrier, lytic infection of oligodendrocytes by JCPyV results in the fatal demyelinating disease progressive multifocal leukoencephalopathy (PML). See, e.g., Stoner et al., Proc Natl Acad Sci USA (1986) 83: 2271-2275; Zurhein et al., Science (1965) 148: 1477-1479; Khalili et al., Mult Scler (2006) 12: 133-142. The incidence of PML in AIDS patients is between 3% and 5% and the incidence in patients receiving immunomodulatory therapies is between 0.2% and 0.4%. See, e.g., Ferenczy et al., Clin Microbiol Rev (2012) 25: 471-506. BKPyV-associated disease is most often seen in the context of renal transplantation, where immunosuppressive therapies result in increased replication of BKPyV in the transplanted kidney leading to hemorrhagic cystitis and polyomavirus nephropathy (PVN). See, e.g., Boothpur et al., J Clin Virol (2010) 47: 306-312. The incidence of PVN in transplant recipients can be as high as 10%, often resulting in loss of the transplanted kidney. See, e.g., Binet et al., Transplantation (1999) 67: 918-922.

There are no effective anti-viral therapies to combat infection by these polyomaviruses. Polyomaviruses are small, non-enveloped, double stranded DNA viruses that replicate in the nucleus. Despite being structurally simple viruses, polyomaviruses utilize a complex and incompletely understood entry process in order to effect nuclear trafficking. After binding to cellular receptors on the cell surface, polyomaviruses enter the classical endocytic pathway, first trafficking in early and then late endosomes. See, e.g., Engel et al., J Virol. (2011) 85:4198-4211; Liebl et al., J Virol (2006) 80: 4610-4622; Querbes et al., J Virol (2006) 80: 9402-9413; Qian et al., PLoS Pathog (2009) 5: e1000465. From early or late endosomes, all polyomaviruses studied to date then undergo retrograde trafficking to the ER, where they interact with and utilize ER resident host chaperones to promote infection. See, e.g., Sapp et al., Virology (2009) 384: 400-409. Interaction of virions with ER chaperones results in partial disassembly of the capsid and retrotranslocation of the virion into the cytosol. See, e.g., Schelhaas et al., Cell (2007) 131: 516-529; Lilley et al., J Virol (2006) 80: 8739-8744; Magnuson et al., Mol Cell (2005) 20: 289-300; Rainey-Barger et al., J Virol (2007) 81: 12996-13004; Goodwin et al., mBio (2011) 2:3 e00101-11.

Despite the importance on ER trafficking, the specific host cellular machinery utilized to promote ER targeting of virions remains unclear. Many polyomaviruses, including BKPyV, simian virus 40 (SV40), and some strains of JCPyV utilize gangliosides as receptors for binding and entry into cells. See, e.g., Low et al., J Virol (2006) 80: 1361-1366; Campanero-Rhodes et al., Journal of Virology (2007) 81: 12846-12858; Tsai et al., EMBO (2003) J 22: 4346-4355; Gorelik et al., J Infect Dis (2011) 204: 103-114. Similarly, bacterial and plant toxins such as ricin, shiga-like toxins (SLTs), and cholera toxin β subunit (CTxB), bind glycolipids and undergo retrograde trafficking, resulting in accumulation of toxins in the Golgi apparatus and ER. See, e.g., Johannes et al., Cell (2008) 135: 1175-1187. It is likely that binding to glycolipids plays an important role in recruiting host cell machinery that results in accumulation of polyomaviruses and toxins in the ER. See, e.g., Ewers et al., *Cold Spring Harb Perspect Biol* 2011; doi: 10.1101/cshperspect.a004721; Sandvig et al., International Journal of Medical Microbiology (2004) 293: 483-490. Studies have demonstrated that bacterial toxins usurp a large number of host factors to facilitate retrograde trafficking, including vesicle coat proteins such as the retromer complex, clathrin and epsinR, and the vesicle fusion proteins syntaxin 5 and 6. See, e.g., Johannes et al., Cell (2008) 135: 1175-1187. Whether polyomaviruses also utilize similar host factors to undergo ER trafficking remains unclear.

Treatment of cells with brefeldin A (BFA), an inhibitor that blocks COPI mediated Golgi to ER trafficking, inhibits retrograde trafficking of toxins and protects cells from intoxication. See, e.g., Mallard et al., The Journal of Cell Biology (1998) 143: 973-990; Donta et al., The Journal of Infectious Diseases (1995) 171: 721-724. Polyomavirus infectivity is also inhibited by BFA treatment and also results in decreased accumulation of virions in the ER. See, e.g., Richards et al., Mol Biol Cell (2002) 13: 1750-1764; Norkin et al., J Virol (2002) 76: 5156-5166; Gilbert et al., Journal of Virology (2004) 78: 12259-12267; Damm et al., J Cell Biol (2005) 168: 477-488; Nelson et al., Virology (2012) 428: 30-40. However, BFA treatment of cells results in significant morphological and physiological changes, and it is unclear whether BFA treatment inhibits retrograde trafficking of polyomaviruses and toxins by similar mechanisms. See, e.g., Lippincott-Schwartz et al., Cell (1989) 56: 801-813; Huotari et al., The EMBO Journal (2011) 30: 3481-3500; Misumi et al., The Journal of Biological Chemistry (1986) 261: 11398-11403; Low et al., The Journal of Biological Chemistry (1991) 266: 17729-17732. Additionally, no polyomavirus has been found to associate with the Golgi apparatus, suggesting that there are differences in pathways or kinetics used by these molecules to target the ER.

In this study we demonstrate that a small molecule, referred to as Retro-2$^{cycl}$ potently inhibits infection of tissue culture cells by JCPyV, BKPyV, and SV40. Retro-2$^{cycl}$ was previously identified by high throughput screening for small molecules that would inhibit intoxication of host cells by ricin and SLTs. See, e.g., Stechmann et al., Cell (2010) 141: 231-242. This compound was shown to prevent retrograde trafficking from endosomes to the Golgi apparatus and subsequent steps in toxin trafficking, thus preventing intoxication of host cells. Rather than binding to the toxins, Retro-2$^{cycl}$ appears to interfere with retrograde trafficking of cargo by interaction with an unidentified cellular host factor. Unlike BFA, Retro-2$^{cycl}$ does not alter cellular compartment morphology, as the only cellular factors to have altered cellular distribution after Retro-2$^{cycl}$ treatment were syntaxin 5 and 6. Furthermore, Retro-2$^{cycl}$ is non toxic when administered to mice at levels that protect against ricin challenge, suggesting that this compound is well suited for drug development. In this study, we demonstrate that Retro-2$^{cycl}$ inhibits polyomavirus infection by interfering with ER trafficking. This suggests that polyomaviruses and ricin/SLT toxins share a dependency on similar host factors for successful intracellular trafficking. Further optimization of this compound should result in the development of effective antiviral compounds that inhibit polyomavirus replication and reduce polyomavirus-associated diseases.

Inhibition of Polyomavirus Infection in a Dose Dependent Manner

We purchased Retro-2 (later determined to be Retro-2$^{cycl}$, see following discussion) from Chembridge and pre-treated cells permissive for each type of virus (SVG-A for JCPyV, and Vero for SV40 and BKPyV), with non-toxic concentrations of Retro-2$^{cycl}$. Cells were then inoculated with JCpyV, BKpyV or SV40 in the presence of this drug and infected cells were scored by flow cytometry. Treatment with the compound purchased resulted in a dose dependent decrease in the percentage of cells expressing the viral late capsid gene VP1 compared to a vehicle control, with a calculated EC$_{50}$ of 28.4 µM, 61.2 µM, and 58.6 µM for JCPyV, BKPyV, and SV40 respectively. See FIG. 1. The compound purchased also decreased expression of the viral early gene large T antigen with similar EC$_{50}$ values (data not shown). As a control, we pre-treated Vero cells with the compound purchased and inoculated them with an adenovirus pseudovirus packaging a GFP reporter plasmid (Ad5-GFP), a virus that does not utilize retrograde trafficking for productive infection. See, e.g., Meier et al., J Gene Med (2004) 6 Suppl 1: S152-163. Treatment did not inhibit transduction, suggesting that the effect of the compound on infection is specific to virions that undergo retrograde trafficking. See FIG. 1B.

Reduction of Viral Spread in Established Tissue Culture Infections

Since most individuals are already persistently infected with JCPyV or BKPyV prior to immunosuppression, we sought to determine whether the compound purchased could prevent viral spread in tissue cultures during established infections. We infected SVG-A or Vero cells with JCPyV, BKPyV or SV40 at a low multiplicity of infectivity (MOI) of 0.01. Following one round of productive infection, 100 µM of the compound was added to these cells, which were then maintained in media containing the compound, re-feeding samples daily with fresh media containing 100 µM of the compound. Treatment of cells with the compound resulted in a significant reduction in the percentage of infected cells as compared to samples treated to vehicle control. This effect was most striking at 12 days post infection, where the compound severely diminished viral spread for SV40 (84% inhibition), BKPyV (89%), and JCPyV (90.5%). See FIG. 3 To examine whether treatment of these cultures with the compound inhibited virion production, the supernatants from each time point were used to re-infect naïve cells and the percentage of infected cells were determined. This assay showed that cultures that were previously treated with the compound produced significantly less infectious virions into the tissue culture supernatant. See FIG. 4. These results demonstrate that the compound decreases cell-to-cell spread of polyomaviruses in previously infected cultures.

The Bioactive Compound is a Dihydroquinazolinone Derivative of Retro-2

Condensation of 2-aminobenzanilide with 4-methyl-2-thiophencarboxaldehyde following the method reported in PCT/IB2009/006334 yielded a mixture of two products both having the expected molecular weight for Retro-2. See FIG. 8A. The two compounds were separated and independently characterized. One product was Retro-2 as indicated by a characteristic singlet at 11.0 ppm for the imine proton (data not shown). The second product was revealed to be a dihydroquinazolinone by x-ray diffraction crystallography, referred to as Retro-2$^{cycl}$. See FIG. 8B. The spectroscopic data for the compound purchased from Chembridge was identical to that of the dihydroquinazolinone derivative, Retro-2$^{cycl}$, and not of the structure reported for the acylic compound, Retro-2. To test the inhibitory effects of these compounds on JCPyV infection, we pre-incubated SVG-A cells with 100 µM of Retro-2 or Retro-2$^{cycl}$, and infected cells with JCpyV and scored infections by flow cytometry. As a positive control, we also treated cells with brefeldin A (BFA), a drug that inhibits COP1 mediated retrograde trafficking and has previously been shown to prevent ER trafficking of polyomaviruses. See, e.g., Richards et al., Mol Biol Cell (2002) 13: 1750-1764. Surprisingly, both Retro-2 and Retro-2$^{cycl}$ inhibited polyomavirus infection with similar efficacy. See FIG. 8C. Treatment of cells with 20 ng/mL of brefeldin A resulted in a 96% reduction in infectivity. See FIG. 8C.

Imine species similar in structure to Retro-2 are commonly invoked as mechanistic intermediates in the formation of dihydroquinazolinones, which suggests that the two chemical species could interconvert in the infectivity assay thus accounting for their similar biological activities. See, e.g., Narasimhulu et al., Tetrahedron (2011) 67: 9627-9634; Prakash et al., Org Lett (2012) 14: 1896-1899; Sharma et al., J Org Chem (2012) 77: 929-937; Shaterian et al., Synthetic Communications (2010) 40: 1231-1242; Wang et al., Chinese Chemical Letters (2011) 22: 1423-1426. Accordingly, we found that treatment of Retro-2 with scandium (III) triflate, in methanol resulted in rapid conversion to the Retro-$2^{cycl}$. In aqueous media, Retro-2 most likely cyclizes into Retro-$2^{cycl}$ as well. During the preparation of this manuscript, another group reported that Retro-2 slowly cyclizes in methanol to Retro-$2^{cycl}$, and that Retro-$2^{cycl}$ was able to protect cells from Ricin and Stx2.

Despite the observation that Retro-2 spontaneously cyclizes in polar protic solvents, it was still unclear whether the biologically active compound was Retro-2 or Retro-$2^{cycl}$. Treatment of Retro-$2^{cycl}$ with sodium cyanoborohydride in methanol slowly produced a reduced species (Retro-$2^{red}$), which indicated that cyclization is reversible and that Retro-2 and Retro-$2^{cycl}$ exist in equilibrium. See FIG. 8D. However, despite their structural similarities, Retro-$2^{red}$ is significantly less active than Retro-2. See FIG. 8C. We also prepared a Retro-2 regioisomer wherein the carboxamide and imine moieties are meta substituted (Retro-$2^{meta}$) therefore precluding cyclization. See FIG. 8E. This compound was also significantly less active and served as a useful negative control in subsequent experiments. Together, the lack of biological activity intrinsic to Retro-$2^{red}$ as well as Retro-$2^{meta}$ has lead us to the conclusion that the chemical species responsible for inhibition of polyomavirus infection is in fact the dihydroquinazolinone, Retro-$2^{cycl}$.

Retro-$2^{cycl}$ Inhibits Polyomavirus at Early Time Points During Infection

We hypothesized that Retro-$2^{cycl}$ inhibits polyomavirus trafficking to the ER, since the drug inhibits retrograde trafficking of ricin and SLTs from endosomes to the Golgi apparatus. SVG-A or Vero cells were synchronously infected with JCPyV, BKPyV, or SV40, and Retro-$2^{cycl}$ was added to cells at the indicated time points and the amount of infectivity was compared to vehicle control. The results show that addition of Retro-$2^{cycl}$ at time points up to 4 hours post infection (hpi) significantly reduces infectivity, with a progressive loss in its inhibitory effect at time points after 6 hpi. See FIG. 6. By 18 hpi, greater than 80% of infectivity has been regained. The kinetics of these effects are consistent with previous reports showing that polyomaviruses colocalize with ER markers at 6-16 hpi See, e.g., Nelson et al., Virology (2012) 428: 30-40. Therefore, the protective effect of Retro-$2^{cycl}$ is lost following time points consistent with localization to the ER, suggesting that this compound acts to limit polyomavirus trafficking to this compartment.

Retro-$2^{cycl}$ does not Prevent Attachment or Entry of JCPyV into Host Cells

Figure 9:
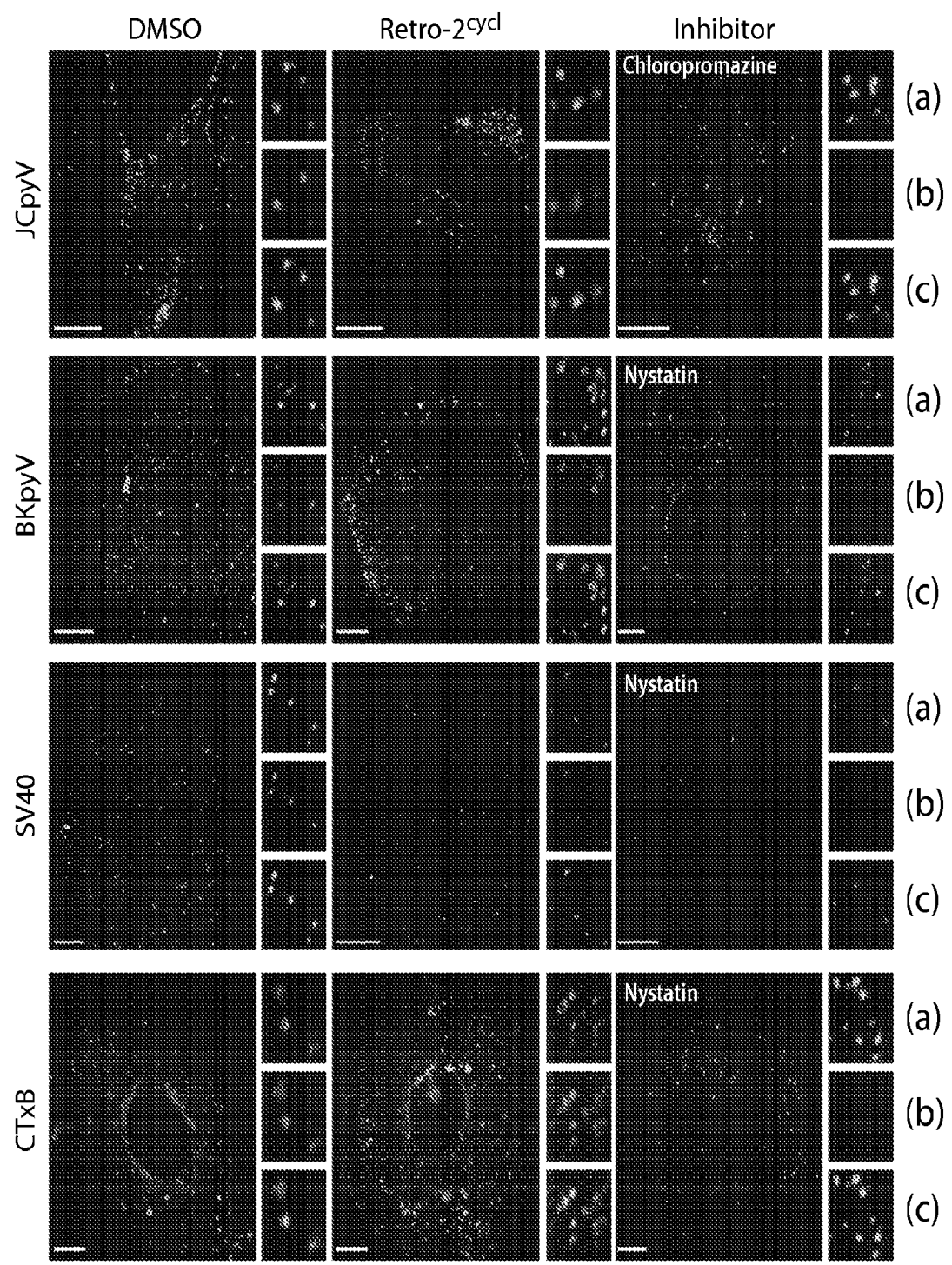
FIG. 9 depicts endocytosis of polyomiruses is not inhibited by treatment with Retro-2$^{cycl}$. Cells were chilled to prevent endocytosis, and Alexa fluor 488 labeled J$^{CpyV}$, BKpyV, or SV40 was bound to cells for 1 h on ice. Unbound virus was removed by extensive washing and samples were heated for 120 min prior to fixation. Cells were imaged by confocal microscopy and images were captured before (green, labeled a) and after (red, labeled b) trypan blue addition to samples. Trypan blue will quench the fluorescence of solvent accessible virions, resulting in internalized virions being pseudocolored yellow (labeled c).

To test whether Retro-$2^{cycl}$ inhibits steps upstream of endosomal to ER trafficking, we pretreated SVG-A or Vero cells with Retro-$2^{cycl}$ and assayed for attachment using Alexa fluor 633 labeled JCPyV, BKPyV, or SV40. Pretreatment of cells for 1 h with 100 μM Retro-$2^{cycl}$ resulted similar levels of binding of JCpyV or CTxB to cells compared to the vehicle control treated cells. See FIG. 9. We did see slight decreases in the binding of BKpyV and SV40 to cells, but significant virions still bound to cells and the protective effect of Retro-$2^{cycl}$ was not lost at these time points, suggesting that this was not the major mechanism by which Retro-$2^{cycl}$ protects cells from infection. We next sought to determine whether Retro-$2^{cycl}$ could prevent endocytosis of virions. To assay for endocytosis, we pre-treated cells with Retro-$2^{cycl}$, a DMSO vehicle control, chloropromazine (an inhibitor of JCpyV endocytosis), or nystatin (an inhibitor of BKpyV, SV40, and CTxB endocytosis) prior to inoculation with Alexa fluor 488 labeled JCPyV, BKPyV, SV40, or CTxB. After washing, these samples were warmed to allow for synchronous endocytosis and fixed at 2 h. To determine whether virions were internalized or still present on the plasma membrane, we imaged these samples (pseudocolored green), then added trypan blue and re-imaged the samples (pseudocolored red). Trypan blue is a membrane impermeable dye that quenches the fluorescence of virions on the plasma membrane. Therefore, virions that have entered cells still fluoresce after addition of trypan blue and are pseudocolored yellow. This experiment demonstrates that Retro-$2^{cycl}$ treatment does not inhibit endocytosis of JCpyV, BKpyV, SV40, or CTxB. See FIG. 9. In contrast, chloropromazine inhibits endocytosis of JCpyV and nystatin treatment of cells inhibits endocytosis of BKpyV, SV40, and CTxB. Thus Retro-$2^{cycl}$ does not inhibit binding or endocytosis of polyomaviruses into host cells.

Retro-$2^{cycl}$ Reduces Retrograde Trafficking of Polyomaviruses and CTxB

Since Retro-$2^{cycl}$ prevents endosomal to Golgi trafficking of ricin, SLTs, and CTxB, we sought to determine whether treatment of cells with Retro-$2^{cycl}$ would interfere with delivery of virions or CTxB to the ER. Cells were pre-incubated with the Retro-$2^{cycl}$ or a vehicle control and then inoculated with purified JCPyV, BKPyV, SV40 or CTxB. Cells were then fixed at 8 hpi (3 hpi for cholera toxin) and immunostained for colocalization with the ER protein, protein disulfide isomerase (PDI). Treatment of cells with the vehicle control or the non-inhibitory Retro-2 analog, Retro-$2^{meta}$, results in significant colocalization between polyomaviruses or CTxB with the ER. See FIG. 10A. Conversely, treatment of cells with BFA or Retro-$2^{cycl}$ significantly reduces colocalization of JCpyV, BKpyV, or CTxB, demonstrating that these compounds inhibit ER accumulation of virions and toxins. SV40 and PDI colocalization was reduced, although this reduction was not significant. To visualize this colocalization, cells were inoculated with Alexa fluor 488 labeled JCpyV, BKpyV, or SV40 and the ER was immunostained with an antibody to PDI. In DMSO or Retro-$2^{meta}$ treated samples, colocalization between virions and PDI is visible. See FIG. 10B. At 3 hpi, perinuclear accumulation of CTxB is visible in DMSO or Retro-$2^{meta}$ treated cells. Treatment of cells with BFA or Retro-$2^{cycl}$ results in less colocalization of virions with PDI, and disperses the perinuclear accumulation of CTxB. Taken together, these results demonstrate that Retro-$2^{cycl}$ significantly reduces ER trafficking of polyomaviruses.

Retro-$2^{cycl}$ Prevents Exposure of the Viral Minor Capsid Proteins

Upon trafficking to the ER, polyomaviruses interact with host cell chaperones for productive infection. See, e.g., Tsai et al., Curr Top Microbiol Immunol (2010) 343: 177-194. These interactions result in isomeraziation of inter-pentameric disulfide bonds that normally cross-link the capsid together resulting in partial uncoating of the virion. As a result, the normally sequestered minor capsid protein VP2 is externalized and is accessible to antibodies. See, e.g., Norkin et al., J Virol (2002) 76: 5156-5166. Since Retro-$2^{cycl}$ reduces delivery of virions to the ER, we examined whether Retro-$2^{cycl}$ will also reduce exposure of the minor capsid proteins of these viruses. We inoculated cells with JCPyV, BKPyV, or SV40 in the presence of 100 μM Retro-$2^{cycl}$ or vehicle control. In cells treated with the DMSO control at 10 hpi, discrete punctae corresponding to VP2 are visualized in a perinuclear region of the cells. See FIG. 11. In contrast, treatment of cells with Brefeldin A results in a significant reduction in the number of cells with VP2 exposed, demonstrating that virions need to target the ER to release VP2.

We observed that pre-treatment of cells with Retro-2$^{cycl}$, but not the poorly neutralizing Retro-2$^{meta}$, results in a significant reduction of cells exposing VP2 to similar levels as those treated with BFA. See FIG. 11C. These punctae colocalize with the ER rather than other organelles such as lysosomes, see FIG. 11B, a result that is consistent with previous studies. See, e.g., Goodwin et al., mBio (2011) 2:3 e00101-11. Taken together, these data demonstrate that Retro-2$^{cycl}$ treatment of cells reduces ER trafficking and as a by-product, prevents exposure of the minor capsid proteins of JCPyV, BKPyV, and SV40.

Discussion

We demonstrate that the small molecule Retro-2$^{cycl}$, a recently described inhibitor of bacterial intoxication, effectively inhibits infection by three polyomaviruses. Retro-2$^{cycl}$ inhibits polyomavirus infection in a similar manner to its effects on ricin and shiga-like toxins, namely by blocking retrograde trafficking to the ER or Golgi. See, e.g., Stechmann et al., Cell (2010) 141: 231-242. This effect appears specific for viruses that utilize retrograde trafficking, as transduction of cells by an adenovirus pseudovirus is not inhibited by Retro-2$^{cycl}$. This work demonstrates that Retro-2$^{cycl}$ is not only an effective antiviral compound, but will also aid to further delineate the endocytic pathways used by polyomaviruses to target the ER.

During infection, polyomaviruses traffic to the ER where their viral capsids interact with host cell chaperones to undergo partial uncoating and utilize the ER associated degradation pathway to gain access to the cytosol. See, e.g., Tsai et al., Curr Top Microbiol Immunol (2010) 343: 177-194. We show that Retro-2$^{cycl}$ reduces ER accumulation of virions and thus prevents this critical step in the infectious lifecycle of polyomaviruses. Since virions cannot interact with ER resident chaperones, necessary uncoating steps are inhibited, as can be evidenced by a lack of exposure of the minor capsid protein VP2 in Retro-2$^{cycl}$ treated samples. All polyomaviruses studied to date undergo retrograde trafficking and in recent years 9 new human polyomaviruses have been discovered. See, e.g., Feng et al., Science (2008) 319: 1096-1100; Siebrasse et al., J Virol (2012) 86: 10321-10326; Schowalter et al., Cell Host Microbe (2010) 7: 509-515; Buck et al., J Virol (2012) 86: 10887; van der Meijden et al., PLoS Pathog (2010) 6: e1001024; Allander et al., J Virol 81: (2007) 4130-4136; Gaynor et al., PLoS Pathog (2007) 3: e64; Scuda et al., J Virol (2011) 85: 4586-4590. Several of these newly discovered viruses are associated with human diseases, including Merkel cell polyomavirus, which is the causative agent of the fatal cancer Merkel cell carcinoma. See, e.g., Feng et al., Science (2008) 319: 1096-1100. Since Retro-2$^{cycl}$ is protective against JCpyV, BKpyV, and SV40, it is likely that this compound will inhibit replication of these polyomaviruses, and will be a useful tool in verifying whether these new polyomaviruses target the ER for productive infection.

Brefeldin A is another small molecule that has been described to inhibit ER accumulation of polyomaviruses. However, BFA is highly cytotoxic to cells, making this drug less appealing for developments of antiviral or anti-toxin therapies. See, e.g., Barbier et al., Toxins (2012) 4: 15-27. Additionally, BFA treatment rapidly alters the morphology of Golgi apparatus, inhibits endosomal maturation, and inhibits protein secretion, demonstrating that this compound elicits numerous off target effects besides inhibiting retrograde trafficking. See, e.g., Lippincott-Schwartz et al., Cell (1989) 56: 801-813; Huotari et al., The EMBO Journal (2011) 30: 3481-3500; Misumi et al., The Journal of Biological Bhemistry (1986) 261: 11398-11403; Low et al., The Journal of Biological Chemistry (1991) 266: 17729-17732. Conversely, Retro-2$^{cycl}$ has been shown to cause little altered cell compartment morphology, and is well tolerated when administered to mice. See, e.g., Stechmann et al., Cell (2010) 141: 231-242. Thus, although Retro-2$^{cycl}$ is not the first described inhibitor of ER trafficking of virions, it is likely the first small molecule inhibitor of polyomavirus infectivity that shows promise as a potential antiviral therapy.

We also show that the biologically active chemical species of Retro-2 is a dihydroquinazolinone derivative of Retro-2, and not an imine as was originally reported by Stechman and colleagues. See, e.g., Stechmann et al., Cell (2010) 141: 231-242. While completing these studies, another group has confirmed that Retro-2 converts to a dihydroquinazolinone. See, e.g., Park et al., Sci Rep (2012) 2: 631. With the correct structure of the retrograde transport inhibitor now established, we can consider the medicinal chemistry optimization of Retro-2$^{cycl}$ as a potential drug lead. An in depth structure activity relationship study of Retro-2$^{cycl}$ is currently underway in our labs, and we provide herein additional Retro-2$^{cycl}$ analogs synthesized and studied. See, e.g., Table 1, provided below.

The inhibitory effect of Retro-2$^{cycl}$ is strikingly similar to the effect seen on ricin toxin and shiga-like toxins, where Retro-2$^{cycl}$ treatment prevents endosomal to Golgi trafficking, and as a consequence, also inhibits ER trafficking. See, e.g., Low et al., The Journal of Biological Chemistry (1991) 266: 17729-17732. This similarity suggest that there may be overlap in the cellular proteins used by toxins and polyomaviruses to effect ER trafficking. However, there are likely significant differences in the kinetics or pathways used by polyomaviruses and bacterial toxins to target the ER, since ricin and shiga-like toxins rapidly traffic to the Golgi apparatus, an association that has yet to be identified for any polyomavirus. See, e.g., Johannes et al., Nat Rev Microbiol (2010) 8: 105-116. This suggests the cellular host factors targeted by Retro-2$^{cycl}$ may be involved in multiple retrograde trafficking pathways, only a small proportion of virions traffic to the Golgi, or that polyomaviruses may transiently traffic through the Golgi complex prior to ER accumulation. It is unlikely that Retro-2$^{cycl}$ is affecting entry steps upstream of ER trafficking, as virions are still able to bind and enter Retro-2$^{cycl}$ treated cells. Furthermore, Retro-2$^{cycl}$ loses most of its inhibitory effect when added to synchronously infected cultures at time points after 14 hours, further demonstrating the binding and entry events are not inhibited by Retro-2$^{cycl}$ treatment. SLTs, CTxB, and some polyomaviruses bind to glycolipids, and may therefore provide some rationale as to how this compound is inhibiting trafficking. See, e.g., Ewers et al., Cold Spring Harb Perspect Biol (2011) 3:a004721. However, whereas numerous host cellular transport factors are known to promote endosomal to Golgi transport of ricin toxins and SLT, such as the retromer complex, Syntaxin 5, EpsinR, and clathrin, the role of these factors in polyomavirus entry is not known. See, e.g., Popoff et al., J Cell Sci (2007) 120: 2022-2031; Bonifacino et al., Curr Opin Cell Biol (2008) 20: 427-436. It is tempting to speculate that these same proteins play a critical role in polyomavirus ER trafficking, and future work examining the role of these host factors in polyomavirus entry will increase our understanding of this process. Retro-2$^{cycl}$ treatment causes redistribution of syntaxin 5 and 6 and previous work has demonstrated that siRNA knockdown of syntaxin 5 significantly inhibits SV40 infectivity, suggesting that redistribution of Syntaxin 5 and 6 by Retro-2$^{cycl}$ may inhibit ER trafficking of polyomaviruses. Determining what cellular host factor or factors Retro-2$^{cycl}$ is binding will significantly increase our understanding as to how polyomaviruses and toxins undergo retrograde trafficking.

It is unlikely that Retro-2$^{cycl}$ binds to polyomaviruses directly, and therefore should decrease the likelihood of escape mutations, since infectious mutants would have to utilize alternate trafficking pathways to ultimately deliver their genome to the nucleus for productive replication. Since the majority of people are persistently infected with JCpyV and BKpyV, the ability of Retro-2$^{cycl}$ to reduce the spread of JCPyV, BKPyV, and SV40 in established infections suggests that these compounds may be efficacious in controlling viral dissemination in previously infected individuals. Further optimization of Retro-2$^{cycl}$ should result in effective antiviral therapies to treat or prevent diseases caused by human polyomaviruses or other pathogens that utilize retrograde trafficking during infection.

Materials and Methods

Cells, Viruses, Plasmids, and Antibodies

SVG-A cells were maintained in complete media (minimal essential media containing 10% fetal bovine serum 1% penicillin, 1% streptomycin) and have been previously described. See Major et al., Proc Natl Acad Sci USA (1985) 82: 1257-1261. Vero cells were purchased from the American Type Culture Collection (ATCC) and were maintained in complete media supplemented with 5% fetal bovine serum. The SVE-delta strain of JCPyV, the Dunlop strain of BKPyV, and the 777 strain of SV40 were used for these studies, and have been described previously or were purchased from ATCC. See Vacante et al., Virology (1989) 170: 353-361. Alexa Fluor 488 labeled cholera toxin was purchased from Invitrogen. Antibodies to protein disulfide isomerase and VP2 were purchased from Abcam. The PAB597 and PAB962 hybridoma was a kind gift from Ed Harlow. The mouse monoclonal antibody to SV-40 large T-antigen (AB-2) was purchased from Calbiochem.

Virus Purification and Labeling

JCPyV, BKPyV, and SV40 were purified similar to previously published methods. See, e.g., Shen et al., Virology (2011) 411: 142-152. Briefly, ten 1700 cm$^2$ roller bottles were seeded with SVG-A cells at 50% confluency and infected with JCPyV, BKPyV, or SV40 at an MOI of ~0.1 FFU/cell for 14 days, with the cell culture media replaced at 7 days. Viral lysates were harvested by scraping cells in the presence of cell culture media, and this lysate was frozen and thawed 3 times. The lysate was then treated with type V neuraminidase (Sigma) at 37° C. for 1 h to release JCPyV still bound to cells. Deoxycholate acid (Fisher Scientific) was added to further disrupt cells for 1 h at 37° C. and then sonicated three times on ice (50% amplitude 50% duty cycle, power 4, 1 min). The cellular debris was pelleted by centrifugation, and the viral supernatant was pelleted through a 20% sucrose cushion in a Beckman SW40ti rotor at 150,000×g at 4° C. for 3 h. The viral pellet was resuspended into buffer A (10 mM Tris-HCl, 50 mM NaCl, 0.1 mM CaCl$_2$) and sonicated 3 times (30% amplitude 50% duty cycle, power 3, 1 min). The resuspended pellet was loaded onto a CsCl step gradient (1.29-1.35 g/ml) and spun at 115,000×g at 4° C. for 18 h in a Beckman SW55ti rotor. The band corresponding to DNA-containing virions was isolated and dialyzed extensively against buffer A. JCPyV, BKPyV, or SV40 was labeled with Alexa Fluor 488 or Alexa Fluor 633 according to the manufacturer's instructions (Invitrogen). Briefly, purified JCPyV was dialyzed in 0.1M carbonate/bicarbonate buffer pH 8 and the virus was then concentrated to ~0.5 mg/ml using a 10,000 MWCO Amicon Ultra (Millipore) and dye was added at a molar excess of 200:1. After 1 h of rocking incubation at room temperature, the excess dye was removed by extensive dialysis against buffer A.

Dose Dependent Inhibition of Infection by Retro-2$^{cycl}$

SVG-A or Vero cells were seeded into 12-well plates at a concentration of 2×10$^5$ cells per well. The next day cells were pre-treated with Retro-2$^{cycl}$ for 0.5 h, then virus was bound to cells in 0.08 mL in the presence of Retro compounds at the indicated concentration. After allowing adsorption of virions to cells for 1 h, 2 mL per well of complete media containing Retro-2 at the indicated concentration was overlaid into each well. The final concentration of DMSO in all wells was 0.04%. After allowing cells to be infected for 48 h to allow expression of large T-antigen or 72 h for VP1 expression, infected cells were scored by flow cytometry. Curve fitting was performed using Origin (OriginLab), with the non-linear curve fitting package (Growth/Sigmodial category, Dose response function), with shared and fixed parameters of 0 and 100. EC$_{50}$ values were calculated for each replicate and these values were used to generate average EC$_{50}$ data.

Flow Cytometric Scoring of Viral Infection

SVG-A or Vero cells were detached from 12-well plates by aspirating the growth media, washing adherent cells once with phosphate buffered saline (PBS), and detaching with an EDTA based non-enzymatic agent (Cellstripper). These cells were then transferred to v-bottom 96-well plates and pelleted by centrifugation at 600×g for 5 min, washed with PBS and fixed in 0.2 mL 4% paraformaldehyde (PFA) for 10 min. Cells were pelleted and washed with PBS, and permeabalized with 0.2 mL PBS containing 1% Triton X-100 for 10 min at 21° C. Cells were then pelleted and resuspended in 0.1 mL PBS containing 3% BSA and an Alexa Fluor labeled monoclonal antibody to VP1 (PAB 597-AF488) or a polyclonal antibody to large T-antigen (AB-2 for BKPyV and SV40 or JCT962 for JCPyV). After incubation for 1 h at 21° C., cells were washed once with PBS and fluorescence was read by flow cytometry on a (FACSCanto II, BD Biosciences). For large T-antigen staining, cells were washed 3 times and then stain with a secondary antibody conjugated to Alexa fluor 488 for 1 h at room temp. Uninfected cells were used to establish gates for infected cells. An infected culture without Retro compounds (~10% total infected cells) was then normalized to 100% and any reduction in infection in the Retro-2$^{cycl}$ treated cells were then compared to this untreated control. Three independent experiments were performed and used to calculate standard deviations. T-tests were used to calculated significance.

Time Course Experiments

SVG-A or Vero cells were seeded into 12-well plates in 1 mL complete media at a concentration of 2×10$^5$ cells per well. The following day, cells were chilled to 4° C. to prevent endocytosis, and virions were bound for 1 h at 4° C. SVG-A cells were infected with JCPyV, and Vero cells were infected with BKPyV, or SV40 at an multiplicity of infection (MOI) of 1. After binding, excess virus was washed away with chilled media, and samples were warmed to 37° C. At each indicated time point, media was removed, and fresh media containing Retro compounds was added to each sample. After 72 h, cells were scored for infection by flow cytometry.

Multicycle Growth Assays

Replicate 24-well plates were seeded with SVG-A or Vero cells at 25% confluency. The next day cells were infected with the appropriate virus at an MOI of 0.01 in 0.04 mL of complete media for 1 h at 37° C. After this incubation, 2 mL of compete media was then added to each well for 3 days to allow infection to be established. After 72 h, 100 μM of Retro-2 was added to each appropriate replicates. This media was aspirated and replace with fresh media containing Retro-2 daily. Replicates of each sample was fixed every 3 days and stained for VP1. At each day, the replicates containing Retro compounds were compared to the untreated controls. For the reinfection assays, the supernatants were saved and used to reinfect naïve cells. After 72 h, infected cells were then scored by flow cytometry.

Microscopy

All microscopy experiments were performed using an LSM-710 laser scanning confocal microscope with a 63× 1.4 NA plan apochromat objective with the pinhole set to one Airy unit (Carl Zeiss). DAPI was excited using a 405 nm diode laser, Alexa Fluor 488 was excited using a 488 nm argon laser and Alexa Fluor 633 was excited using a 633 nm helium-neon laser. For the endocytosis assay, SVG-A or Vero cells were seeded in #1.5 glass-bottomed 96-well plates at a density of 3×10³ cells and were incubated overnight. The following day, cells were pretreated with 100 μM Retro-2, 0.04% DMSO, 30 μM chloropromazine, or 100 μM nystatin for 30 min at 37° C. Cells were then chilled to 4° C. to prevent endocytosis, and AF488-JCpyV, BKpyV, or SV40 was added at an MOI of 1 for 1 h with rocking. Unbound virus was removed by washing with chilled medium and 1 mL of media containing the appropriate drug was then added to each well and samples were returned to the incubator for 2 h at 37° C. prior to fixation with 4% PFA. Confocal Z-series were acquired, and trypan blue was added at a final concentration of 0.008% to quench the fluorescence on non-internalized virions. After quenching, the same cell was reimaged. Fluorescence from virions prior to quenching was pseudocolored green and post quenching fluorescence was pseudocolored red. Image noise was reduced using a 3:3:3 median filter and maximal image projections generated. Images were aligned and brightness and contrast was adjusted using Adobe Photoshop. For the ER trafficking assay, cells were plated and infected similar to the endocytosis assay, with cells inoculated with Alexa fluor 488 labeled polyomaviruses at an MOI of 1. At 8 hpi (3 hpi for CTxB), cells were fixed and the endoplasmic reticulum was stained with a polyclonal antibody to PDI and visualized with an Alexa fluor 633 labeled secondary antibody. Image noise was reduced using a 3:3:3 median filter and samples were bandpassed using an FFT filter in ImageJ to enhance edges, as has previously been reported (settings: 15 pixels large structures, 3 pixels small structures, 5% tolerance). Colocalization was determined by inoculating cells with unlabeled JCpyV, BKpyV, or SV40 at an MOI of 1 or Alexa fluor 488 labeled CTxB (4 gg/ml) for 1 h, samples were wash with media containing drug, and fixed at 8 hpi. Virions were immunostained with a mouse monocolonal antibody to VP1 (PAb597) and PDI was stained with a rabbit polyclonal antibody to PDI. Colocalization was determined using Manders coefficient of colocalization, using the JACoP plugin for ImageJ. M1 values were normalized to a DMSO control and 5 cells were imaged for each condition tested.

Significance Testing was Performed Using T-Test

For the VP2 release assay, cells were seeded 12-well plates in 1 mL complete media at a concentration of 5×10⁴ cells per well and incubated overnight. The following day, cells were pretreated with 100 μM Retro-2, 0.04% DMSO, or 500 ng/mL of brefeldin A for 30 min. Samples were then inoculated with JCpyV, BKpyV, or SV40 at an MOI of 10 for 1 h with rocking at 37° C. Excess virus was washed off and samples were incubated in the presence of inhibitors and fixed at 10 hpi. These cells were then stained with a polyclonal antibody to VP2 and counter-stained with DAPI. At least ten independent fields of view were counted per sample, and three independent replicates were performed, with an average of 1700 cells counted per condition. Significance testing was performed using T-test. To visualize colocalization between VP2 and the ER, Vero cells were infected with SV40 as for the VP2 release assay. After fixation, cells were stained for VP1 using the mouse monoclonal antibody PAB597, VP2 was stained using a rabbit polyclonal antibody, and the ER was stained using a goat polyclonal antibody to PDI. The nucleus was counter-stained with BOBO-3. Image noise was reduced using a 3:3:3 median filter, and a single Z-slice was shown.

Synthetic Procedures

Retro-2 compound was either purchased from Chembridge, or were synthesized in house. Stock solutions were generated by dissolving Retro-2 in DMSO. When added to cells, the final concentration of DMSO used in these studies was 0.04% (v/v). Additional compounds were synthesized following general synthetic methods described herein. All commercially available reagents were used without further purification. Reactions were carried out in oven dried glassware, with dry solvent, and under ambient atmosphere. All spectra were referenced to residual solvent signals in $DMSO_{d6}$ (2.50 ppm for $^1H$, 39.51 ppm for $^{13}C$).

Dihydroquinazolinone Synthesis; General Procedure 1

Dicyclohecylcarbodiimide (5.00 mmol) and a nitrobenzoic acid (5.55 mmol) were dissolved in DCM (20 mL) and allowed to stir for 5 minutes before the addition of a primary amine (5.55 mmol) and dimethylaminopyridine (0.055 mmol). The coupling reaction was allowed to proceed for 16 hours, after which the DCM was evaporated. The solid residue was resuspended in ethyl acetate and filtered through a silica gel plug to remove the dicyclohexylurea byproduct. The filtrate was then concentrated and the desired nitrobenzamide isolated by silica gel chromatography using a hexanes/ethyl acetate solvent gradient.

The nitrobenzamide intermediate (0.5 mmol), an aldehyde (0.55 mmol) and scandium (III) triflate (0.05) mmol were combined in methanol (1 mL) in a sealed microwave vial. The reaction was microwave irradiated at 100° C. for 1 hour, after which the solvent was removed. The product dihydroquinazolinones were isolated by silica gel chromatography with a hexanes/ethyl acetate solvent gradient. The chromatographed products were subsequently purified by recrystallization.

Dihydroquinazolinone Synthesis; General Procedure 2

An isatoic anhydride (1.20 mmol) was added to THF (6 mL) and heated to 60° C. To the hot solution of isatoic anhydride was added a primary amine or ammonia (1.00 mmol), which was allowed to react for 1-2 hours. Once the amine had been completely consumed, an aldehyde (1.20 mmol) and scandium triflate (0.1 mmol) were added and allowed to react at 60° C. for an additional 3-5 hours, after which the solvent was removed. The product dihydroquinazolinones were isolated by silica gel chromatography with a hexanes/ethyl acetate solvent gradient. The chromatographed products were subsequently purified by recrystallization.

Synthesis of Retro-2 and Retro-2$^{cycl}$

To a stirring solution of 2-aminobenzanilide was added 5-methyl-2-thiophenecarboxaldehyde (86.3 μL, 0.80 mmol). After 24 hours, the reaction was concentrated and then chromatographed on silica gel with 20-40% ethyl acetate in hexanes. Retro-2 and Retro-2$^{cycl}$ were cleanly separated and then further purified by recrystallization from ethanol and ethyl acetate respectively. Yields: Retro-2 47.2 mg (36%), Retro-2$^{cycl}$ 78.0 mg (59.4%). Characterization: Retro-2 FAB HRMS: C$_{19}$H$_{16}$N$_2$OSNa$^+$ Predicted: 343.0881 Found: 343.0870. Retro-2$^{cycl}$ FAB HRMS: C$_{19}$H$_{16}$N$_2$OSNa$^+$ Predicted: 343.0881 Found: 343.0888.

Synthesis of Retro-2$^{Red}$

Retro-2$^{cycl}$ (143 mg, 0.444 mmol) was dissolved in methanol (4 mL) then treated with sodium cyanoborohydride (83 mg, 1.3 mmol) followed by acetic acid (0.4 mL). The slow formation of a new product was observed by tlc (2:1 hexanes:ethyl acetate). After 3 days the reaction was concentrated and then chromatographed on silica gel with a hexanes/ethyl acetate solvent gradient. Both the desired product (62 mg, 0.187 mmol, 42%) as well as unreacted starting material (64 mg, 0.200 mmol, 45%) were recovered. FAB HRMS: C$_{19}$H$_{18}$N$_2$OSNa$^+$ Predicted: 345.1038 Found: 345.1052.

Synthesis of Retro-2$^{meta}$

Dicyclohecylcarbodiimide (1.03 g, 5.00 mmol) and 3-nitrobenzoic acid (0.987 g, 5.55 mmol) were dissolved in DCM (20 mL) and allowed to stir for 5 minutes before the addition of aniline (0.500 mL, 5.55 mmol) and dimethylaminopyridine (0.068 g, 0.055 mmol). The coupling reaction was allowed to proceed for 16 hours at which point the DCM was evaporated. The solid residue was resuspended in ethyl acetate and filtered through a silica gel plug to remove the dicyclohexylurea byproduct. The filtrate was then concentrated and the desired nitrobenzamide isolated by silica gel chromatography using a hexanes/ethyl acetate solvent gradient. Yield: 1.118 g, 92%. FAB HRMS: C$_{13}$H$_{10}$N$_2$O$_3$Na$^+$ Predicted: 265.0589 Found: 265.0595. 1H NMR (600 MHz, DMSO-d6) δ=10.57 (s, 1H), 8.79 (t, J=1.8 Hz, 1H), 8.44 (ddd, J=0.9, 2.3, 8.2 Hz, 1H), 8.41 (td, J=1.3, 7.7 Hz, 1H), 7.84 (t, J=8.1 Hz, 1H), 7.79 (d, J=7.7 Hz, 2H), 7.39 (d, J=7.7 Hz, 1H), 7.38 (d, J=7.7 Hz, 1H), 7.14 (tt, J=1.1, 7.3 Hz, 1H) 13C NMR (151 MHz, DMSO-d6) δ=163.3, 147.7, 138.6, 136.3, 134.1, 130.1, 128.6, 126.1, 124.1, 122.4, 120.6.

The Nitrobenzamide (0.242 g, 1.00 mmol) was dissolved in methanol (3 mL) then treated with 10% Palladium on carbon (72.3 mg) and ammonium formate (350 mg, 5.5 mmol). The reaction was allowed to proceed for 45 minutes before being filtered through celite to remove the palladium on carbon. The filtrate was treated with 5-methyl-2-thiophenecarboxaldehyde (0.128 mL, 1.2 mmol) and scandium (III) triflate (0.076 g, 0.154 mmol) and then heated to reflux for 2 hours. Upon cooling to room temperature, the product precipitated from solution and was isolated by filtration. yield: 0.190 g, 59%. FAB HRMS: C$_{19}$H$_{16}$N$_2$OSNa$^+$ Predicted: 343.0881 Found: 343.0888.

TABLE 1

| Structure | Name | Characterization data |
|---|---|---|
| 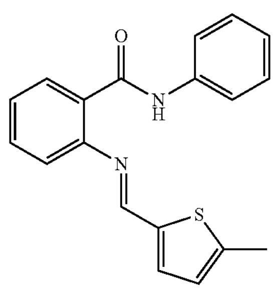 [SMILES: Cc1ccc(/C=N/c2ccccc2C(=O)Nc2ccccc2)s1] | Retro-2 | FAB HRMS: C$_{19}$H$_{16}$N$_2$OSNa$^+$ Predicted: 343.0881 Found: 343.0870. $^1$H NMR (600 MHz, DMSO-d$_6$) δ = 11.00 (s, 1 H), 8.79 (s, 1 H), 8.00 (dd, J = 1.5, 7.7 Hz, 1 H), 7.76 (d, J = 7.7 Hz, 2 H), 7.65 (d, J = 3.7 Hz, 1 H), 7.59 (dt, J = 1.5, 7.7 Hz, 1 H), 7.42-7.32 (m, 4 H), 7.10 (s, 1 H), 7.01 (dd, J = 1.1, 3.7 Hz, 1 H), 2.55 (s, 3 H). $^{13}$C NMR (151 MHz, DMSO-d$_6$) δ = 164.1, 155.7, 148.4, 147.4, 139.3, 138.6, 136.2, 132.3, 129.9, 128.8, 128.0, 127.5, 126.2, 123.6, 119.8, 119.4, 15.7 |
| 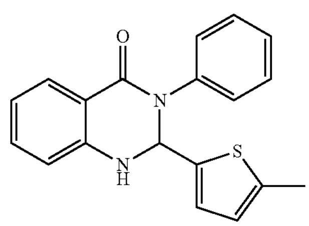 | RETRO-2cycl | Retro-2$^{cycl}$ FAB HRMS: C$_{19}$H$_{16}$N$_2$OSNa$^+$ Predicted: 343.0881 Found: 343.0888 $^1$H NMR (400 MHz, DMSO-d$_6$) δ = 7.73 (d, J = 8.0 Hz, 1 H), 7.61 (d, J = 2.8 Hz, 1 H), 7.41-7.34 (m, 2 H), 7.34-7.28 (m, 3 H), 7.27-7.20 (m, 1 H), 6.82 (d, J = 8.3 Hz, 1 H), 6.77 (t, J = 7.5 Hz, 1 H), 6.72 (d, J = 3.5 Hz, 1 H), 6.55 (d, J = 3.5 Hz, 1 H), 6.40 (d, J = 3.0 Hz, 1 H), 2.31 (s, 3 H). $^{13}$C NMR (151 MHz, DMSO-d$_6$) δ = 161.5, 146.3, 142.0, 140.5, 139.2, 133.7, 128.7, 127.9, 126.4, 126.3, 126.2, 124.4, 117.9, 115.5, 115.2, 69.6, 14.9 |
| 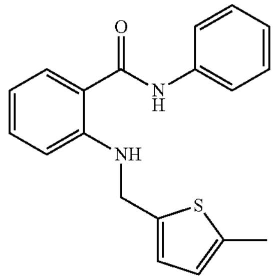 [SMILES: Cc1ccc(CNc2ccccc2C(=O)Nc2ccccc2)s1] | BU62382A-red Retro-2red | FAB HRMS: C$_{19}$H$_{18}$N$_2$OSNa$^+$ Predicted: 345.1038 Found: 345.1052 $^1$H NMR (600 MHz, DMSO-d$_6$) δ = 10.11 (s, 1 H), 7.78 (t, J = 5.7 Hz, 1 H), 7.76-7.65 (m, 3 H), 7.45-7.28 (m, 3 H), 7.16-7.06 (m, 1 H), 6.85 (d, J = 2.9 Hz, 1 H), 6.81 (d, J = 8.4 Hz, 1 H), 6.68 (t, J = 7.5 Hz, 1 H), 6.66-6.61 (m, 1 H), 2.38 (s, 3 H). $^{13}$C NMR (151 MHz, DMSO-d$_6$) δ = 168.0, 148.5, 140.5, 139.0, 138.1, 132.6, 129.0, 128.5, 125.0, 124.9, 123.5, 120.6, 116.1, 114.9, 111.6, 41.6, 14.9. |

TABLE 1-continued

| Structure | Name | Characterization data |
|---|---|---|
| 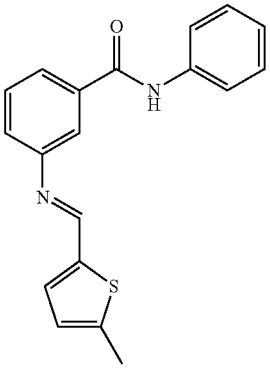 [SMILES: Cc1ccc(/C=N/c2cccc(C(=O)Nc3ccccc3)c2)s1] | BU62382A-meta Retro-2meta | FAB HRMS: $C_{19}H_{16}N_2OSNa^+$ Predicted: 343.0881 Found: 343.0888. $^1$H NMR (600 MHz, DMSO-$d_6$) δ = 10.28 (s, 1 H), 8.78 (s, 1 H), 7.82 (t, J = 1.7 Hz, 1 H), 7.82-7.78 (m, 3 H), 7.56-7.52 (m, 2 H), 7.45 (ddd, J = 1.1, 2.0, 7.9 Hz, 1 H), 7.38-7.33 (m, 2 H), 7.11 (tt, J = 1.1, 7.3 Hz, 1 H), 6.97-6.94 (m, 1 H), 2.53 (d, J = 0.7 Hz, 3 H). $^{13}$C NMR (151 MHz, DMSO-$d_6$) δ = 165.1, 154.7, 150.9, 145.9, 140.1, 139.1, 135.9, 134.6, 129.3, 128.5, 126.9, 125.1, 124.0, 123.6, 120.4, 120.2, 15.6 |
| 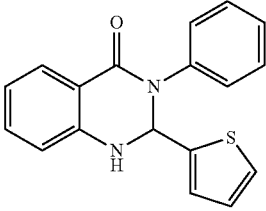 [SMILES: O=C1c2ccccc2NC(c2cccs2)N1c1ccccc1] | BU62382A1 RETRO2A1 | FAB HRMS: $C_{18}H_{14}N_2OSNa^+$ Predicted: 329.0725 Found: 329.0735. $^1$H NMR (400 MHz, DMSO-$d_6$) δ = 7.72 (dd, J = 1.8, 7.8 Hz, 1 H), 7.62 (d, J = 3.3 Hz, 1 H), 7.60-7.56 (m, 1 H), 7.42-7.35 (m, 2 H), 7.34-7.28 (m, 3 H), 7.28-7.23 (m, 1 H), 6.82 (dd, J = 0.8, 8.3 Hz, 1 H), 6.75 (s, 1 H), 6.33 (dd, J = 1.8, 3.3 Hz, 1 H), 6.24 (t, J = 3.3 Hz, 2 H). $^{13}$C NMR (151 MHz, DMSO-$d_6$) δ = 161.6, 146.3, 144.6, 140.5, 133.8, 128.7, 128.0, 126.5, 126.4, 126.4, 126.3, 125.9, 118.1, 115.6, 115.3, 69.5 |
| 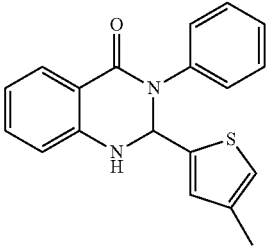 [SMILES: Cc1csc(C2Nc3ccccc3C(=O)N2c2ccccc2)c1] | BU62382A2 RETRO2A2 | FAB HRMS: $C_{19}H_{16}N_2OSNa^+$ Predicted: 343.0881 Found: 343.0872. $^1$H NMR (400 MHz, DMSO-$d_6$) δ = 7.73 (dd, J = 1.5, 7.8 Hz, 1 H), 7.62 (d, J = 2.8 Hz, 1 H), 7.42-7.29 (m, 5 H), 7.27-7.22 (m, 1 H), 6.94-6.90 (m, 1 H), 6.82 (d, J = 8.0 Hz, 1 H), 6.80-6.74 (m, 2 H), 6.44 (d, J = 2.8 Hz, 1 H), 2.07 (d, J = 0.8 Hz, 3 H). $^{13}$C NMR (101 MHz, DMSO-$d_6$) δ = 161.5, 146.3, 144.6, 140.5, 136.2, 133.8, 128.7, 128.3, 128.0, 126.3, 126.3, 120.9, 118.0, 115.6, 115.3, 69.4, 15.3. |
| 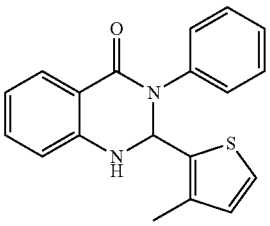 [SMILES: Cc1ccsc1C1Nc2ccccc2C(=O)N1c1ccccc1] | BU62382A3 RETRO2A3 | FAB HRMS: $C_{19}H_{16}N_2OSNa^+$ Predicted: 343.0881 Found: 343.0885. $^1$H NMR (400 MHz, DMSO-$d_6$) δ =7.74 (dd, J = 1.5, 7.8 Hz, 1 H), 7.48 (d, J = 2.0 Hz, 1 H), 7.37-7.29 (m, 3 H), 7.25-7.17 (m, 4 H), 6.83-6.75 (m, 2 H), 6.67 (d, J = 5.0 Hz, 1 H), 6.54 (d, J = 2.0 Hz, 1 H), 1.91 (s, 3 H). $^{13}$C NMR (75 MHz, DMSO-$d_6$) δ = 161.8, 146.6, 140.2, 137.0, 135.1, 133.8, 129.5, 128.6, 127.9, 127.5, 126.7, 124.2, 117.8, 115.0, 114.9, 67.9, 13.3. |
| 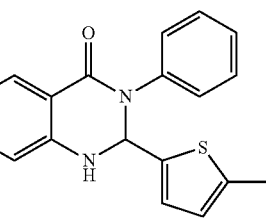 | BU62382A4 RETRO2A4 | FAB HRMS: $C_{20}H_{18}N_2OSNa^+$ Predicted: 357.1038 Found: 357.1028. $^1$H NMR (400 MHz, DMSO-$d_6$) δ = 7.74 (dd, J = 1.5, 7.8 Hz, 1 H), 7.63 (d, J = 2.8 Hz, 1 H), 7.41-7.34 (m, 2 H), 7.34-7.29 (m, 3 H), 7.27-7.21 (m, 1 H), 6.83 (d, J = 8.0 Hz, 1 H), 6.80-6.76 (m, 1 H), 6.75 (d, J = 3.5 Hz, 1 H), 6.58 (td, J = 1.1, 3.3 Hz, 1 H), 6.42 (d, J = 2.8 Hz, 1 H), 2.67 (q, J = 7.4 Hz, 2 H), 1.13 (t, J = 7.4 Hz, 3 H). $^{13}$C NMR (75 MHz, DMSO-$d_6$) δ = 161.5, 146.7, 146.3, 141.7, 140.5, 133.8, 128.7, 128.0, 126.4, 126.3, 126.1, 122.7, 118.0, 115.5, 115.2, 69.7, 22.7, 15.6 |

TABLE 1-continued

| Structure | Name | Characterization data |
|---|---|---|
| 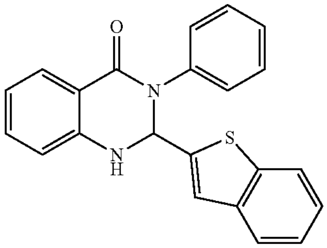 [SMILES: O=C1c2ccccc2NC(c2cc3ccccc3s2)N1c1ccccc1] | BU62382A5 RETRO2A5 | FAB HRMS: $C_{22}H_{16}N_2OSNa^+$ Predicted: 379.0881 Found: 379.0866. $^1$H NMR (400 MHz, DMSO-$d_6$) δ = 7.88-7.82 (m, 1 H), 7.79-7.71 (m, 3 H), 7.42-7.37 (m, 4 H), 7.37-7.33 (m, 1 H), 7.33-7.28 (m, 3 H), 7.28-7.22 (m, 1 H), 6.86 (d, J = 8.0 Hz, 1 H), 6.80 (dt, J = 1.0, 7.5 Hz, 1 H), 6.64 (d, J = 3.3 Hz, 1 H). $^{13}$C NMR (101 MHz, DMSO-$d_6$) δ = 161.4, 146.2, 145.3, 144.8, 140.4, 138.3, 134.0, 128.8, 128.0, 126.5, 124.9, 124.5, 123.8, 123.0, 122.6, 118.2, 115.6, 115.3, 107.6, 69.9. |
| 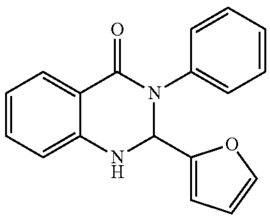 [SMILES: O=C1c2ccccc2NC(c2ccco2)N1c1ccccc1] | BU62382A6 RETRO2A6 | FAB HRMS: $C_{18}H_{14}N_2O_2Na^+$ Predicted: 313.0953 Found: 313.0945. $^1$H NMR (400 MHz, DMSO-$d_6$) δ = 7.72 (d, J = 7.3 Hz, 1 H), 7.62 (d, J = 3.0 Hz, 1 H), 7.58 (dd, J = 0.8, 1.9 Hz, 1 H), 7.43-7.35 (m, 2 H), 7.35-7.28 (m, 3 H), 7.28-7.23 (m, 1 H), 6.83 (d, J = 8.0 Hz, 1 H), 6.79-6.70 (m, J = 1.0, 7.5, 7.5 Hz, 1 H), 6.33 (dd, J = 1.9, 3.4 Hz, 1 H), 6.25 (t, J = 3.3 Hz, 2 H). $^{13}$C NMR (75 MHz, DMSO-$d_6$) δ = 161.8, 152.9, 146.5, 143.1, 140.6, 133.7, 128.7, 127.9, 126.3, 117.8, 115.5, 114.9, 110.4, 108.4, 67.3 |
| 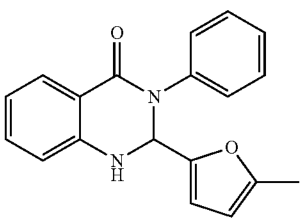 [SMILES: Cc1ccc(C2Nc3ccccc3C(=O)N2c2ccccc2)o1] | BU62382A7 RETRO2A7 | FAB HRMS: $C_{19}H_{16}N_2O_2Na^+$ Predicted: 327.1109 Found: 327.1125. $^1$H NMR (400 MHz, DMSO-$d_6$) δ = 7.72 (dd, J = 1.0, 7.8 Hz, 1 H), 7.62 (d, J = 3.0 Hz, 1 H), 7.42-7.33 (m, 4 H), 7.30 (ddd, J = 1.8, 7.0, 8.3 Hz, 1 H), 7.24 (tt, J = 1.8, 7.3 Hz, 1 H), 6.83 (d, J = 8.0 Hz, 1 H), 6.78-6.72 (m, 1 H), 6.17 (d, J = 3.3 Hz, 1 H), 6.11 (d, J = 3.0 Hz, 1 H), 5.93 (dd, J = 1.0, 3.0 Hz, 1 H), 2.16 (s, 3 H). $^{13}$C NMR (75 MHz, DMSO-$d_6$) δ = 161.8, 151.7, 150.8, 146.4, 140.6, 133.6, 128.7, 127.9, 126.3, 117.7, 115.5, 115.0, 109.4, 106.5, 67.3, 13.3. |
| 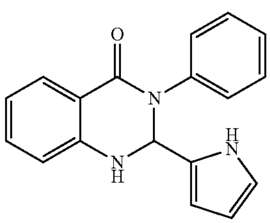 [SMILES: O=C1c2ccccc2NC(c2ccc[nH]2)N1c1ccccc1] | BU62382A8 RETRO2A8 | FAB HRMS: $C_{18}H_{15}N_3ONa^+$ Predicted: 312.1113 Found: 312.1118. $^1$H NMR (400 MHz, DMSO-$d_6$) δ = 10.72 (br. s., 1 H), 7.72 (dd, J = 1.5, 7.8 Hz, 1 H), 7.34-7.26 (m, 3 H), 7.26-7.21 (m, 3 H), 7.21-7.15 (m, 1 H), 6.79 (dd, J = 0.5, 8.3 Hz, 1 H), 6.75 (ddd, J = 1.0, 7.1, 7.5 Hz, 1 H), 6.63 (dt, J = 1.5, 2.6 Hz, 1 H), 6.18 (d, J = 2.3 Hz, 1 H), 5.89 (t, J = 3.5 Hz, 1 H), 5.81 (q, J = 2.7 Hz, 1 H). $^{13}$C NMR (75 MHz, DMSO-$d_6$) δ = 162.4, 146.8, 140.7, 133.4, 130.0, 128.5, 127.9, 126.6, 126.1, 118.2, 117.8, 115.9, 115.1, 107.6, 107.1, 68.1. |
| 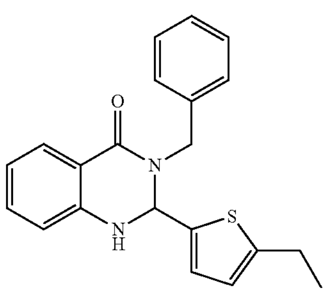 [SMILES: CCc1ccc(C2Nc3ccccc3C(=O)N2Cc2ccccc2)s1] | BU62382B1 RETRO2A4B1 | FAB HRMS: $C_{21}H_{20}N_2OSNa^+$ Predicted: 371.1194 Found: 371.1186. $^1$H NMR (600 MHz, DMSO-$d_6$) δ = 7.70 (dd, J = 1.8, 7.7 Hz, 1 H), 7.37 (d, J = 2.6 Hz, 1 H), 7.36-7.33 (m, 2 H), 7.32-7.30 (m, 2 H), 7.30-7.25 (m, 2 H), 6.87 (d, J = 3.7 Hz, 1 H), 6.74 (dt, J = 1.1, 7.5 Hz, 1 H), 6.71 (d, J = 8.1 Hz, 1 H), 6.65 (td, J = 1.1, 3.3 Hz, 1 H), 5.90 (d, J = 2.6 Hz, 1 H), 5.26 (d, J = 15.4 Hz, 1 H), 3.92 (d, J = 15.4 Hz, 1 H), 2.69 (dq, J = 1.1, 7.5 Hz, 2 H), 1.14 (t, J = 7.5 Hz, 3 H). $^{13}$C NMR (151 MHz, DMSO-$d_6$) δ = 161.7, 146.6, 146.1, 141.2, 137.5, 133.4, 128.4, 127.6, 127.4, 127.1, 126.0, 122.6, 117.7, 114.8, 114.7, 66.5, 46.7, 22.7, 15.6. |

TABLE 1-continued

| Structure | Name | Characterization data |
| --- | --- | --- |
| 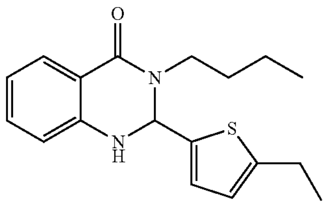 [SMILES: CCCCN1C(=O)c2ccccc2NC1c1ccc(CC)s1] | BU62382B2 RETRO2A4B2 | FAB HRMS: $C_{18}H_{22}N_2OSNa^+$ Predicted: 337.1351 Found: 337.1366. $^1$H NMR (600 MHz, DMSO-$d_6$) δ = 7.64 (dd, J = 1.5, 8.1 Hz, 1 H), 7.33 (d, J = 2.6 Hz, 1 H), 7.27-7.21 (m, 1 H), 6.88 (d, J = 3.7 Hz, 1 H), 6.73-6.67 (m, 2 H), 6.64 (td, J = 1.0, 3.6 Hz, 1 H), 6.00 (d, J = 2.6 Hz, 1 H), 3.86 (ddd, J = 6.6, 8.4, 13.6 Hz, 1 H), 2.83 (ddd, J = 5.5, 8.3, 13.7 Hz, 1 H), 2.68 (dq, 1.1, 7.5 Hz, 2 H), 1.59 1.51 (m, 1 H), 1.51-1.43 (m, 1 H), 1.34-1.21 (m, 2 H), 1.13 (t, J = 7.5 Hz, 3 H), 0.87 (t, J = 7.3 Hz, 3 H). $^{13}$C NMR (151 MHz, DMSO-$d_6$) δ = 161.5, 146.4, 146.0, 142.0, 133.1, 127.4, 125.7, 122.5, 117.5, 115.2, 114.6, 66.7, 43.7, 29.5, 22.6, 19.5, 15.6, 13.6. |
| 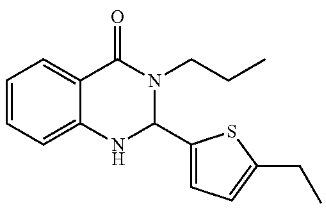 [SMILES: CCCN1C(=O)c2ccccc2NC1c1ccc(CC)s1] | BU62382B3 RETRO2A4B3 | FAB HRMS: $C_{17}H_{20}N_2OSNa^+$ Predicted: 323.1194 Found: 323.1188. $^1$H NMR (400 MHz, DMSO-$d_6$) δ = 7.68-7.61 (m, 1 H), 7.36 (br. s., 1 H), 7.24 (dt, J = 1.5, 7.7 Hz, 1 H), 6.88 (d, J = 3.5 Hz, 1 H), 6.74-6.67 (m, 2 H), 6.63 (d, J = 3.5 Hz, 1 H), 6.01 (d, J = 2.3 Hz, 1 H), 3.88-3.74 (m, 1 H), 2.81 (ddd, J = 5.7, 8.1, 13.5 Hz, 1 H), 2.67 (q, J = 7.6 Hz, 2 H), 1.67-1.55 (m, 1 H), 1.55-1.42 (m, 1 H), 1.13 (t, J = 7.6 Hz, 3 H), 0.85 (t, J = 7.5 Hz, 3 H). $^{13}$C NMR (101 MHz, DMSO-$d_6$) δ = 161.6, 146.4, 146.1, 142.1, 133.2, 127.4, 125.7, 122.6, 117.5, 115.2, 114.7, 66.8, 45.8, 22.7, 20.8, 15.7, 11.2. |
| 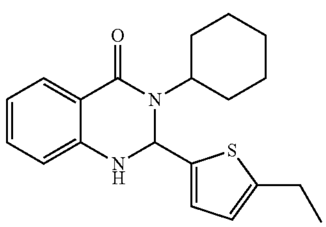 [SMILES: CCc1ccc(C2Nc3ccccc3C(=O)N2C2CCCCC2)s1] | BU62382B5 RETRO2A4B5 | FAB HRMS: $C_{20}H_{24}N_2OSNa^+$ Predicted: 363.1507 Found: 363.1522. $^1$H NMR (400 MHz, DMSO-$d_6$) δ = 7.65 (dd, J = 1.2, 7.7 Hz, 1 H), 7.28 (d, J = 2.4 Hz, 1 H), 7.21 (ddd, J = 1.5, 6.8, 8.6 Hz, 1 H), 6.85 (d, J = 3.7 Hz, 1 H), 6.70 (t, J = 7.5 Hz, 1 H), 6.66 (d, J = 8.1 Hz, 163 H), 6.58 (d, J = 3.4 Hz, 1 H), 6.08 (d, J = 2.9 Hz, 1 H), 4.23 (t, J = 11.9 Hz, 1 H), 2.64 (q, J = 7.4 Hz, 2 H), 1.76 (d, J = 10.8 Hz, 2 H), 1.68 (br. s., 1 H), 1.57 (br. s., 3 H), 1.39-1.15 (m, 4 H), 1.11 (t, J = 7.5 Hz, 3 H). $^{13}$C NMR (101 MHz, DMSO-$d_6$) δ = 161.2, 145.7, 145.7, 144.0, 133.0, 127.6, 125.2, 122.4, 117.6, 116.4, 114.9, 63.0, 53.4, 30.3, 30.3, 25.7, 25.6, 24.9, 22.6, 15.5. |
| 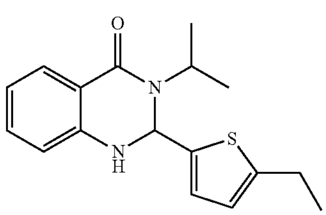 [SMILES: CCc1ccc(C2Nc3ccccc3C(=O)N2C(C)C)s1] | BU62382B6 RETRO2A4B6 | FAB HRMS: $C_{17}H_{20}N_2OSNa^+$ Predicted: 323.1194 Found: 323.1180. $^1$H NMR (600 MHz, DMSO-$d_6$) δ = 7.66 (dd, J = 1.1, 7.7 Hz, 1 H), 7.26 (d, J = 2.9 Hz, 1 H), 7.22 (ddd, J = 1.5, 7.3, 8.2 Hz, 1 H), 6.87 (d, J = 3.7 Hz, 1 H), 6.71 (t, J = 7.5 Hz, 1 H), 6.68 (d, J = 8.1 Hz, 1 H), 6.59 (d, J = 3.7 Hz, 1 H), 6.06 (d, J = 2.9 Hz, 1 H), 4.55 (spt, J = 6.8 Hz, 1 H), 2.64 (q, J = 7.5 Hz, 2 H), 1.23 (d, J = 7.0 Hz, 3 H), 1.11 (t, J = 7.5 Hz, 3 H), 1.04 (d, J = 7.0 Hz, 3 H). $^{13}$C NMR (151 MHz, DMSO-$d_6$) δ = 161.2, 145.8, 145.7, 143.8, 132.9, 127.5, 125.2, 122.3, 117.6, 116.3, 114.8, 63.0, 45.6, 22.6, 20.3, 20.1, 15.5. |

TABLE 1-continued

| Structure | Name | Characterization data |
|---|---|---|
| 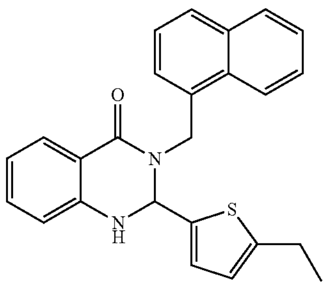 [SMILES: CCc1ccc(C2Nc3ccccc3C(=O)N2Cc2cccc3ccccc23)s1] | BU62382B8 RETRO2A4B8 | FAB HRMS: $C_{25}H_{22}N_2OSNa^+$ Predicted: 421.1351 Found: 421.1359. $^1$H NMR (400 MHz, DMSO-$d_6$) δ = 8.13-8.06 (m, 1 H), 8.00-7.94 (m, 1 H), 7.91 (d, J = 7.8 Hz, 1 H), 7.76 (d, J = 7.8 Hz, 1 H), 7.58-7.46 (m, 4 H), 7.34 (d, J = 2.3 Hz, 1 H), 7.32-7.26 (m, 1 H), 6.91 (d, J = 3.5 Hz, 1 H), 6.80-6.74 (m, 1 H), 6.68 (d, J = 8.3 Hz, 1 H), 6.67-6.64 (m, 1 H), 5.89 (d, J = 15.4 Hz, 1 H), 5.80 (d, J = 2.5 Hz, 1 H), 4.22 (d, J = 15.7 Hz, 1 H), 2.69 (q, J = 7.5 Hz, 2 H), 1.14 (dt, J = 1.3, 7.4 Hz, 3 H). $^{13}$C NMR (101 MHz, DMSO-$d_6$) δ = 161.6, 146.6, 146.0, 140.8, 133.7, 133.5, 132.2, 131.1, 128.6, 128.2, 127.8, 126.5, 126.2, 126.0, 125.5, 123.6, 122.7, 117.8, 114.9, 114.7, 65.8, 44.4, 22.7, 15.7. |
| 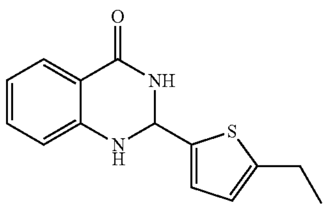 [SMILES: CCc1ccc(C2NC(=O)c3ccccc3N2)s1] | BU62382B10 RETRO2A4B10 | FAB HRMS: $C_{14}H_{14}N_2OSNa^+$ Predicted: 281.0725 Found: 287.0730. $^1$H NMR (400 MHz, DMSO-$d_6$) δ = 8.39 (br. s, 1 H), 7.60 (dd, J = 1.5, 7.8 Hz, 1 H), 7.28-7.22 (m, 1 H), 7.21 (br. s, 1 H), 6.91 (d, J = 3.3 Hz, 1 H), 6.74 (d, J = 8.1 Hz, 1 H), 6.72-6.66 (m, 2 H), 5.92 (t, J = 1.8 Hz, 1 H), 2.74 (dq, J = 0.8, 7.6 Hz, 2 H), 1.18 (t, J = 7.6 Hz, 3 H). $^{13}$C NMR (151 MHz, DMSO-$d_6$) δ = 163.0, 147.2, 146.7, 143.4, 133.3, 127.2, 125.3, 122.7, 117.4, 115.0, 114.6, 62.8, 22.8, 15.8. |
| 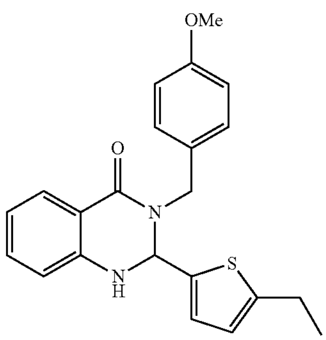 [SMILES: CCc1ccc(C2Nc3ccccc3C(=O)N2Cc2ccc(OC)cc2)s1] | BU62382B11 RETRO2A4B11 | FAB HRMS: $C_{22}H_{22}N_2O_2SNa^+$ Predicted: 401.1300 Found: 401.1285. $^1$H NMR (400 MHz, DMSO-$d_6$) δ = 7.69 (dd, J = 1.3, 7.6 Hz, 1 H), 7.34 (d, J = 2.8 Hz, 1 H), 7.32-7.19 (m, 3 H), 6.90 (d, J = 8.6 Hz, 2 H), 6.86 (d, J = 3.5 Hz, 1 H), 6.73 (t, J = 7.5 Hz, 1 H), 6.69 (d, J = 7.8 Hz, 1 H), 6.65 (d, J = 3.5 Hz, 1 H), 5.84 (d, J = 2.5 Hz, 1 H), 5.22 (d, J = 14.9 Hz, 1 H), 3.80 (d, J = 14.9 Hz, 1 H), 3.73 (s, 3 H), 2.68 (q, J = 7.5 Hz, 2 H), 1.14 (t, J = 7.6 Hz, 3 H). $^{13}$C NMR (101 MHz, DMSO-$d_6$) δ = 161.6, 158.6, 146.6, 146.1, 141.3, 133.5, 129.3, 129.1, 127.6, 126.0, 122.7, 117.7, 114.8, 114.7, 113.9, 66.2, 55.1, 46.0, 22.7, 15.7. |
| 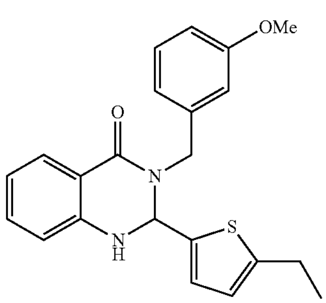 [SMILES: CCc1ccc(C2Nc3ccccc3C(=O)N2Cc2cccc(OC)c2)s1] | BU62382B12 RETRO2A4B12 | FAB HRMS: $C_{22}H_{22}N_2O_2SNa^+$ Predicted: 401.1300 Found: 401.1282. $^1$H NMR (400 MHz, DMSO-$d_6$) δ = 7.69 (dd, J = 1.4, 7.7 Hz, 1 H), 7.39 (d, J = 2.5 Hz, 1 H), 7.32-7.22 (m, 2 H), 6.92-6.82 (m, 4 H), 6.78-6.69 (m, 2 H), 6.64 (d, J = 3.3 Hz, 1 H), 5.90 (d, J = 2.8 Hz, 1 H), 5.23 (d, J = 15.4 Hz, 1 H), 3.90 (d, J = 15.4 Hz, 1 H), 3.72 (s, 3 H), 2.68 (q, J = 7.5 Hz, 2 H), 1.14 (t, J = 7.6 Hz, 3 H). $^{13}$C NMR (101 MHz, DMSO-$d_6$) δ = 165.2, 159.4, 146.6, 141.3, 139.1, 133.5, 129.6, 127.6, 126.0, 122.6, 119.6, 117.7, 114.8, 113.2, 112.4, 66.6, 55.0, 46.7, 22.7, 15.7. |
| 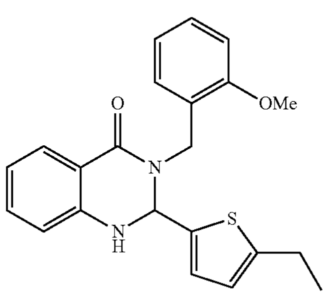 [SMILES: CCc1ccc(C2Nc3ccccc3C(=O)N2Cc2ccccc2OC)s1] | BU62382B13 RETRO2A4B13 | FAB HRMS: $C_{22}H_{22}N_2O_2SNa^+$ Predicted: 401.1300 Found: 401.1289. $^1$H NMR (400 MHz, DMSO-$d_6$) δ = 7.67 (dd, J = 1.4, 7.7 Hz, 1 H), 7.41 (d, J = 2.8 Hz, 1 H), 7.32-7.24 (m, 2 H), 7.22 (d, J = 7.3 Hz, 1 H), 7.02 (d, J = 7.8 Hz, 1 H), 6.93 (t, J = 7.5 Hz, 1 H), 6.85 (d, J = 3.5 Hz, 1 H), 6.77-6.69 (m, 2 H), 6.67-6.63 (m, 1 H), 5.92 (d, J = 2.3 Hz, 1 H), 5.11 (d, J = 15.9 Hz, 1 H), 3.96 (d, J = 15.9 Hz, 1 H), 3.81 (s, 3 H), 2.69 (q, J = 7.6 Hz, 2 H), 1.14 (t, J = 7.5 Hz, 3 H). $^{13}$C NMR (101 MHz, DMSO-$d_6$) δ = 157.0, 146.2, 141.5, 133.5, 128.4, 127.7, 127.6, 125.9, 122.7, 120.4, |

| Structure | Name | Characterization data |
|---|---|---|
| | | 117.7, 114.9, 114.8, 110.7, 66.8, 55.4, 42.1, 22.7, 15.7. |
| 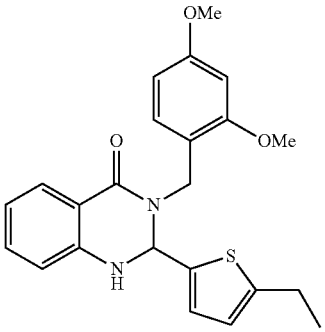 [SMILES: CCc1ccc(C2Nc3ccccc3C(=O)N2Cc2ccc(OC)cc2OC)s1] | BU62382B14 RETRO2A4B14 | FAB HRMS: $C_{23}H_{24}N_2O_3SNa^+$ Predicted: 431.1405 Found: 431.1405. $^1$H NMR (400 MHz, DMSO-$d_6$) δ = 7.69 (dd, J = 1.4, 7.7 Hz, 1 H), 7.36 (d, J = 2.8 Hz, 1 H), 7.30-7.23 (m, 1 H), 7.14 (d, J = 8.3 Hz, 1 H), 6.84 (d, J = 3.5 Hz, 1 H), 6.76-6.68 (m, 2 H), 6.65 (d, J = 3.5 Hz, 1 H), 6.59 (d, J = 2.5 Hz, 1 H), 6.52 (dd, J = 2.4, 8.5 Hz, 1 H), 5.87 (d, J = 2.5 Hz, 1 H), 5.08 (d, J = 15.4 Hz, 1 H), 3.89 (d, J = 15.4 Hz, 1 H), 3.79 (s, 3 H), 3.75 (s, 3 H), 2.69 (q, J = 7.5 Hz, 2 H), 1.14 (t, J = 7.6 Hz, 3 H). $^{13}$C NMR (101 MHz, DMSO-$d_6$) δ = 161.6, 160.0, 158.1, 146.5, 146.0, 141.6, 133.4, 129.2, 127.6, 125.7, 122.7, 117.6, 117.0, 115.0, 114.7, 104.7, 98.4, 66.5, 55.5, 55.2, 41.5, 22.7, 15.7. |
| 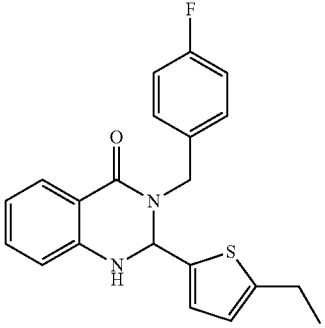 [SMILES: CCc1ccc(C2Nc3ccccc3C(=O)N2Cc2ccc(F)cc2)s1] | BU62382B15 RETRO2A4B15 | FAB HRMS: $C_{21}H_{19}FN_2OSNa^+$ Predicted: 389.1100 Found: 389.1109. $^1$H NMR (400 MHz, DMSO-$d_6$) δ = 7.69 (dd, J = 1.6, 7.7 Hz, 1 H), 7.40 (d, J = 2.8 Hz, 1 H), 7.38-7.32 (m, 2 H), 7.31-7.25 (m, 1 H), 7.19-7.12 (m, 2 H), 6.87 (d, J = 3.5 Hz, 1 H), 6.79-6.69 (m, 2 H), 6.64 (td, J = 1.0, 3.5 Hz, 1 H), 5.94 (d, J = 2.5 Hz, 1 H), 5.16 (d, J = 15.4 Hz, 1 H), 3.98 (d, J = 15.4 Hz, 1 H), 2.68 (dq, J = 0.9, 7.5 Hz, 2 H), 1.13 (t, J = 7.5 Hz, 3 H). $^{13}$C NMR (101 MHz, DMSO-d6) δ = 161.8, 146.7, 146.2, 141.3, 133.8, 133.8, 133.5, 129.6, 129.5, 127.6, 127.4, 126.1, 122.6, 117.7, 115.3, 115.1, 114.8, 114.8, 66.7, 46.3, 22.7, 15.7. |
| 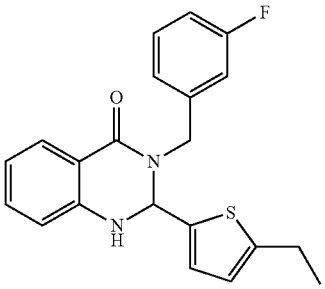 [SMILES: CCc1ccc(C2Nc3ccccc3C(=O)N2Cc2cccc(F)c2)s1] | BU62382B16 RETRO2A4B16 | FAB HRMS: $C_{21}H_{19}FN_2OSNa^+$ Predicted: 389.1100 Found: 389.1082. $^1$H NMR (400 MHz, Acetone) δ = 7.70 (dd, J = 1.1, 8.0 Hz, 1 H), 7.44 (d, J = 2.5 Hz, 1 H), 7.41-7.33 (m, 1 H), 7.29 (dt, J = 1.6, 7.6 Hz, 1 H), 7.16 (d, J = 7.6 Hz, 1 H), 7.14-7.05 (m, 2 H), 6.88 (d, J = 3.3 Hz, 1 H), 6.78-6.71 (m, 2 H), 6.67-6.62 (m, 1 H), 6.00 (d, J = 2.5 Hz, 1 H), 5.16 (d, J = 15.7 Hz, 1 H), 4.06 (d, J = 15.7 Hz, 1 H), 2.68 (q, J = 7.5 Hz, 2 H), 1.13 (t, J = 7.5 Hz, 3 H). $^{13}$C NMR (101 MHz, Acetone) δ = 163.5, 161.9, 161.0, 146.7, 146.3, 141.2, 140.8, 140.7, 133.6, 130.4, 130.3, 127.6, 126.2, 123.4, 123.4, 122.6, 117.8, 114.9, 114.7, 114.2, 114.0, 113.7, 67.0, 46.7, 22.7, 15.7. |
| 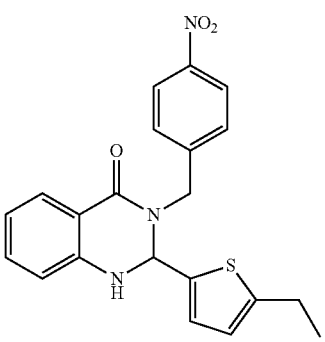 [SMILES: CCc1ccc(C2Nc3ccccc3C(=O)N2Cc2ccc([N+](=O)[O-])cc2)s1] | BU62382B17 RETRO2A4B17 | FAB HRMS: $C_{21}H_{19}N_3O_3SNa^+$ Predicted: 416.1045 Found: 416.1061. $^1$H NMR (400 MHz, DMSO-$d_6$) δ = 8.27-8.12 (m, 2 H), 7.69 (dd, J = 1.5, 8.1 Hz, 1 H), 7.55 (d, J = 8.8 Hz, 2 H), 7.49 (d, J = 2.3 Hz, 1 H), 7.36-7.25 (m, 1 H), 6.89 (d, J = 3.5 Hz, 1 H), 6.82-6.71 (m, 2 H), 6.63 (td, J = 0.9, 3.5 Hz, 1 H), 6.07 (d, J = 2.5 Hz, 1 H), 5.15 (d, J = 16.2 Hz, 1 H), 4.29 (d, J = 16.2 Hz, 1 H), 2.67 (q, J = 7.4 Hz, 2 H), 1.12 (t, J = 7.5 Hz, 3 H). $^{13}$C NMR (101 MHz, DMSO-$d_6$) δ = 162.1, 146.9, 146.6, 146.4, 146.0, 141.1, 133.7, 128.4, 127.6, 126.4, 123.5, 122.6, 117.8, 114.9, 114.6, 67.4, 47.0, 22.7, 15.8. |

TABLE 1-continued

| Structure | Name | Characterization data |
|---|---|---|
| 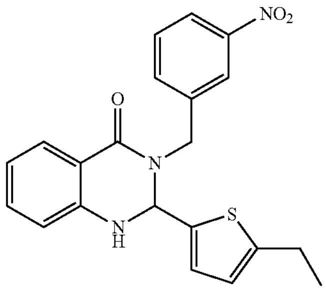 [SMILES: CCc1ccc(C2Nc3ccccc3C(=O)N2Cc2cccc([N+](=O)[O-])c2)s1] | BU62382B18 RETRO2A4B18 | FAB HRMS: $C_{21}H_{19}N_3O_3SNa^+$ Predicted: 416.1045 Found: 416.1038. $^1$H NMR (400 MHz, DMSO-$d_6$) δ = 8.17-8.04 (m, 2 H), 7.76 (d, J = 7.8 Hz, 1 H), 7.74-7.67 (m, 1 H), 7.67-7.56 (m, 1 H), 7.48 (d, J = 2.3 Hz, 1 H), 7.30 (dt, J = 1.6, 7.6 Hz, 1 H), 6.88 (d, J = 3.5 Hz, 1 H), 6.83-6.71 (m, 2 H), 6.66-6.58 (m, 1 H), 6.13 (d, J = 2.5 Hz, 1 H), 5.07 (d, J = 15.4 Hz, 1 H), 4.39 (d, J = 15.7 Hz, 1 H), 2.65 (q, J = 7.5 Hz, 2 H), 1.10 (t, J = 7.6 Hz, 3 H). $^{13}$C NMR (101 MHz, DMSO-$d_6$) δ = 162.2, 147.7, 146.8, 146.4, 141.3, 140.4, 134.3, 133.7, 129.9, 127.6, 126.4, 122.6, 122.1, 117.8, 114.9, 114.6, 67.4, 46.9, 22.7, 15.7. |
| 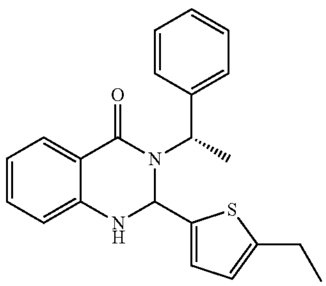 [SMILES: CCc1ccc(C2Nc3ccccc3C(=O)N2[C@@H](C)c2ccccc2)s1] | BU62382B19 RETRO2A4B19 | FAB HRMS: $C_{22}H_{22}N_2OSNa^+$ Predicted: 385.1351 Found: 385.1342. $^1$H NMR (400 MHz, DMSO-$d_6$) δ = 7.71 (d, J = 7.8 Hz, 1 H), 7.43-7.35 (m, 4 H), 7.34-7.28 (m, 1 H), 7.28-7.20 (m, 2 H), 6.81 (d, J = 3.3 Hz, 1 H), 6.74 (t, J = 7.5 Hz, 1 H), 6.65 (d, J = 8.1 Hz, 1 H), 6.61 (d, J = 3.3 Hz, 1 H), 5.90 (q, J = 7.1 Hz, 1 H), 5.78 (d, J = 3.0 Hz, 1 H), 2.66 (q, J = 7.7 Hz, 2 H), 1.36 (d, J = 7.3 Hz, 3 H), 1.12 (t, J = 7.6 Hz, 3 H). $^{13}$C NMR (101 MHz, CHLOROFORM-d) δ = 161.6, 146.0, 145.8, 143.6, 141.5, 133.3, 128.5, 127.8, 127.3, 126.8, 125.3, 122.5, 117.8, 115.9, 115.0, 63.0, 51.0, 22.6, 17.5, 15.6. |
| 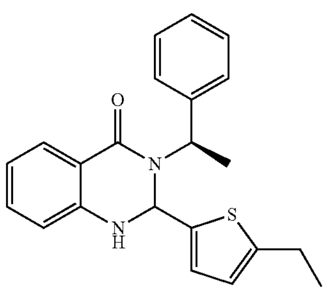 [SMILES: CCc1ccc(C2Nc3ccccc3C(=O)N2[C@H](C)c2ccccc2)s1] | BU62382B20 RETRO2A4B20 | FAB HRMS: $C_{22}H_{22}N_2OSNa^+$ Predicted: 385.1351 Found: 385.1335. $^1$H NMR (400 MHz, DMSO-$d_6$) δ = 7.71 (dd, J = 1.5, 7.8 Hz, 1 H), 7.42-7.35 (m, 4 H), 7.34-7.28 (m, 1 H), 7.28-7.22 (m, 2 H), 6.81 (d, J = 3.5 Hz, 1 H), 6.78-6.70 (m, 1 H), 6.65 (d, J = 8.1 Hz, 1 H), 6.61 (d, J = 3.5 Hz, 1 H), 5.90 (q, J = 7.2 Hz, 1 H), 5.78 (d, J = 3.0 Hz, 1 H), 2.66 (q, J = 7.5 Hz, 2 H), 1.36 (d, J = 7.3 Hz, 3 H), 1.12 (t, J = 7.6 Hz, 3 H). $^{13}$C NMR (101 MHz, DMSO-$d_6$) δ = 161.5, 146.0, 145.8, 143.6, 141.5, 133.3, 128.5, 127.8, 127.2, 126.8, 125.3, 122.5, 117.8, 115.9, 115.0, 63.0, 51.0, 22.6, 17.5, 15.6 |
| 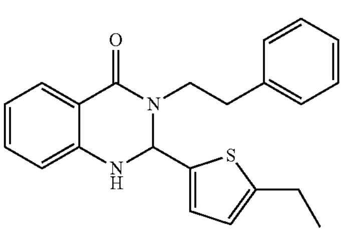 [SMILES: CCc1ccc(C2Nc3ccccc3C(=O)N2CCc2ccccc2)s1] | BU62382B21 RETRO2A4B21 | FAB HRMS: $C_{22}H_{22}N_2OSNa^+$ Predicted: 385.1351 Found: 385.1369. $^1$H NMR (400 MHz, DMSO-$d_6$) δ = 7.65 (d, J = 7.8 Hz, 1 H), 7.37 (s, 1 H), 7.33-7.25 (m, 3 H), 7.25-7.17 (m, 3 H), 6.92 (d, J = 3.5 Hz, 1 H), 6.77-6.68 (m, 2 H), 6.68-6.62 (m, 1 H), 6.04 (d, J = 2.3 Hz, 1 H), 4.09-3.93 (m, 1 H), 3.14-3.01 (m, 1 H), 2.98-2.84 (m, 1 H), 2.81-2.71 (m, J = 5.1, 9.0, 9.0 Hz, 1 H), 2.68 (q, J = 7.3 Hz, 2 H), 1.13 (t, J = 7.6 Hz, 3 H). $^{13}$C NMR (101 MHz, DMSO-$d_6$) δ = 161.7, 146.7, 146.2, 141.8, 139.1, 133.3, 128.6, 128.4, 127.4, 126.2, 125.9, 122.6, 117.5, 114.9, 114.6, 67.0, 45.9, 33.6, 22.7, 15.7. |

TABLE 1-continued

| Structure | Name | Characterization data |
|---|---|---|
| 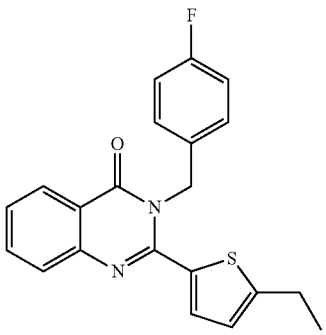 [SMILES: CCc1ccc(-c2nc3ccccc3c(=O)n2Cc2ccc(F)cc2)s1] | BU62382B15ox Retro2A4B15ox | FAB HRMS: $C_{21}H_{17}FN_2OSNa^+$ Predicted: 387.0943 Found: 387.0938. $^1$H NMR (400 MHz, DMSO-$d_6$) δ = 8.14 (dd, J = 1.3, 8.3 Hz, 1 H), 7.85 (dt, J = 1.4, 7.6 Hz, 1 H), 7.67 (d, J = 7.8 Hz, 1 H), 7.59-7.50 (m, 1 H), 7.19-7.07 (m, 5 H), 6.83 (dd, J = 0.8, 3.8 Hz, 1 H), 5.45 (s, 2 H), 2.81 (q, J = 7.5 Hz, 2 H), 1.23 (t, J = 7.5 Hz, 3 H). $^{13}$C NMR (101 MHz, DMSO-$d_6$) δ = 162.5, 161.8, 160.1, 152.0, 150.0, 147.0, 135.0, 134.0, 133.1, 133.1, 129.6, 128.1, 128.0, 127.2, 126.6, 124.7, 119.7, 115.8, 115.5, 48.2, 22.8, 15.8. |
| 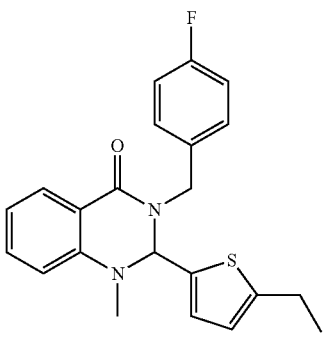 [SMILES: CCc1ccc(C2N(Cc3ccc(F)cc3)C(=O)c3ccccc3N2C)s1] | BU62382C1 Retro2A4B15C1 | $C_{22}H_{21}FN_2OSNa^+$ Predicted: 403.1256 Found: 403.1266. $^1$H NMR (400 MHz, DMSO-$d_6$) δ = 7.80 (dd, J = 1.5, 7.6 Hz, 1 H), 7.46-7.40 (m, 1 H), 7.40-7.33 (m, 2 H), 7.21-7.12 (m, 2 H), 6.93 (d, J = 3.5 Hz, 1 H), 6.88 (dt, J = 1.0, 7.5 Hz, 1 H), 6.69 (d, J = 8.1 Hz, 1 H), 6.65 (td, J = 1.0, 3.5 Hz, 1 H), 5.92 (s, 1 H), 5.13 (d, J = 15.4 Hz, 1 H), 3.95 (d, J = 15.4 Hz, 1 H), 2.77 (s, 3 H), 2.68-2.60 (m, 2 H), 1.11 (t, J = 7.5 Hz, 3 H). $^{13}$C NMR (101 MHz, DMSO-$d_6$) δ = 161.3, 147.0, 146.4, 134.1, 133.5, 133.5, 129.6, 129.5, 127.8, 127.7, 122.6, 118.3, 115.3, 115.1, 112.9, 73.3, 46.3, 34.9, 22.6, 15.5. |
| 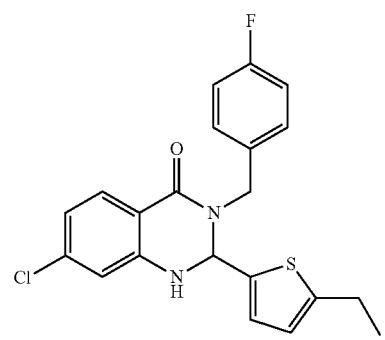 [SMILES: CCc1ccc(C2Nc3cc(Cl)ccc3C(=O)N2Cc2ccc(F)cc2)s1] | BU62382C2 Retro2A4B15C2 | $C_{21}H_{18}FN_2OSNa^+$ Predicted: 423.0710 Found: 423.0718. $^1$H NMR (400 MHz, DMSO-$d_6$) δ = 7.71-7.65 (m, 2 H), 7.33 (dd, J = 5.7, 8.5 Hz, 2 H), 7.15 (t, J = 8.8 Hz, 2 H), 6.89 (d, J = 3.5 Hz, 1 H), 6.79-6.73 (m, 2 H), 6.68-6.63 (m, 1 H), 6.02 (d, J = 2.5 Hz, 1 H), 5.12 (d, J = 15.4 Hz, 1 H), 3.99 (d, J = 15.4 Hz, 1 H), 2.69 (q, J = 7.5 Hz, 2 H), 1.14 (t, J = 7.5 Hz, 3 H). $^{13}$C NMR (101 MHz, DMSO-$d_6$) δ = 161.1, 160.2, 147.2, 147.0, 140.9, 138.1, 133.6, 133.6, 129.7, 129.6, 129.5, 126.4, 122.8, 117.8, 115.3, 115.1, 113.9, 113.4, 66.7, 46.3, 22.7, 15.7. |
| 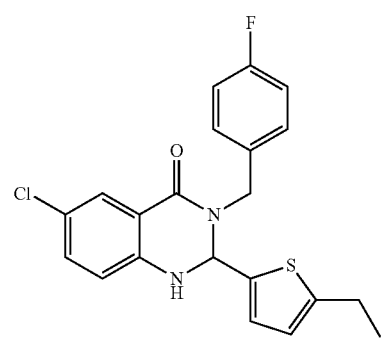 [SMILES: CCc1ccc(C2Nc3ccc(Cl)cc3C(=O)N2Cc2ccc(F)cc2)s1] | BU62382C3 Retro2A4B15C3 | $C_{21}H_{18}FN_2OSNa^+$ Predicted: 423.0710 Found: 423.0725. $^1$H NMR (400 MHz, DMSO-$d_6$) δ = 7.63 (dd, J = 2.5, 5.3 Hz, 2 H), 7.42-7.29 (m, 3 H), 7.20-7.12 (m, 2 H), 6.88 (d, J = 3.3 Hz, 1 H), 6.76 (d, J = 8.8 Hz, 1 H), 6.67-6.63 (m, 1 H), 6.01 (d, J = 2.5 Hz, 1 H), 5.13 (d, J = 15.2 Hz, 1 H), 4.01 (d, J = 15.2 Hz, 1 H), 2.68 (q, J = 7.4 Hz, 2 H), 1.14 (t, J = 7.6 Hz, 3 H). $^{13}$C NMR (101 MHz, DMSO-$d_6$) δ = 160.7, 146.9, 145.0, 140.9, 133.4, 129.6, 129.6, 126.6, 126.3, 122.7, 121.6, 116.9, 115.8, 115.3, 115.1, 66.6, 46.4, 22.7, 15.7. |

TABLE 1-continued

| Structure | Name | Characterization data |
|---|---|---|
| 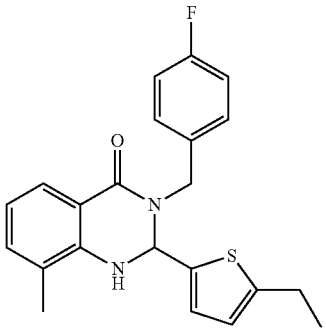 [SMILES: CCc1ccc(C2Nc3c(C)cccc3C(=O)N2Cc2ccc(F)cc2)s1] | BU62382C5<br>Retro2A4B15C5 | $C_{22}H_{21}FN_2OSNa^+$ Predicted: 403.1256<br>Found: 403.1265. $^1$H NMR (400 MHz, DMSO-d$_6$) δ = 7.57 (d, J = 8.1 Hz, 1 H), 7.45-7.32 (m, 2 H), 7.18 (t, J = 7.8 Hz, 3 H), 6.97 (d, J = 3.5 Hz, 1 H), 6.81 (d, J = 3.3 Hz, 1 H), 6.71-6.65 (m, 1 H), 6.62 (d, J = 3.3 Hz, 1 H), 5.90 (d, J = 3.8 Hz, 1 H), 5.27 (d, J = 15.9 Hz, 1 H), 4.04 (d, J = 14.9 Hz, 1 H), 2.67 (q, J = 7.6 Hz, 2 H), 2.07 (s, 3 H), 1.13 (t, J = 7.6 Hz, 3 H). $^{13}$C NMR (101 MHz, DMSO-d$_6$) δ = 162.1, 146.4, 142.0, 134.1, 129.7, 129.6, 125.5, 125.5, 122.9, 122.8, 117.6, 115.4, 115.2, 66.1, 46.5, 22.7, 16.8, 15.7. |
| 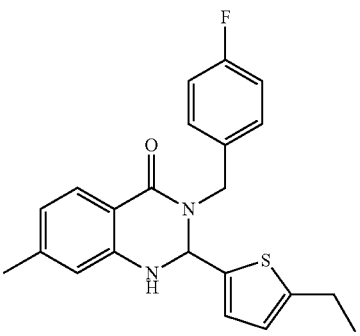 [SMILES: CCc1ccc(C2Nc3cc(C)ccc3C(=O)N2Cc2ccc(F)cc2)s1] | BU62382C6<br>Retro2A4B15C6 | $C_{22}H_{21}FN_2OSNa^+$ Predicted: 403.1256<br>Found: 403.1241. $^1$H NMR (400 MHz, DMSO-d$_6$) δ = 7.57 (d, J = 7.8 Hz, 1 H), 7.37-7.29 (m, 3 H), 7.19-7.11 (m, 2 H), 6.85 (d, J = 3.5 Hz, 1 H), 6.63 (td, J = 0.9, 3.4 Hz, 1 H), 6.56 (dd, J = 1.0, 8.1 Hz, 1 H), 6.51 (s, 1 H), 5.90 (d, J = 2.5 Hz, 1 H), 5.15 (d, J = 15.2 Hz, 1 H), 3.95 (d, J = 15.4 Hz, 1 H), 2.68 (q, J = 7.6 Hz, 2 H), 1.16-1.11 (m, 3 H). $^{13}$C NMR (101 MHz, DMSO-d$_6$) δ = 162.1, 146.4, 143.9, 142.0, 134.1, 134.0, 133.9, 129.6, 129.6, 125.5, 125.5, 122.9, 122.7, 117.5, 115.4, 115.2, 115.2, 66.1, 46.5, 22.7, 16.8, 15.6. |
| 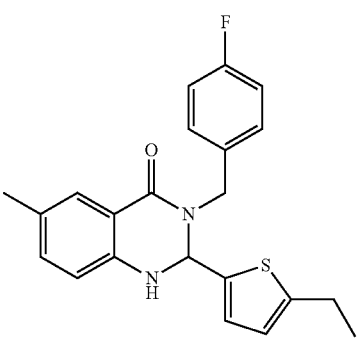 [SMILES: CCc1ccc(C2Nc3ccc(C)cc3C(=O)N2Cc2ccc(F)cc2)s1] | BU62382C7<br>Retro2A4B15C7 | $C_{22}H_{21}FN_2OSNa^+$ Predicted: 403.1256<br>Found: 403.1250. $^1$H NMR (400 MHz, Acetone) δ = 7.50 (s, 1 H), 7.34 (dd, J = 5.6, 8.1 Hz, 2 H), 7.23-7.07 (m, 4 H), 6.85 (d, J = 3.5 Hz, 1 H), 6.71-6.54 (m, 2 H), 5.90 (d, J = 2.3 Hz, 1 H), 5.16 (d, J = 15.4 Hz, 1 H), 3.97 (d, J = 15.4 Hz, 1 H), 2.67 (q, J = 7.4 Hz, 2 H), 2.21 (s, 3 H), 1.13 (t, J = 7.3 Hz, 3 H). $^{13}$C NMR (101 MHz, DMSO-d$_6$) δ = 161.9, 146.6, 144.0, 141.4, 134.4, 129.6, 129.5, 127.5, 126.4, 126.1, 122.6, 115.3, 115.1, 115.0, 114.8, 66.8, 46.3, 22.7, 20.1, 15.8. |
| 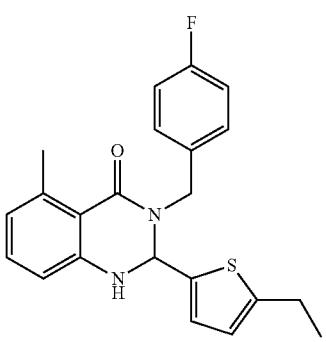 [SMILES: CCc1ccc(C2Nc3cccc(C)c3C(=O)N2Cc2ccc(F)cc2)s1] | BU62382C8<br>Retro2A4B15C8 | $C_{22}H_{21}FN_2OSNa^+$ Predicted: 403.1256<br>Found: 403.1262. $^1$H NMR (400 MHz, DMSO-d$_6$) δ = 7.50 (s, 1 H), 7.34 (dd, J = 5.6, 8.6 Hz, 2 H), 7.21 (d, J = 2.5 Hz, 1 H), 7.19-7.13 (m, 2 H), 7.11 (dd, J = 2.0, 8.1 Hz, 1 H), 6.85 (d, J = 3.5 Hz, 1 H), 6.67-6.60 (m, 2 H), 5.89 (d, J = 2.5 Hz, 1 H), 5.16 (d, J = 15.2 Hz, 1 H), 3.97 (d, J = 15.4 Hz, 1 H), 2.67 (q, J = 7.5 Hz, 2 H), 2.21 (s, 3 H), 1.13 (t, J = 7.5 Hz, 3 H). $^{13}$C NMR (101 MHz, DMSO-d$_6$) δ = 161.9, 146.6, 144.0, 141.4, 134.4, 129.6, 129.5, 127.5, 126.4, 126.1, 122.6, 115.3, 115.1, 115.0, 114.8, 66.8, 46.3, 22.7, 20.2, 15.8. |

TABLE 1-continued

| Structure | Name | Characterization data |
|---|---|---|
| [Structure with 4-fluorobenzyl group attached to N, 7-fluoro dihydroquinazolinone core, and 5-ethylthiophene substituent] | BU62382C9 Retro2A4B15C9 | $C_{21}H_{18}F_2N_2OSNa^+$ Predicted: 407.1006 Found: 407.1025. $^1H$ NMR (600 MHz, DMSO-$d_6$) δ = 7.74 (dd, J = 6.6, 8.8 Hz, 1 H), 7.66 (d, J = 2.6 Hz, 1 H), 7.37-7.30 (m, 2 H), 7.18-7.12 (m, 2 H), 6.89 (d, J = 3.7 Hz, 1 H), 6.65 (td, J = 1.0, 3.6 Hz, 1 H), 6.54 (dt, J = 2.4, 8.7 Hz, 1 H), 6.49 (dd, J = 2.2, 10.6 Hz, 1 H), 5.99 (d, J = 2.6 Hz, 1 H), 5.13 (d, J = 15.4 Hz, 1 H), 3.98 (d, J = 15.4 Hz, 1 H), 2.69 (q, J = 7.3 Hz, 2 H), 1.14 (t, J = 7.5 Hz, 3 H). $^{13}C$ NMR (151 MHz, DMSO-$d_6$) δ = 165.4, 162.7, 161.6, 148.7, 147.4, 141.5, 134.1, 134.1, 131.2, 131.1, 130.1, 130.0, 126.7, 123.2, 115.7, 115.6, 111.9, 105.7, 105.6, 101.1, 100.9, 67.2, 46.7, 23.2, 16.2. |
| [Structure with 4-fluorobenzyl group attached to N, 6-fluoro dihydroquinazolinone core, and 5-ethylthiophene substituent] | BU62382C10 Retro2A4B15C10 | $C_{21}H_{18}F_2N_2OSNa^+$ Predicted: 407.1006 Found: 407.1018. $^1H$ NMR (400 MHz, DMSO-$d_6$) δ = 7.43-7.37 (m, 2 H), 7.34 (dd, J = 5.6, 8.3 Hz, 2 H), 7.23-7.12 (m, 3 H), 6.87 (d, J = 3.5 Hz, 1 H), 6.76 (dd, J = 4.5, 8.8 Hz, 1 H), 6.66-6.62 (m, 1 H), 5.97 (d, J = 2.5 Hz, 1 H), 5.12 (d, J = 15.4 Hz, 1 H), 4.02 (d, J = 15.2 Hz, 1 H), 2.68 (q, J = 7.6 Hz, 2 H), 1.13 (t, J = 7.5 Hz, 3 H). $^{13}C$ NMR (151 MHz, DMSO-$d_6$) δ = 162.2, 161.0, 160.6, 155.8, 154.2, 146.7, 142.8, 140.9, 133.6, 133.6, 129.6, 129.5, 126.2, 122.6, 121.1, 120.9, 116.7, 116.6, 115.5, 115.5, 115.2, 115.1, 112.8, 112.6, 66.8, 46.4, 22.7, 15.6 |

Figure 12:
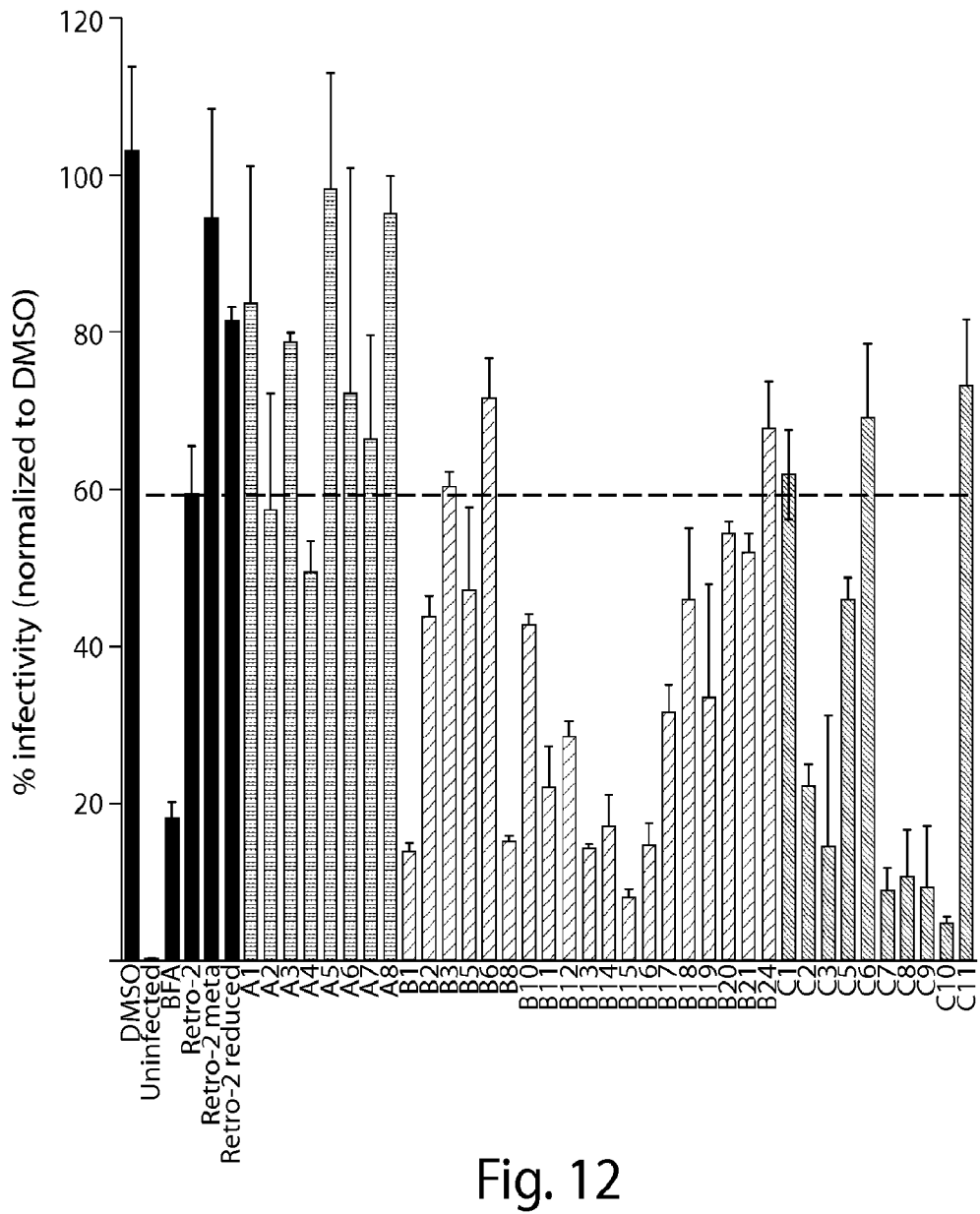
FIG. 12 depicts the inhibitory properties of Retro-2$^{cycl}$ analogs. All compounds were tested against JCPyV at 25 uM in 0.04% DMSO. The dashed line indicates the level of inhibition by Retro-2$^{cycl}$.

FIG. 12 depicts the inhibitory properties of Retro-2$^{cycl}$ analogs depicted in Table 1. All compounds were tested against JCPyV at 25 uM in 0.04% DMSO.

X-Ray Crystallography

A specimen of $C_{19}H_{16}N_2OS$, approximate dimensions 0.150 mm×0.250 mm×0.250 mm, was used for the X-ray crystallographic analysis. The X-ray intensity data were measured on a Bruker Apex 1 diffractometer.

The integration of the data using a monoclinic unit cell yielded a total of 5596 reflections to a maximum θ angle of 18.43° (1.12 Å resolution), of which 1181 were independent (average redundancy 4.738, completeness=98.5%, $R_{int}$=6.64%, $R_{sig}$=5.20%) and 899 (76.12%) were greater than 2σ($F^2$). The final cell constants of a=6.575(6) Å, b=13.446(12) Å, c=18.616(17) Å, β=99.161(12)°, volume=1625.(3) Å$^3$, are based upon the refinement of the XYZ-centroids of reflections above 20 σ(I). The calculated minimum and maximum transmission coefficients (based on crystal size) are 0.9506 and 0.9699.

The structure was solved and refined using the Bruker SHELXTL Software Package, using the space group P 2(1)/c, with Z=4 for the formula unit, $C_{19}H_{16}N_2O$ S. The final anisotropic full-matrix least-squares refinement on $F^2$ with 227 variables converged at R1=5.01%, for the observed data and wR2=13.47% for all data. The goodness-of-fit was 1.093. The largest peak in the final difference electron density synthesis was 0.145 e$^-$/Å$^3$ and the largest hole was −0.194 e$^-$/Å$^3$ with an RMS deviation of 0.039 e$^-$/Å$^3$. On the basis of the final model, the calculated density was 1.310 g/cm$^3$ and F(000), 672 e$^-$. Disorder in this crystal structure was noted for the thiophene ring and the methine carbon atom of the dihydroquinazolinone ring to which it is attached. This disorder was nicely modeled by a nearly 180° rotation about the C—C bond between C(14) and C(15) bond as well as an out of plane displacement of the C(14) relative to the remaining nine atoms of the dihydroquinazolinone ring. Constraints were applied to the fragment C(14) through C(19) and S(1) in the initial stages of the refinement but were released in the final model. The final model refined to a nearly 2:1 ratio of conformers. Only the major conformer is depicted in FIG. 8.

Other Embodiments

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A method of treating a viral infection, the method comprising administering to a subject suffering from or likely to suffer from a viral infection an effective amount of a compound of Formula (II):

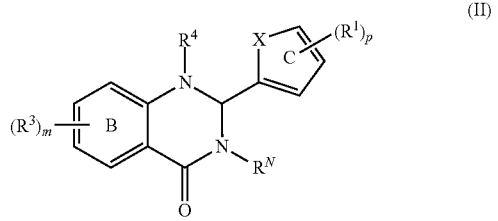

or a pharmaceutically acceptable salt, tautomer, or stereoisomer thereof;
wherein:
X is O, S, or NH;
each instance of $R^1$ is independently halo, $-NO_2$, $-CN$, $-SCN$, $-OR^{41}$, $-SR^{41}$, $-N(R^{41})_2$, $-C(=O)R^{41}$, $-OC(=O)R^{41}$, $-SC(=O)R^{41}$, $-NR^{41}C(C)R^{41}$, $-S(=O)_2R^{41}$, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl;
each instance of $R^{41}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, substituted or unsubstituted hydroxyl, substituted or unsubstituted amino, substituted or unsubstituted thiol, an oxygen protecting group when attached to an oxygen atom, a sulfur protecting group when attached to a sulfur atom, or a nitrogen protecting group when attached to a nitrogen atom, or two $R^{41}$ groups are joined to form a substituted or unsubstituted heterocyclic or substituted or unsubstituted heteroaryl ring;
or two $R^1$ groups are joined to form a substituted or unsubstituted aryl, substituted or unsubstituted heteroaryl, substituted or unsubstituted carbocyclic, or substituted or unsubstituted heterocyclic ring;
$R^N$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl;
each instance of $R^3$ is independently halo, $-NO_2$, $-CN$, $-SCN$, $-OR^{43}$, $-SR^{43}$, $-N(R^{43})_2$, $-C(=O)R^{43}$, $-OC(=O)R^{43}$, $-SC(=O)R^{43}$, $-NR^{43}C(=O)R^{43}$, $-S(=O)_2R^{43}$, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl,
each instance of $R^{43}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, substituted or unsubstituted hydroxyl, substituted or unsubstituted amino, substituted or unsubstituted thiol, an oxygen protecting group when attached to an oxygen atom, a sulfur protecting group when attached to a sulfur atom, or a nitrogen protecting group when attached to a nitrogen atom, or two $R^{43}$ groups are joined to form a substituted or unsubstituted heterocyclic or substituted or unsubstituted heteroaryl ring;
or two $R^3$ groups are joined to form a substituted or unsubstituted aryl, substituted or unsubstituted heteroaryl, substituted or unsubstituted carbocyclic, or substituted or unsubstituted heterocyclic ring;
$R^4$ is hydrogen, substituted or unsubstituted alkyl, or a nitrogen protecting group;
p is 0, 1, or 2; and
m is 0, 1, 2, 3, or 4.

2. The method of claim 1, wherein the viral infection is an infection caused by human papillomavirus, human immunodeficiency virus, influenza virus, or polyomavirus.

3. The method of claim 1, wherein X is S.

4. The method of claim 1, wherein $R^1$ is halo or substituted or unsubstituted $C_{1-6}$ alkyl.

5. The method of claim 4, wherein $R^1$ is methyl, ethyl, n-propyl, isopropyl, n-butyl, tert-butyl, sec-butyl, iso-butyl, n-pentyl, 3-pentanyl, amyl, neopentyl, 3-methyl-2-butanyl, tertiary amyl, or n-hexyl.

6. The method of claim 1, wherein $R^N$ is a group of formula:

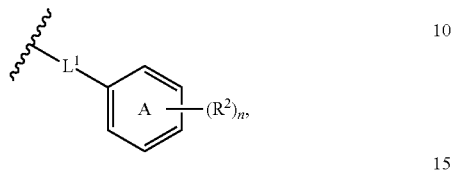

wherein:

$L^1$ is a bond, substituted or unsubstituted alkylene, substituted or unsubstituted alkenylene, or substituted or unsubstituted alkynylene;

each instance of $R^2$ is independently halo, $-NO_2$, $-CN$, $-SCN$, $-OR^{A2}$, $-SR^{A2}$, $-N(R^{A2})_2$, $-C(=O)R^{A2}$, $-OC(=O)R^{A2}$, $-SC(=O)R^{A2}$, $-NR^{A2}C(=O)R^{A2}$, $-S(=O)_2R^{A2}$, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl;

each instance of $R^{A2}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, substituted or unsubstituted hydroxyl, substituted or unsubstituted amino, substituted or unsubstituted thiol, an oxygen protecting group when attached to an oxygen atom, a sulfur protecting group when attached to a sulfur atom, or a nitrogen protecting group when attached to a nitrogen atom, or two $R^{A2}$ groups are joined to form a substituted or unsubstituted heterocyclic or substituted or unsubstituted heteroaryl ring;

or two $R^2$ groups are joined to form a substituted or unsubstituted aryl, substituted or unsubstituted heteroaryl, substituted or unsubstituted carbocyclic, or substituted or unsubstituted heterocyclic ring; and n is 0, 1, 2, 3, 4 or 5.

7. The method of claim 6, wherein n is 1, 2, 3, 4, or 5, and each instance of $R^2$ is independently halo, $-NO_2$, or $-OR^{A2}$.

8. The method of claim 6, wherein $L^1$ is a bond.

9. The method of claim 6, wherein $L^1$ is substituted or unsubstituted $C_1$alkylene, substituted or unsubstituted $C_2$alkylene, or substituted or unsubstituted $C_3$alkylene.

10. The method of claim 1, wherein m is 0.

11. The method of claim 1, wherein m is 1, 2, 3, or 4, and each instance of $R^3$ is independently halo or substituted or unsubstituted alkyl.

12. The method of claim 1, wherein $R^4$ is hydrogen.

13. The method of claim 1, wherein the compound of Formula (II) is selected from the group consisting of:

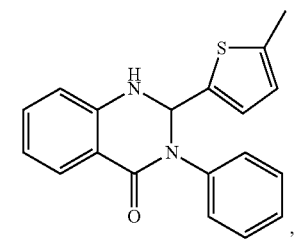 [SMILES: Cc1ccc(C2Nc3ccccc3C(=O)N2c2ccccc2)s1]

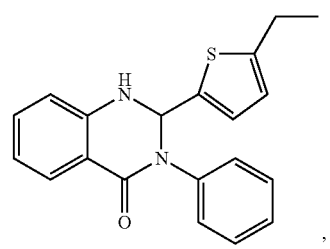

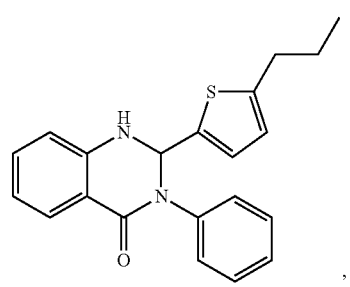

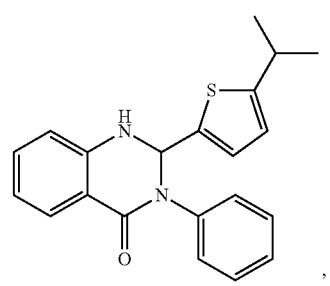

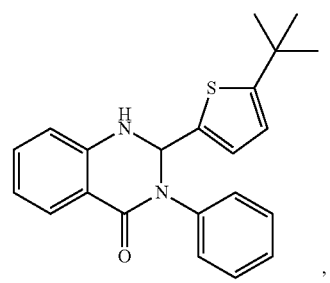

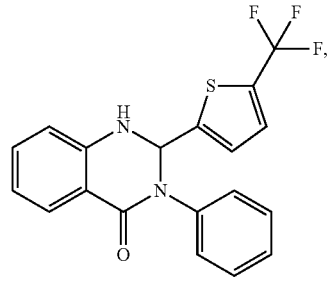

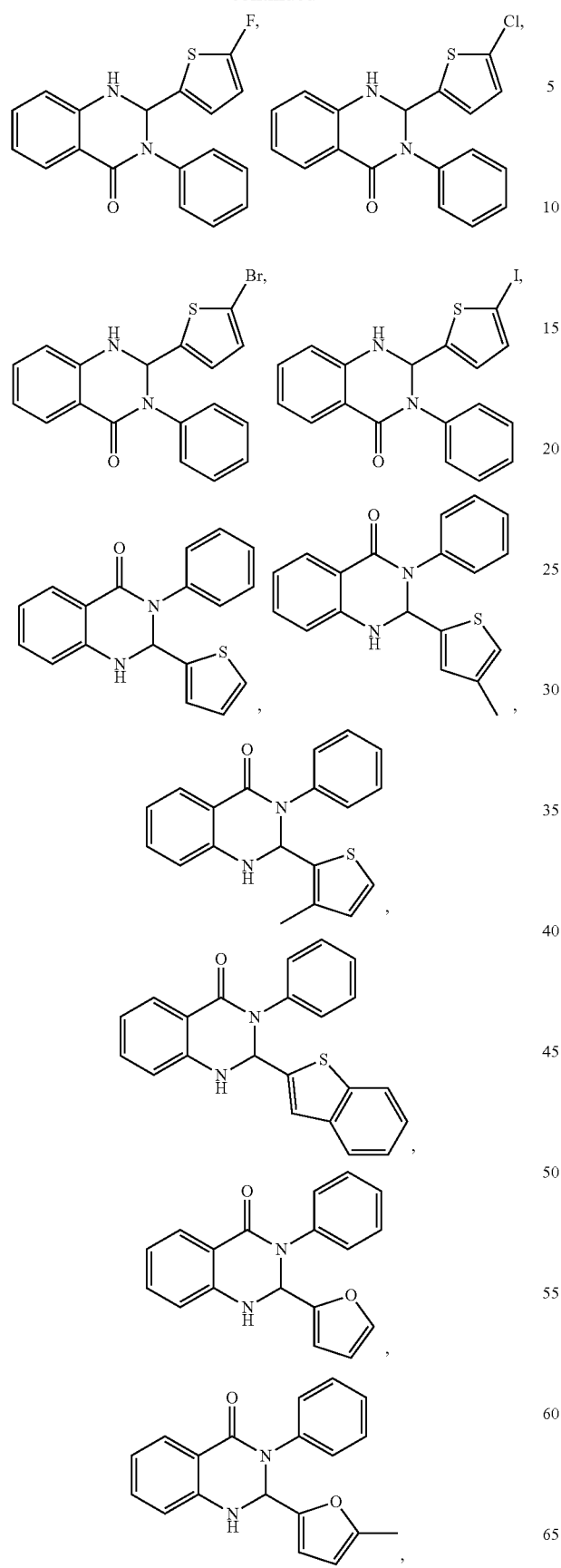
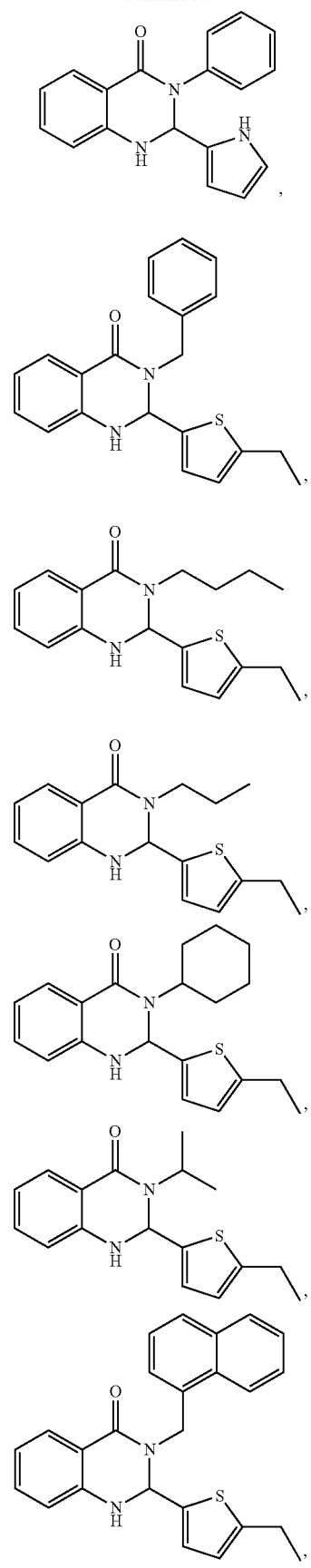

109
-continued
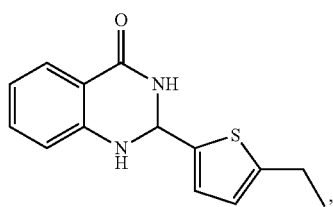
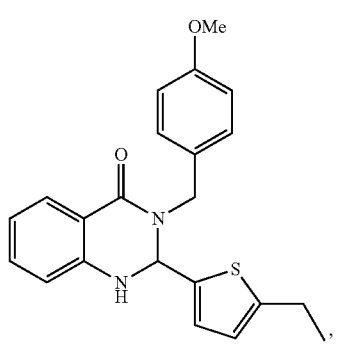
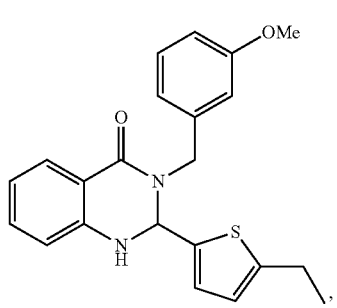
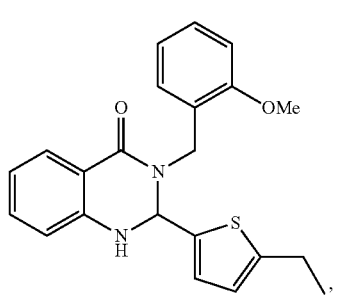
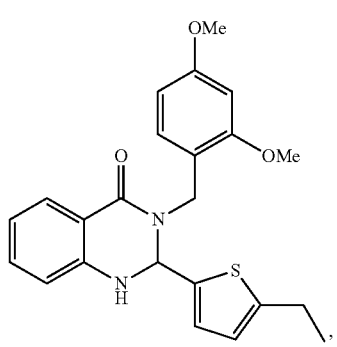
110
-continued
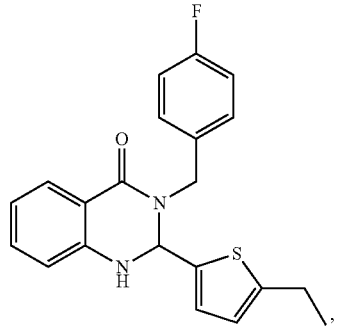
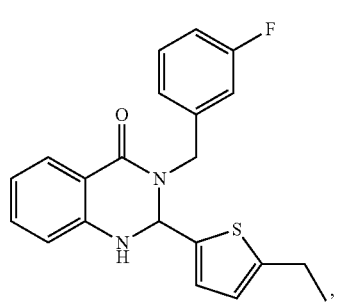
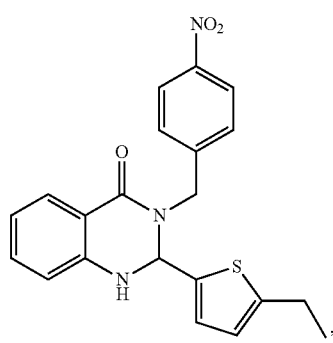
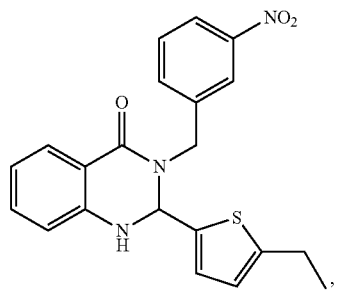
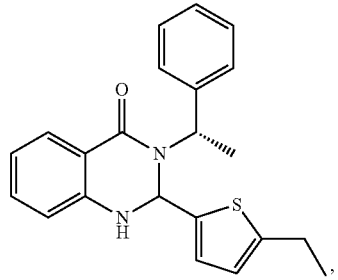

111
-continued
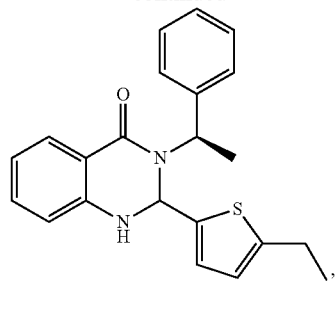
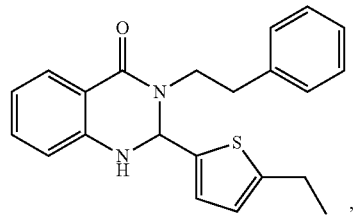
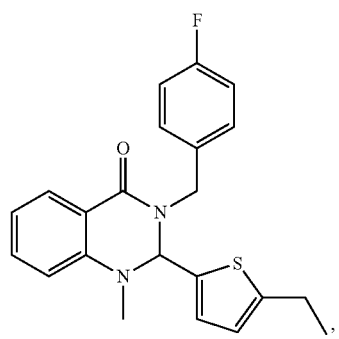
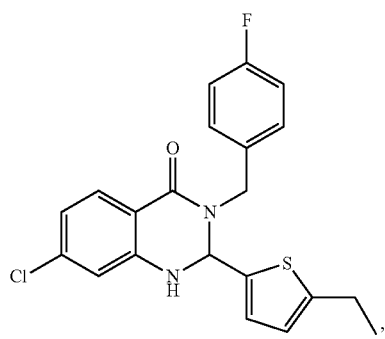
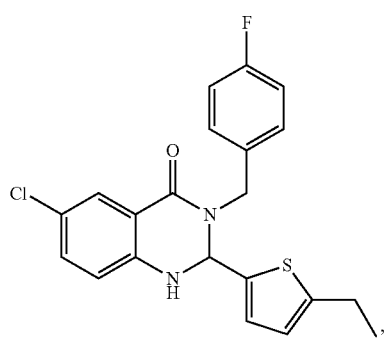
112
-continued
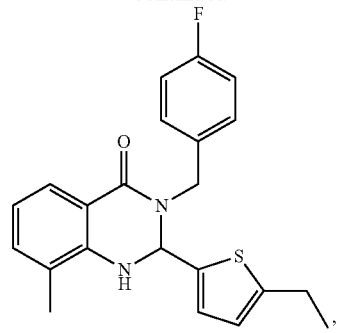
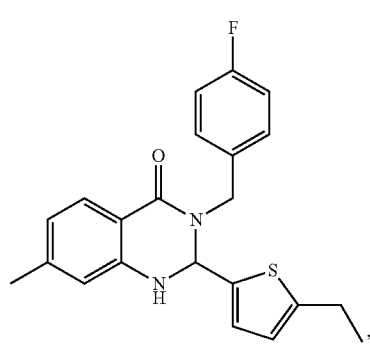
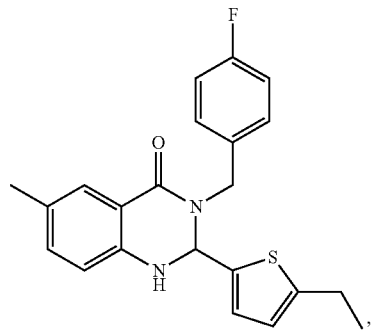
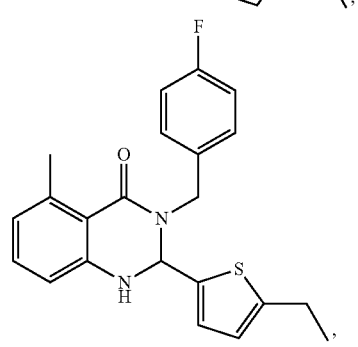
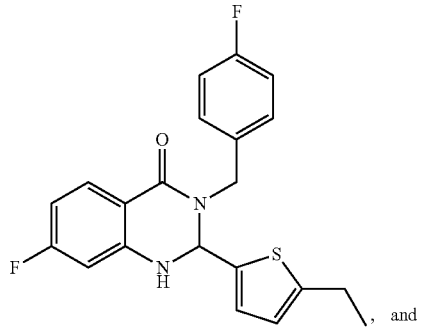
, and

113

-continued

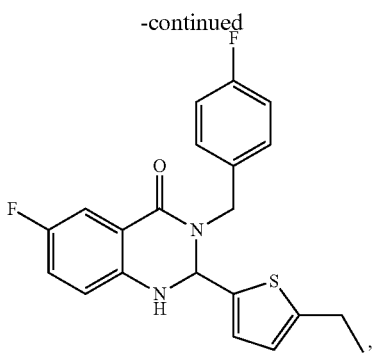

and pharmaceutically acceptable salts, tautomers, and stereoisomers thereof.

14. A method of treating an infection by a bacteria that secretes an $AB_5$ toxin, the method comprising administering to a subject suffering from or likely to suffer from the infection an effective amount of a compound of Formula (II-a):

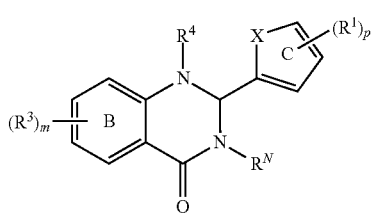

(II)

or a pharmaceutically acceptable salt, tautomer, or stereoisomer thereof;
wherein:
X is S;
$R^1$ is halo, —$NO_2$, —CN, —SCN, —$OR^{41}$, —$SR^{41}$, —$N(R^{41})_2$, —C(=O)$R^{41}$, —OC(=O)$R^{41}$, —SC(=O)$R^{41}$, —$NR^{41}$C(=O)$R^{41}$, —S(=O)$_2R^{41}$, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl;
each instance of $R^{41}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, substituted or unsubstituted hydroxyl, substituted or unsubstituted amino, substituted or unsubstituted thiol, an oxygen protecting group when attached to an oxygen atom, a sulfur protecting group when attached to a sulfur atom, or a nitrogen protecting group when attached to a nitrogen atom, or two $R^{41}$ groups are joined to form a substituted or unsubstituted heterocyclic or substituted or unsubstituted heteroaryl ring;
$R^N$ is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl;
each instance of $R^3$ is independently halo, —$NO_2$, —CN, —SCN, —$OR^{43}$, —$SR^{43}$, —$N(R^{43})_2$, —C(=O)$R^{43}$, —OC(=O)$R^{43}$, —SC(=O)$R^{43}$, —$NR^{43}$C(=O)$R^{43}$, —S(=O)$_2R^{43}$, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl,
each instance of $R^{43}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, substituted or unsubstituted hydroxyl, substituted or unsubstituted amino, substituted or unsubstituted thiol, an oxygen protecting group when attached to an oxygen atom, a sulfur protecting group when attached to a sulfur atom, or a nitrogen protecting group when attached to a nitrogen atom, or two $R^{43}$ groups are joined to form a substituted or unsubstituted heterocyclic or substituted or unsubstituted heteroaryl ring;
or two $R^3$ groups are joined to form a substituted or unsubstituted aryl, substituted or unsubstituted heteroaryl, substituted or unsubstituted carbocyclic, or substituted or unsubstituted heterocyclic ring;
$R^4$ is hydrogen, substituted or unsubstituted alkyl, or a nitrogen protecting group;
and
m is 0, 1, 2, 3, or 4;
provided the compound is not:

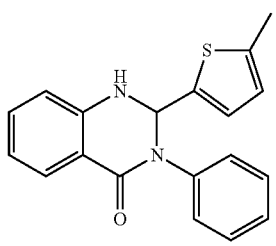

15. The method of claim 14, wherein the bacteria secreting an $AB_5$ toxin is *E. coli* bacteria.

16. The method of claim 14, wherein the $AB_5$ toxin is selected from the group consisting of ricin, Shiga toxin, Shiga-like toxins, cholera toxin, heat-labile enterotoxin, pertussis toxin, and subtilase cytotoxin.

17. A compound of Formula (II-a):

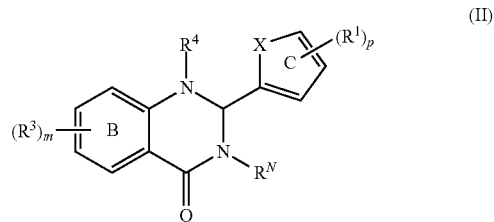

(II)

or a pharmaceutically acceptable salt, tautomer, or stereoisomer thereof;
wherein:
X is S;
R¹ is halo, —NO₂, —CN, —SCN, —OR^{A1}, —SR^{A1}, —N(R^{A1})₂, —C(=O)R^{A1}, —OC(=O)R^{A1}, —SC(=O)R^{A1}, —NR^{A1}C(=O)R^{A1}, —S(=O)₂R^{A1}, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl;
each instance of R^{A1} is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, substituted or unsubstituted hydroxyl, substituted or unsubstituted amino, substituted or unsubstituted thiol, an oxygen protecting group when attached to an oxygen atom, a sulfur protecting group when attached to a sulfur atom, or a nitrogen protecting group when attached to a nitrogen atom, or two R^{A1} groups are joined to form a substituted or unsubstituted heterocyclic or substituted or unsubstituted heteroaryl ring;
R^{N} is hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl;
each instance of R³ is independently halo, —NO₂, —CN, —SCN, —OR^{A3}, —SR^{A3}, —N(R^{A3})₂, —C(=O)R^{A3}, —OC(=O)R^{A3}, —SC(=O)R^{A3}, —NR^{A3}C(=O)R^{A3}, —S(=O)₂R^{A3}, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl,
each instance of R^{A3} is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, substituted or unsubstituted hydroxyl, substituted or unsubstituted amino, substituted or unsubstituted thiol, an oxygen protecting group when attached to an oxygen atom, a sulfur protecting group when attached to a sulfur atom, or a nitrogen protecting group when attached to a nitrogen atom, or two R^{A3} groups are joined to form a substituted or unsubstituted heterocyclic or substituted or unsubstituted heteroaryl ring;
or two R³ groups are joined to form a substituted or unsubstituted aryl, substituted or unsubstituted heteroaryl, substituted or unsubstituted carbocyclic, or substituted or unsubstituted heterocyclic ring;
R⁴ is hydrogen, substituted or unsubstituted alkyl, or a nitrogen protecting group;
and
m is 0, 1, 2, 3, or 4;

provided the compound is not:

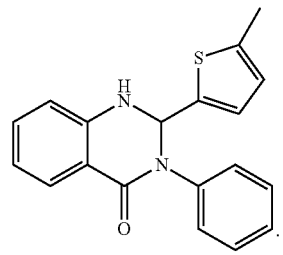 [SMILES: Cc1ccc(C2Nc3ccccc3C(=O)N2c2ccccc2)s1]

18. The compound of claim 17, wherein the compound is:

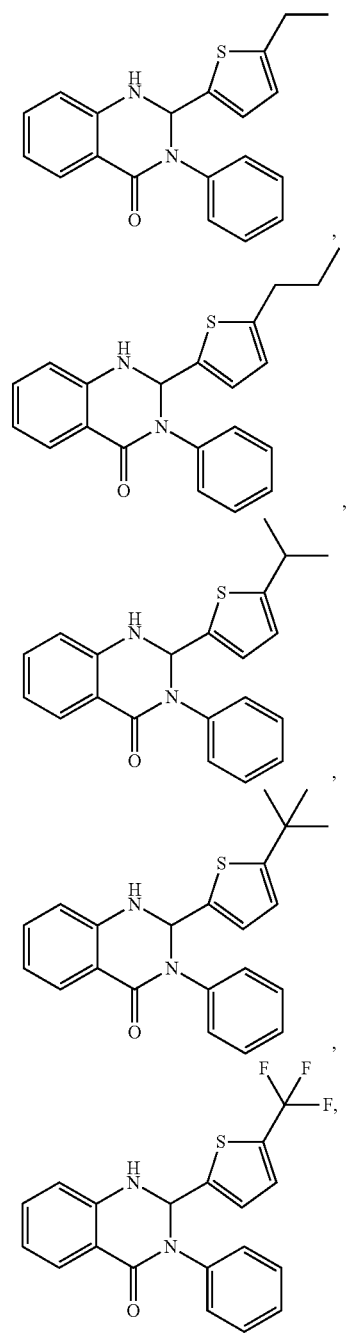

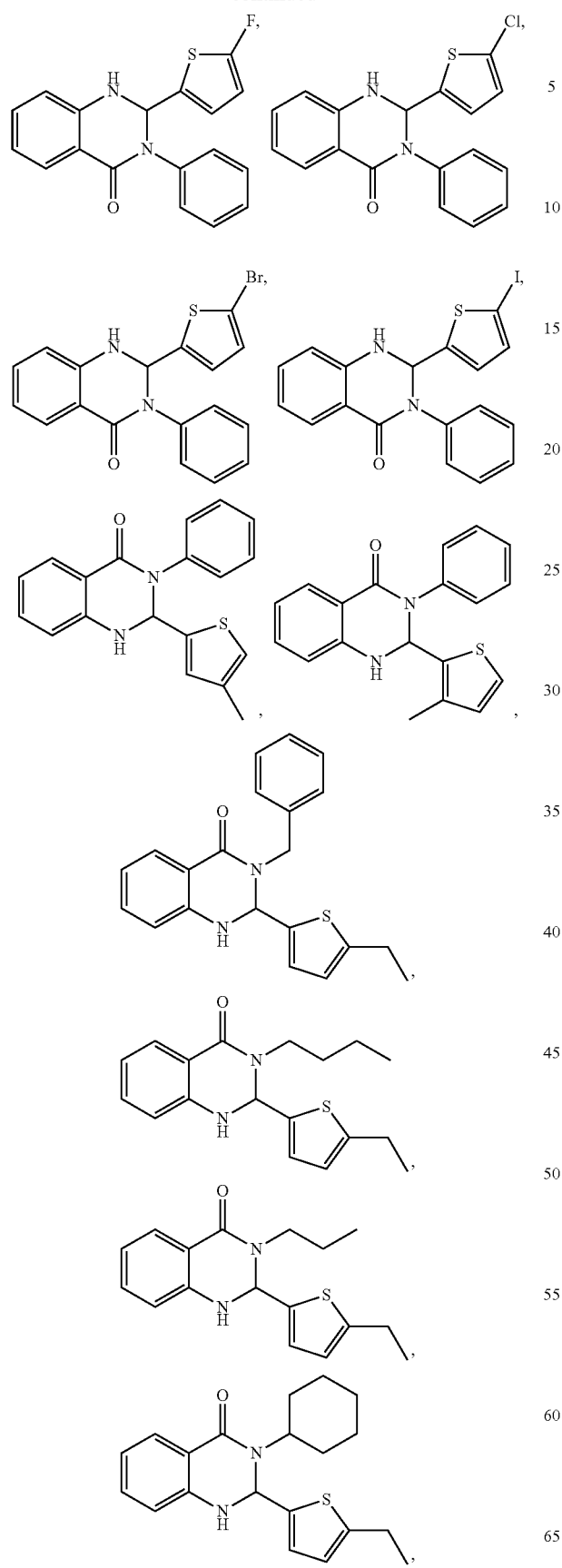
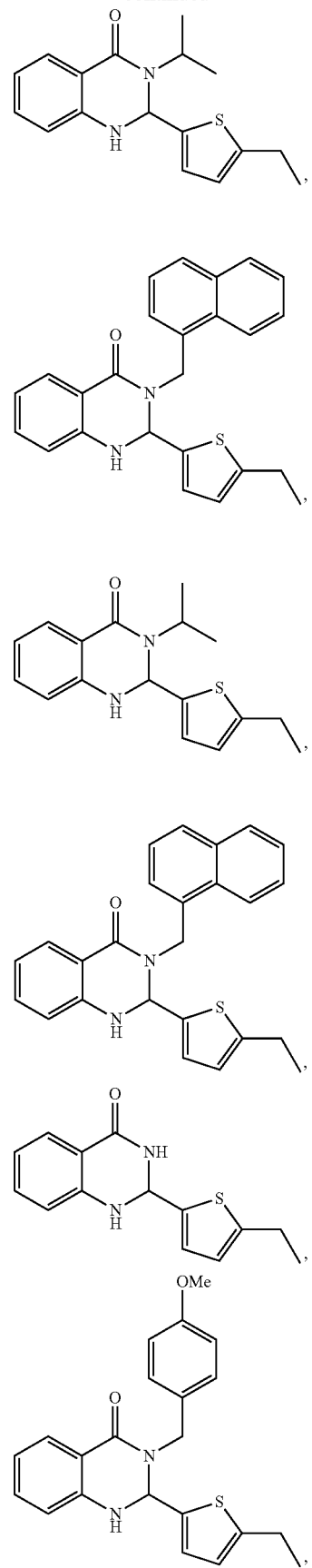

119
-continued
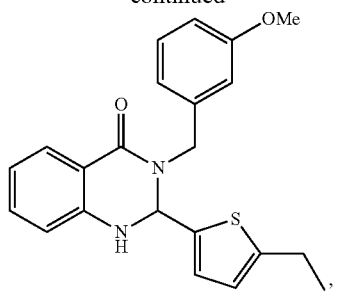
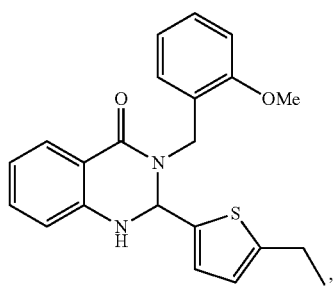
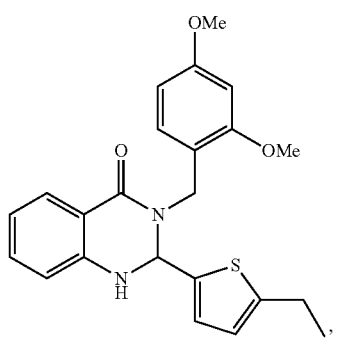
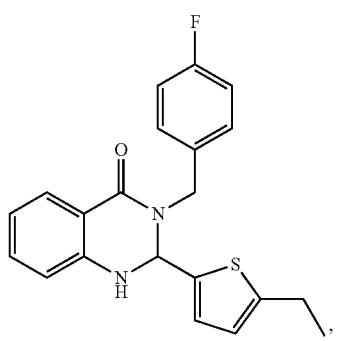
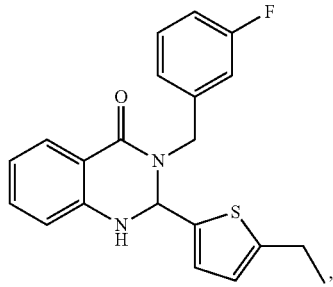
120
-continued
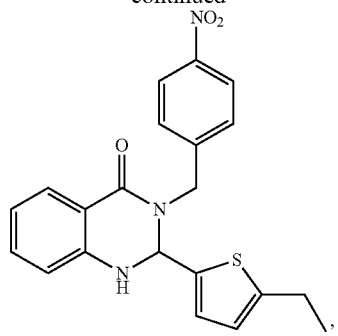
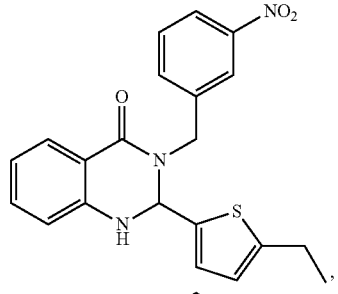
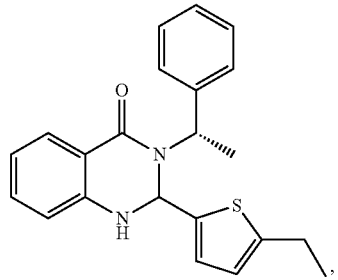
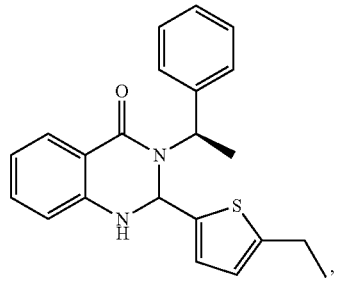
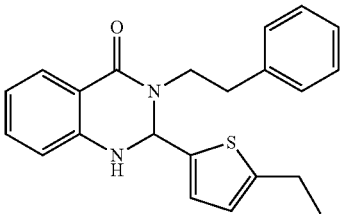
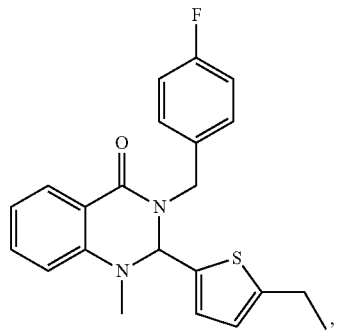

-continued

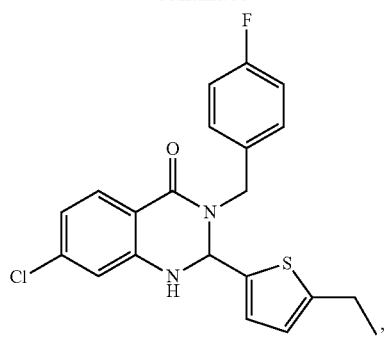

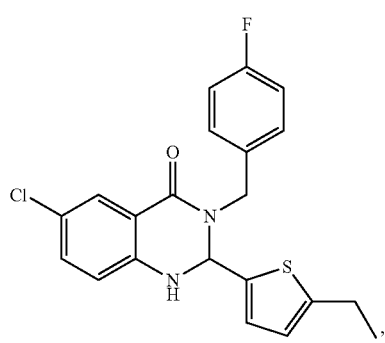

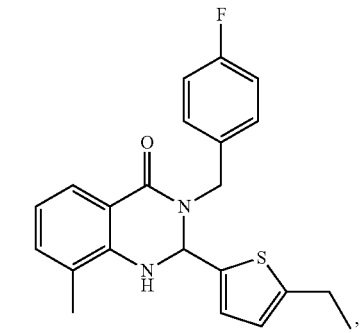

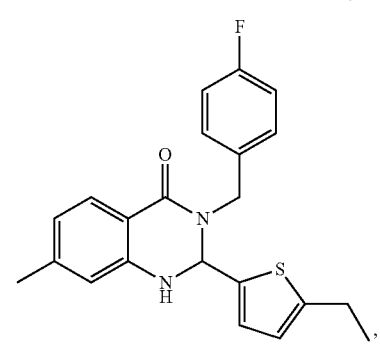

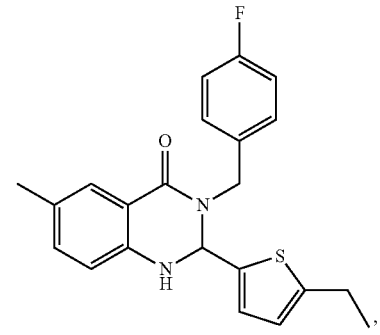

-continued

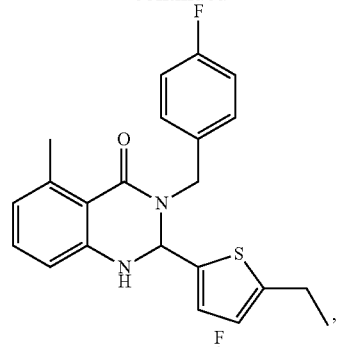

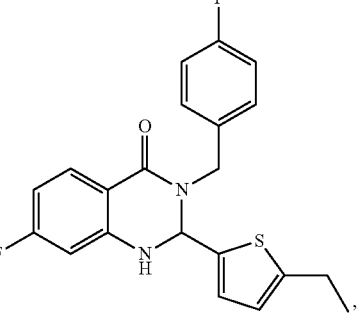

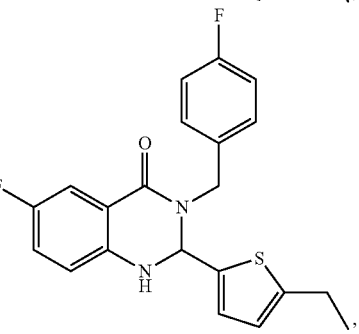

or a pharmaceutically acceptable salt, tautomer, or stereoisomer thereof.

19. A pharmaceutical composition comprising a compound of claim 17, or a pharmaceutically acceptable salt, tautomer, or stereoisomer thereof, and a pharmaceutically acceptable excipient.

20. The compound of claim 17, wherein $R^1$ is halo or substituted or unsubstituted $C_{1-6}$ alkyl.

21. The compound of claim 17, wherein $R^1$ is ethyl, n-propyl, isopropyl, n-butyl, tert-butyl, sec-butyl, iso-butyl, n-pentyl, 3-pentanyl, amyl, neopentyl, 3-methyl-2-butanyl, tertiary amyl, or n-hexyl.

22. The compound of claim 21, wherein $R^1$ is ethyl.

23. The compound of claim 17, wherein $R^N$ is a group of formula:

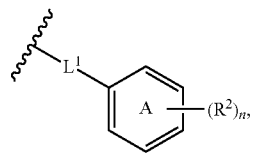

wherein:
  $L^1$ is a bond, substituted or unsubstituted alkylene, substituted or unsubstituted alkenylene, or substituted or unsubstituted alkynylene;

each instance of $R^2$ is independently halo, $-NO_2$, $-CN$, $-SCN$, $-OR^{A2}$, $-SR^{A2}$, $-N(R^{A2})_2$, $-C(=O)R^{A2}$, $-OC(=O)R^{A2}$, $-SC(=O)R^{A2}$, $-NR^{A2}C(=O)R^{A2}$, $-S(=O)_2R^{A2}$, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, each instance of $R^{A2}$ is independently hydrogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, substituted or unsubstituted hydroxyl, substituted or unsubstituted amino, substituted or unsubstituted thiol, an oxygen protecting group when attached to an oxygen atom, a sulfur protecting group when attached to a sulfur atom, or a nitrogen protecting group when attached to a nitrogen atom, or two $R^{A2}$ groups are joined to form a substituted or unsubstituted heterocyclic or substituted or unsubstituted heteroaryl ring;

or two $R^2$ groups are joined to form a substituted or unsubstituted aryl, substituted or unsubstituted heteroaryl, substituted or unsubstituted carbocyclic, or substituted or unsubstituted heterocyclic ring; and n is 0, 1, 2, 3, 4 or 5.

24. The compound of claim 23, wherein n is 1, 2, 3, 4, or 5, and each instance of $R^2$ is independently halo, $-NO_2$, or $-OR^{A2}$.

25. The compound of claim 24, wherein n is 1, and $R^2$ is halo.

26. The compound of claim 23, wherein $L^1$ is a bond.

27. The compound of claim 23, wherein $L^1$ is substituted or unsubstituted $C_1$alkylene, substituted or unsubstituted $C_2$alkylene, or substituted or unsubstituted $C_3$alkylene.

28. The compound of claim 27, wherein $L^1$ is substituted or unsubstituted $C_1$alkylene.

29. The compound of claim 17, wherein m is 0.

30. The compound of claim 17, wherein m is 1.

31. The compound of claim 17, wherein m is 1, 2, 3, or 4, and each instance of $R^3$ is independently halo or substituted or unsubstituted alkyl.

32. The compound of claim 17, wherein $R^4$ is hydrogen.

33. The method of claim 7, wherein n is 1, and $R^2$ is halo.

34. The method of claim 9, wherein $L^1$ is substituted or unsubstituted $C_1$alkylene.

35. The method of claim 1, wherein m is 1.

36. The method of claim 1, wherein the compound is of Formula (II-a):

or a pharmaceutically acceptable salt, tautomer, or stereoisomer thereof, wherein X is S.

37. The method of claim 5, wherein $R^1$ is ethyl.

* * * * *